(12) United States Patent
Frauendorf et al.

(10) Patent No.: US 10,913,945 B2
(45) Date of Patent: Feb. 9, 2021

(54) NUCLEIC ACID LINKED TO A TRIVALENT GLYCOCONJUGATE

(71) Applicant: Silence Therapeutics GmbH, Berlin (DE)

(72) Inventors: Christian Frauendorf, Berlin (DE); Mark Cameron, Berlin (DE)

(73) Assignee: SILENCE THERAPEUTICS GMBH, Berlin (DE)

( * ) Notice: Subject to any disclaimer, the term of this patent is extended or adjusted under 35 U.S.C. 154(b) by 0 days.

(21) Appl. No.: 16/091,503

(22) PCT Filed: Apr. 5, 2017

(86) PCT No.: PCT/EP2017/058112
§ 371 (c)(1),
(2) Date: Oct. 4, 2018

(87) PCT Pub. No.: WO2017/174657
PCT Pub. Date: Oct. 12, 2017

(65) Prior Publication Data
US 2019/0119676 A1   Apr. 25, 2019

(30) Foreign Application Priority Data
Apr. 5, 2016   (EP) .................................... 16163939

(51) Int. Cl.
| | | |
|---|---|---|
| *A61K 47/54* | (2017.01) | |
| *A61K 31/7125* | (2006.01) | |
| *A61K 47/56* | (2017.01) | |
| *C12N 15/113* | (2010.01) | |

(52) U.S. Cl.
CPC ........ *C12N 15/113* (2013.01); *A61K 31/7125* (2013.01); *A61K 47/549* (2017.08); *A61K 47/56* (2017.08); *C12N 2310/14* (2013.01); *C12N 2310/351* (2013.01); *C12N 2320/32* (2013.01)

(58) Field of Classification Search
CPC ...... A61K 31/7084–713; A61K 47/549; A61K 47/56
See application file for complete search history.

(56) References Cited

U.S. PATENT DOCUMENTS

| | | |
|---|---|---|
| 5,378,825 A | 1/1995 | Cook et al. |
| 5,753,613 A | 5/1998 | Ansell et al. |
| 5,820,873 A | 10/1998 | Choi et al. |
| 5,885,613 A | 3/1999 | Holland et al. |
| 5,885,968 A | 3/1999 | Biessen et al. |
| 6,326,199 B1 | 12/2001 | Cook et al. |
| 6,673,611 B2 | 1/2004 | Thompson et al. |

FOREIGN PATENT DOCUMENTS

| | | |
|---|---|---|
| WO | WO-2014179620 A1 | 11/2014 |
| WO | WO-2016055601 A1 | 4/2016 |

OTHER PUBLICATIONS

Akinc, Akin, et al., "Targeted delivery of RNAi therapeutics with endogenous and exogenous ligand-based mechanisms." Molecular Therapy 18.7 (2010): 1357-1364.
Biessen, E. A. L., et al, "The cholesterol derivative of a triantennary galactoside with high affinity for the hepatic asialoglycoprotein receptor: a potent cholesterol lowering agent." Journal of medicinal chemistry 38.11 (1995): 1846-1852.
Dubber, Michael, and Jean MJ Fréchet. "Solid-phase synthesis of multivalent glycoconjugates on a DNA synthesizer." Bioconjugate chemistry 14.1 (2003): 239-246.
Elbashir, Sayda M., et al., "RNA interference is mediated by 21-and 22-nucleotide RNAs." Genes & development 15.2 (2001): 188-200.
Fehring, V., et al., "Delivery of therapeutic siRNA to the lung endothelium via novel lipoplex formulation DACC." Molecular Therapy 22.4 (2014): 811-820.
Fire, Andrew, et al., "Potent and specific genetic interference by double-stranded RNA in Caenorhabditis elegans." nature 391.6669 (1998): 806.
Ishibashi, Shun, et al., "Asialoglycoprotein receptor deficiency in mice lacking the minor receptor subunit." Journal of Biological Chemistry 269.45 (1994): 12624-12628.
Li, Long-Cheng, et al., "Small dsRNAs induce transcriptional activation in human cells." Proceedings of the National Academy of Sciences 103.46 (2006): 17337-17342.
Prakash, Thazha P., et al., "Solid-phase synthesis of 5'-triantennary N-acetylgalactosamine conjugated antisense oligonucleotides using phosphoramidite chemistry." Bioorganic & medicinal chemistry letters 25.19 (2015): 4127-4130.
Weigel, Paul H., and Jasper HN Yik, "Glycans as endocytosis signals: the cases of the asialoglycoprotein and hyaluronan/chondroitin sulfate receptors." Biochimica et Biophysica Acta (BBA)-General Subjects 1572.2-3 (2002): 341-363.

*Primary Examiner* — Leigh C Maier
(74) *Attorney, Agent, or Firm* — Marshall, Gerstein & Borun LLP

(57) ABSTRACT

The present invention relates to a compound comprising a modified saccharide moiety conjugated to a nucleic acid. The compound is useful in medicine for RNA interference therapy or for research and diagnostic purposes. In particular, the compound is useful in treating liver disease.

3 Claims, 8 Drawing Sheets
Specification includes a Sequence Listing.

NUCLEIC ACID LINKED TO A TRIVALENT GLYCOCONJUGATE

CROSS-REFERENCE TO RELATED APPLICATIONS

This Application is a national phase entry of International Application No. PCT/EP2017/058112, filed on Apr. 5, 2017 which claims priority to EP Application No. 16163939.8 filed on Apr. 5, 2016, each of which is incorporated herein by reference in its entirety.

INCORPORATION BY REFERENCE OF MATERIAL SUBMITTED ELECTRONICALLY

This application contains, as a seperate part of disclosure, a sequence listing in computer-readable form (filename: 55815_SeqListing.text; 2,614 bytes; created: Oct. 29, 2020) which is incorporated by reference in its entirety.

FIELD OF THE INVENTION

The present invention relates to novel nucleic acid conjugate compounds. The invention further relates to compositions comprising said conjugates and their use in medicine, research and diagnostics. The novel conjugate compounds may be used in the treatment of many diseases including central-nervous-system diseases, inflammatory diseases, metabolic disorders, genetic and inherited diseases, oncology, infectious diseases, and ocular disease.

BACKGROUND OF THE INVENTION

Double-stranded RNA (dsRNA) has been shown to block gene expression (Fire et al., 1998 and Elbashir et al., 2001) and this has been termed RNA interference or "RNAi", mediated by interfering RNA molecules (iRNA). Short dsRNA directs gene-specific, post-transcriptional silencing in many organisms, including vertebrates, and has provided a new tool for studying gene function. RNAi is mediated by RNA-induced silencing complex (RISC), a sequence-specific, multi-component nuclease that destroys messenger RNAs homologous to the silencing trigger. iRNAs (interfering RNA) such as siRNA (short interfering RNA), antisense RNA, and micro-RNA are oligonucleotides that prevent the formation of proteins by gene-silencing i.e. inhibiting translation of the protein. Gene-silencing agents are becoming increasingly important for therapeutic applications in medicine.

Thus, means for efficient delivery of oligonucleotides, in particular double stranded siRNAs, to cells in vivo is becoming increasingly important and requires specific targeting and substantial protection from the extracellular environment, particularly serum proteins. One method of achieving specific targeting is to conjugate a targeting moiety to the iRNA duplex agent. The targeting moiety helps in targeting the iRNA duplex agent to the required target site and there is a need to design appropriate targeting moieties for the desired receptor sites for the conjugated molecules to be taken up by the cells such as by endocytosis.

For example, the Asialoglycoprotein receptor (ASGP-R) is a high capacity receptor, which is highly abundant on hepatocytes. One of the first disclosures of triantennary cluster glycosides was in U.S. Pat. No. 5,885,968. Conjugates having three GalNAc ligands and comprising phosphate groups are known and are described in Dubber et al. (2003). The ASGP-R shows a 50-fold higher affinity for N-Acetyl-D-Galactosylamine (GalNAc) than D-Gal.

Hepatocytes expressing the Lectin (asialoglycoprotein receptor; ASGPR), which recognizes specifically terminal β-galactosyl subunits of glycosylated proteins or other oligosaccharides (P. H. Weigel et. al., 2002,) can be used for targeting a drug to the liver by covalent coupling of galactose or galactosamine to the drug substance (S. Ishibashi, et. al. 1994). Furthermore the binding affinity can be significantly increased by the multi-valency effect, which is achieved by the repetition of the targeting unit (E. A. L. Biessen et. al., 1995).

The ASGPR is a mediator for an active endosomal transport of terminal β-galactosyl containing glycoproteins, thus ASGPR is highly suitable for targeted delivery of drug candidates like siRNA, which have to be delivered into a cell (Akinc et al.).

However, targeting ligands developed so far do not always translate to in vivo setting and there is a clear need for more efficacious receptor specific ligand conjugated iRNA duplex agents and methods for their preparation for the in vivo delivery of oligonucleotide therapeutics, nucleic acids and double stranded siRNAs. The present invention attempts to address these needs.

SUMMARY OF THE INVENTION

The present invention relates to conjugate compounds having three saccharide ligands and modified phosphate groups within the saccharide portion of the compounds. These conjugate compounds have been shown to have improved potency and duration in vivo. In addition, the conjugate groups are much easier to prepare compared to conjugates known in the art.

The conjugate compounds of the present invention have the formula I:

$$[S\text{---}X^1\text{---}P\text{---}X^2]_3\text{-}A\text{-}X^3\text{---}Z \qquad (I)$$

wherein:
S represents a saccharide;
$X^1$ represents $C_3$-$C_6$ alkylene or an ethylene glycol stem (—CH$_2$—CH$_2$—O)$_m$(—CH$_2$)$_2$— wherein m is 1, 2, or 3;
P is a modified phosphate;
$X^2$ is alkylene or an alkylene ether of the formula (—CH$_2$)$_n$—O—CH$_2$— where n=1-6;
A is a branching unit;
$X^3$ represents a bridging unit;
Z is a nucleic acid;
and where the linkage between $X^3$ and Z is a phosphate or thiophosphate.

The nucleic acid may be selected from RNAi, siRNA, siNA, antisense nucleic acid, ribozymes, aptamers and spiegelmers. The present invention also relates to pharmaceutical compositions comprising the conjugate compound of formula I.

DETAILED DESCRIPTION OF THE INVENTION

The definitions and explanations below are for the terms as used throughout this entire document including both the specification and the claims.

Unless specified otherwise, the following terms have the following meanings:

"Conjugate" or "conjugate group" means an atom or group of atoms bound to an oligonucleotide or oligomeric compound. In general, conjugate groups modify one or more properties of the compound to which they are attached, including, but not limited to pharmacodynamics, pharmacokinetic, binding, absorption, cellular distribution, cellular uptake, charge and/or clearance properties.

"GalNAc" means N-acetyl galactosamine.

$C_x$-$C_y$ alkyl refers to a saturated aliphatic hydrocarbon group having x-y carbon atoms which may be linear or branched. For example $C_1$-$C_6$ alkyl and includes $C_1$, $C_2$, $C_3$, $C_4$, $C_5$ and $C_6$. "Branched" means that at least one carbon branch point is present in the group. For example, tert-butyl and isopropyl are both branched groups. Examples of $C_1$-$C_6$ alkyl groups include methyl, ethyl, propyl, butyl, 2-methyl-1-propyl, 2-methyl-2-propyl, 2-methyl-1-butyl, 3 methyl-1-butyl, 2-methyl-3-butyl, 2,2-dimethyl-1-propyl, 2-methyl-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, tert-butyl, n-pentyl, isopentyl, neopentyl and n-hexyl. This also applies for $C_1$-$C_6$ alkylene.

$C_x$-$C_y$ alkoxy refers to a group or part of a group having an —O—$C_x$-$C_y$ alkyl group according to the definition of $C_x$-$C_y$ alkyl above. $C_1$-$C_3$ alkoxy contains from 1 to 3 carbon atoms and includes $C_1$, $C_2$ and $C_3$. Examples of $C_1$-$C_3$ alkoxy include methoxy, ethoxy, propoxy and isopropoxy. Alkoxy as employed herein also extends to embodiments in which the or an oxygen atom (e.g. a single oxygen atom) is located within the alkyl chain, for example $CH_2CH_2OCH_3$ or $CH_2OCH_3$. Thus the alkoxy may be linked through carbon to the remainder of the molecule, for example, —$CH_2CH_2OCH_3$, or alternatively, the alkoxy is linked through oxygen to the remainder of the molecule, for example —$OC_{1-3}$ alkyl. In certain instances, the alkoxy may be linked through oxygen to the remainder of the molecule but the alkoxy group contains a further oxygen atom, for example —$OCH_2CH_2OCH_3$.

The term "nucleic acid" refers to molecules composed of monomeric nucleotides. A nucleic acid includes ribonucleic acids (RNA), deoxyribonucleic acids (DNA), single-stranded nucleic acids (ssDNA), double-stranded nucleic acids (dsDNA), small interfering ribonucleic acids (siRNA) and microRNAs (miRNA). A nucleic acid may also comprise any combination of these elements in a single molecule.

The term "treat" or "treating" or "treatment" may include prophylaxis and means to ameliorate, alleviate symptoms, eliminate the causation of the symptoms either on a temporary or permanent basis, or to prevent or slow the appearance of symptoms of the named disorder or condition. The compounds of the invention are useful in the treatment of humans and non-human animals.

By "effective amount" or "therapeutically effective amount" or "effective dose" is meant that amount sufficient to elicit the desired pharmacological or therapeutic effects, thus resulting in effective prevention or treatment of the disorder. Prevention of the disorder is manifested by delaying the onset of the symptoms of the disorder to a medically significant extent. Treatment of the disorder is manifested by a decrease in the symptoms associated with the disorder or an amelioration of the reoccurrence of the symptoms of the disorder.

A "pharmaceutical composition" or "composition" means a mixture of substances suitable for administering to an individual. For example, a pharmaceutical composition can comprise one or more active agents and a pharmaceutical carrier e.g. a sterile aqueous solution.

In a first aspect, the present invention provides compounds of formula I:

$$[S—X^1—P—X^2]_3\text{-}A\text{-}X^3—Z \quad (I)$$

wherein:

S represents a saccharide;

$X^1$ represents $C_3$-$C_6$ alkylene or an ethylene glycol stem (—$CH_2$—$CH_2$—O)$_m$(—$CH_2$)$_2$— wherein m is 1, 2, or 3;

P is a modified phosphate;

$X^2$ is alkylene or an alkylene ether of the formula (—$CH_2$)$_n$—O—$CH_2$— where n=1-6;

A is a branching unit;

$X^3$ represents a bridging unit;

Z is a nucleic acid;

and where the linkage between $X^3$ and Z is a phosphate or thiophosphate.

In formula I, branching unit "A" branches into three in order to accommodate the three saccharide ligands. The branching unit is covalently attached to the tethered ligands and the nucleic acid. The branching unit may comprise a branched aliphatic group comprising groups selected from alkyl, amide, disulphide, polyethylene glycol, ether, thio-ether and hydroxyamino groups. The branching unit may comprise groups selected from alkyl and ether groups.

The branching unit A may have a structure selected from:

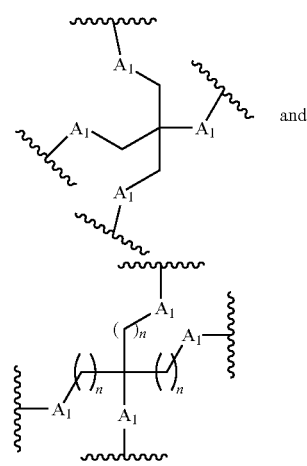

wherein each $A_1$ independently represents O, S, C=O or NH; and each n independently represents an integer from 1 to 20.

The branching unit may have a structure selected from:

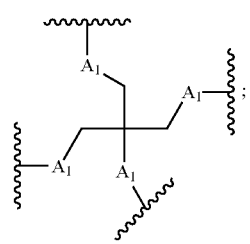

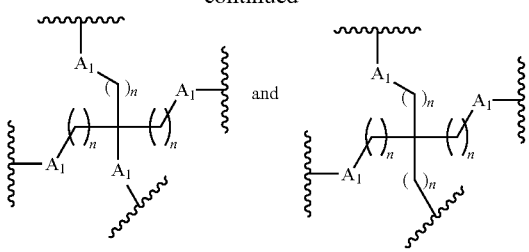

wherein each $A_1$ independently represents O, S, C=O or NH; and each n independently represents an integer from 1 to 20.

The branching unit may have a structure selected from:

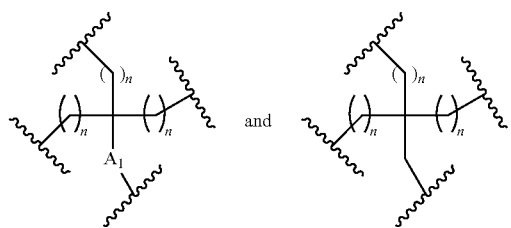

wherein $A_1$ is O, S, C=O or NH; and each n independently represents an integer from 1 to 20.

The branching unit may have the structure:

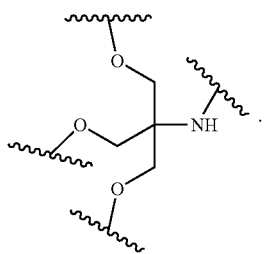 [SMILES: *NC(CO*)(CO*)CO*]

The branching unit may have the structure:

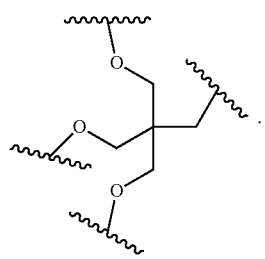 [SMILES: *CC(CO*)(CO*)CO*]

The branching unit may have the structure:

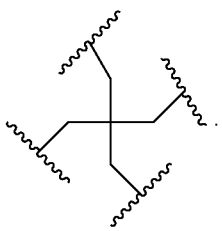 [SMILES: *CC(C*)(C*)C*]

Optionally, the branching unit consists of only a carbon atom.

The "$X^3$" portion of the compounds of formula I is a bridging unit. $X^3$ may also be referred to as the conjugate linker. The bridging unit is linear and is covalently bound to the branching unit and the nucleic acid.

$X^3$ may be selected from —$C_1$-$C_{20}$ alkylene-, —$C_2$-$C_{20}$ alkenylene-, an alkylene ether of formula —($C_1$-$C_{20}$ alkylene)-O—($C_1$-$C_{20}$ alkylene)-, —C(O)—$C_1$-$C_{20}$ alkylene-, —$C_0$-$C_4$ alkylene(Cy)$C_0$-$C_4$ alkylene- wherein Cy represents a substituted or unsubstituted 5 or 6 membered cycloalkylene, arylene, heterocyclylene or heteroarylene ring, —$C_1$-$C_4$ alkylene-NHC(O)—$C_1$-$C_4$ alkylene-, —$C_1$-$C_4$ alkylene-C(O)NH—$C_1$-$C_4$ alkylene-, —$C_1$-$C_4$ alkylene-SC(O)—$C_1$-$C_4$ alkylene-, —$C_1$-$C_4$ alkylene-C(O)S—$C_1$-$C_4$ alkylene-, —$C_1$-$C_4$ alkylene-OC(O)—$C_1$-$C_4$ alkylene-, —$C_1$-$C_4$ alkylene-C(O)O—$C_1$-$C_4$ alkylene-, and —$C_1$-$C_6$ alkylene-S—S—$C_1$-$C_6$ alkylene-.

$X^3$ may be an alkylene ether of formula —($C_1$-$C_{20}$ alkylene)-O—($C_1$-$C_{20}$ alkylene)-. $X^3$ may be an alkylene ether of formula —($C_1$-$C_{20}$ alkylene)-O—($C_4$-$C_{20}$ alkylene)-, wherein said ($C_4$-$C_{20}$ alkylene) is linked to Z. $X^3$ may be selected from the group consisting of —$CH_2$—O—$C_3H_6$—, —$CH_2$—O—$C_4H_8$—, —$CH_2$—O—$C_6H_{12}$— and —$CH_2$—O—$C_8H_{16}$—, especially —$CH_2$—O—$C_4H_8$—, —$CH_2$—O—$C_6H_{12}$— and —$CH_2$—O—$C_8H_{16}$—, wherein in each case the —$CH_2$— group is linked to A.

In a second aspect, the present invention provides compounds of formula (II):

$$[S—X^1—P—X^2]_3\text{-}A\text{-}X^3—Z \qquad (II)$$

wherein:

S represents a saccharide;

$X^1$ represents $C_3$-$C_6$ alkylene or an ethylene glycol stem (—$CH_2$—$CH_2$—O)$_m$(—$CH_2$)$_2$— wherein m is 1, 2, or 3;

P is a modified phosphate;

$X^2$ is $C_1$-$C_8$ alkylene;

A is a branching unit selected from:

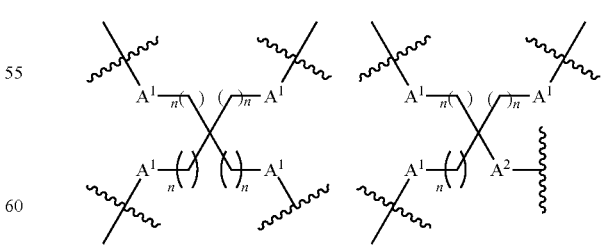

$A^1$ = O, NH
n = 1 to 4

$A^1$ = O, NH
$A^2$ = NH, $CH_2$, O
n = 1 to 4

$X^3$ is a bridging unit;
Z is a nucleic acid;
and where the linkage between $X^3$ and Z is a phosphate or thiophosphate.

Branching unit A may have the structure:

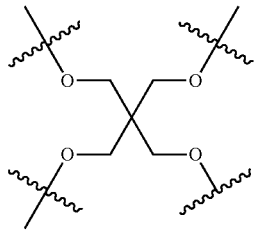

Branching unit A may have the structure:

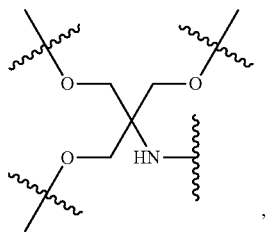

wherein $X^3$ is attached to the nitrogen atom.

$X^3$ may be $C_1$-$C_{20}$ alkylene. Preferably, $X^3$ is selected from the group consisting of —$C_3H_6$—, —$C_4H_8$—, —$C_6H_{12}$— and —$C_8H_{16}$—, especially —$C_4H_8$—, —$C_6H_{12}$— and —$C_8H_{16}$—.

In a third aspect, the present invention provides compounds of formula (III):

$$[S—X^1—P—X^2]_3\text{-}A\text{-}X^3—Z \quad (III)$$

wherein:
S represents a saccharide;
$X^1$ represents $C_3$-$C_6$ alkylene or an ethylene glycol stem (—$CH_2$—$CH_2$—$O$)$_m$(—$CH_2$)$_2$— wherein m is 1, 2, or 3;
P is a modified phosphate;
$X^2$ is an alkylene ether of formula —$C_3H_6$—$O$—$CH_2$—;
A is a branching unit;
$X^3$ is an alkylene ether of formula selected from the group consisting of —$CH_2$—$O$—$CH_2$—, —$CH_2$—$O$—$C_2H_4$—, —$CH_2$—$O$—$C_3H_6$—, —$CH_2$—$O$—$C_4H_8$—, —$CH_2$—$O$—$C_5H_{10}$—, —$CH_2$—$O$—$C_6H_{12}$—, —$CH_2$—$O$—$C_7H_{14}$—, and —$CH_2$—$O$—$C_8H_{16}$—, wherein in each case the —$CH_2$— group is linked to A,
Z is a nucleic acid;
and wherein the linkage between $X^3$ and Z is a phosphate or thiophosphate The branching unit may comprise carbon. Preferably, the carbon unit is carbon.

$X^3$ may be selected from the group consisting of —$CH_2$—$O$—$C_4H_8$—, —$CH_2$—$O$—$C_5H_{10}$—, —$CH_2$—$O$—$C_6H_{12}$—, —$CH_2$—$O$—$C_7H_{14}$—, and —$CH_2$—$O$—$C_8H_{16}$—. Preferably, $X^3$ is selected from the group consisting of —$CH_2$—$O$—$C_4H_8$—, —$CH_2$—$O$—$C_6H_{12}$— and —$CH_2$—$O$—$C_8H_{16}$.

For any of the above aspects, P represents a modified phosphate group. P can be represented by:

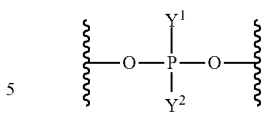

wherein $Y^1$ and $Y^2$ each independently represent =O, =S, —$O^-$, —OH, —SH, —$BH_3$, —$OCH_2CO_2$, —$OCH_2CO_2R^x$, —$OCH_2C(S)OR^x$, and —$OR^x$, wherein $R^x$ represents $C_1$-$C_6$ alkyl and wherein

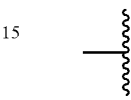

indicates attachment to the remainder of the compound.

For example, $Y^1$ may represent —OH and $Y^2$ may represent =O or =S; or $Y^1$ may represent —$O^-$ and $Y^2$ may represent =O or =S;

$Y^1$ may represent =O and $Y^2$ may represent —$CH_3$, —SH, —$OR^x$, or —$BH_3$ $Y^1$ may represent =S and $Y^2$ may represent —$CH_3$, $OR^x$ or —SH.

It will be understood by the skilled person that in certain instances there will be delocalisation between $Y^1$ and $Y^2$.

Preferably, the modified phosphate group is a thiophosphate group. Thiophosphate groups include bithiophosphate (i.e. where $Y^1$ represents =S and $Y^2$ represents —$S^-$) and monothiophosphate (i.e. where $Y^1$ represents —$O^-$ and $Y^2$ represents =S, or where $Y^1$ represents =O and $Y^2$ represents —$S^-$). Preferably, P is a monothiophosphate. The inventors have found that conjugates having thiophosphate groups in replacement of phosphate groups have improved potency and duration of action in vivo.

P may also be an ethylphosphate (i.e. where $Y^1$ represents =O and $Y^2$ represents $OCH_2CH_3$).

The saccharide, which can also be referred to as the ligand, may be selected to have an affinity for at least one type of receptor on a target cell. In particular, the receptor is on the surface of a mammalian liver cell, for example, the hepatic asialoglycoprotein receptor (ASGP-R).

For any of the above aspects, the saccharide may be selected from N-acetyl galactosamine, mannose, galactose, glucose, glucosamine and fructose. Preferably, the saccharide is N-acetyl galactosamine (GalNAc). The compounds of the invention have 3 ligands which are each preferably N-acetyl galactosamine.

"GalNAc" refers to 2-(Acetylamino)-2-deoxy-D-galactopyranose, commonly referred to in the literature as N-acetyl galactosamine. Reference to "GalNAc" or "N-acetyl galactosamine" includes both the β-form: 2-(Acetylamino)-2-deoxy-β-D-galactopyranose and the α-form: 2-(Acetylamino)-2-deoxy-α-D-galactopyranose. In certain embodiments, both the β-form: 2-(Acetylamino)-2-deoxy-β-D-galactopyranose and α-form: 2-(Acetylamino)-2-deoxy-α-D-galactopyranose may be used interchangeably. Preferably, the compounds of the invention comprise the β-form, 2-(Acetylamino)-2-deoxy-β-D-galactopyranose.

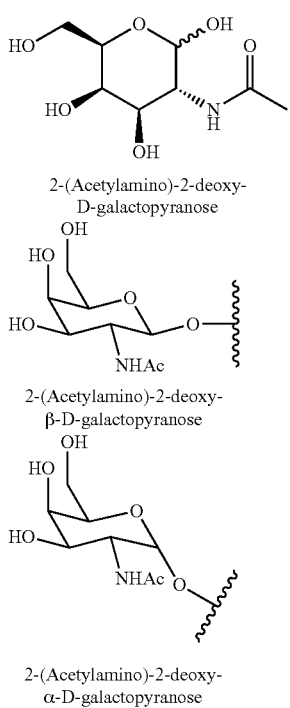

2-(Acetylamino)-2-deoxy-
D-galactopyranose 2-(Acetylamino)-2-deoxy-
β-D-galactopyranose 2-(Acetylamino)-2-deoxy-
α-D-galactopyranose The "$X^1$—P—$X^2$" portion of the compounds of the present invention may also be referred to as the tether or linker. The linker comprises a linear group and is covalently attached to the saccharide ligand and the branching unit.

For any of the above aspects, $X^1$ may be an ethylene glycol stem (—CH$_2$—CH$_2$—O)$_m$(—CH$_2$)$_2$— wherein m is 1, 2, or 3. $X^1$ may be (—CH$_2$—CH$_2$—O)(—CH$_2$)$_2$—. $X^1$ may be (—CH$_2$—CH$_2$—O)$_2$(—CH$_2$)$_2$—. $X^1$ may be (—CH$_2$—CH$_2$—O)$_3$(—CH$_2$)$_2$—. Preferably, $X^1$ is (—CH$_2$—CH$_2$—O)$_2$(—CH$_2$)$_2$—. Alternatively, $X^1$ represents C$_3$-C$_6$ alkylene. $X^1$ may be propylene. $X^1$ may be butylene. $X^1$ may be pentylene. $X^1$ may be hexylene. Preferably the alkyl is a linear alkylene. In particular, $X^1$ may be butylene.

For compounds of the third aspect, $X^2$ represents an alkylene ether of formula —C$_3$H$_6$—O—CH$_2$— i.e. C$_3$ alkoxy methylene, or —CH$_2$CH$_2$CH$_2$OCH$_2$—.

In a fourth aspect, the present invention provides conjugate compounds having the structure:

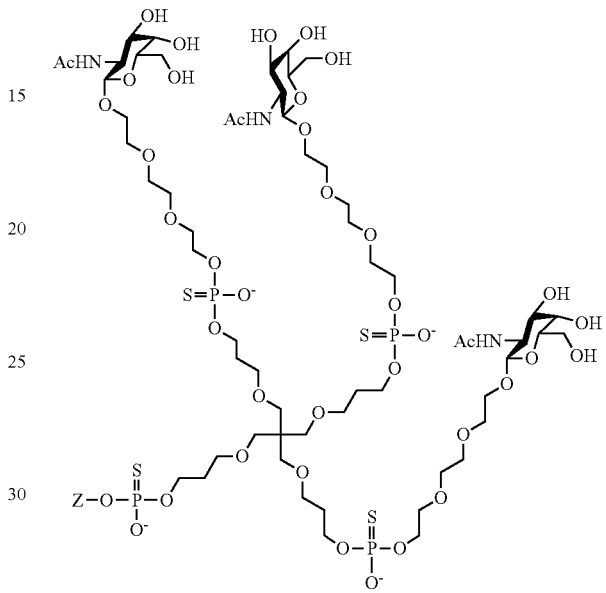

wherein Z is a nucleic acid.

In a fifth aspect, the present invention provides conjugate compounds having the structure:

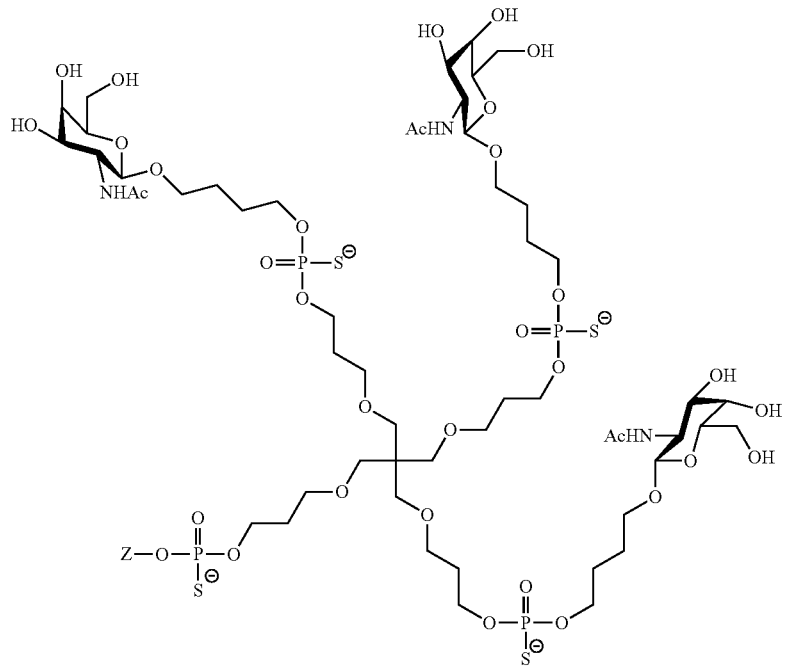

wherein Z is a nucleic acid.

In a sixth aspect, the present invention provides conjugate compounds having the structure:
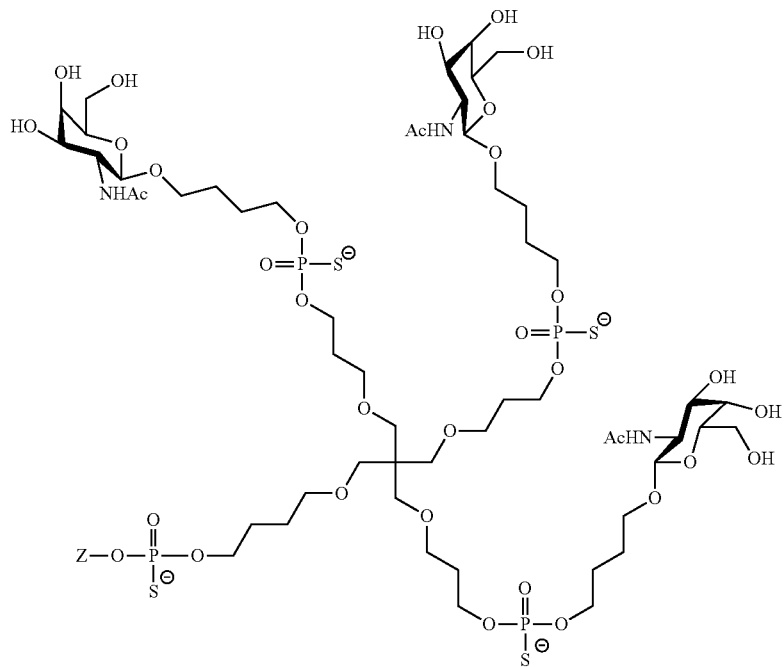
wherein Z is a nucleic acid.
In a seventh aspect, the present invention provides conjugate compounds having the structure:
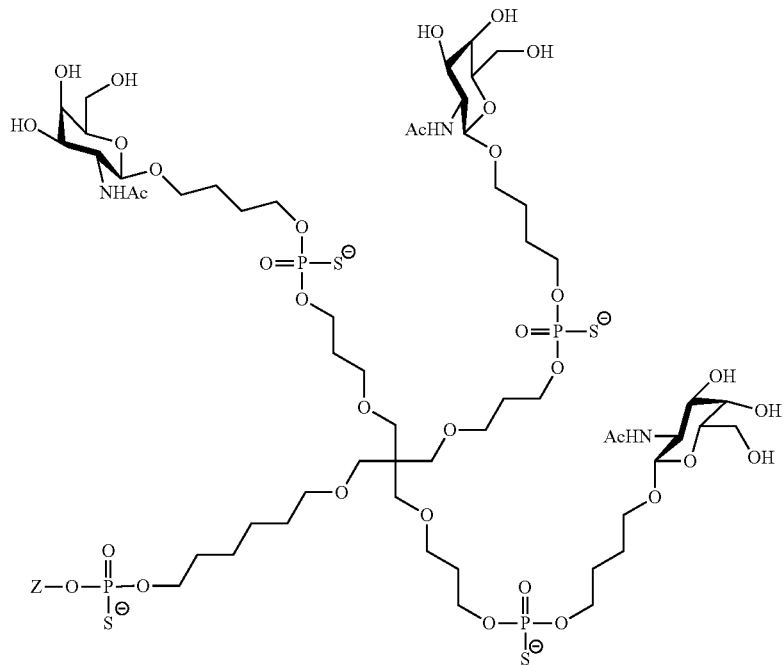
wherein Z is a nucleic acid.

In an eighth aspect, the present invention provides conjugate compounds having the structure:
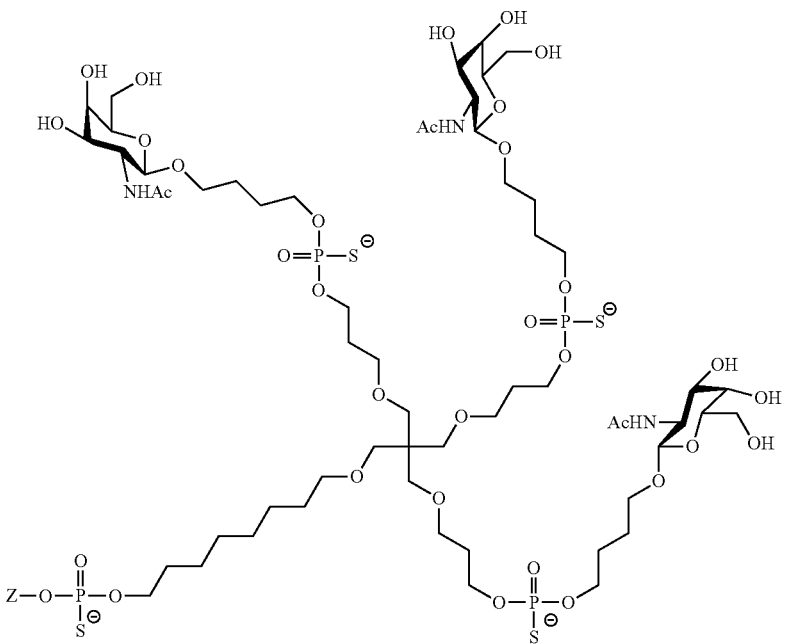
wherein Z is a nucleic acid.
In a ninth aspect, the present invention provides conjugate compounds having the structure:
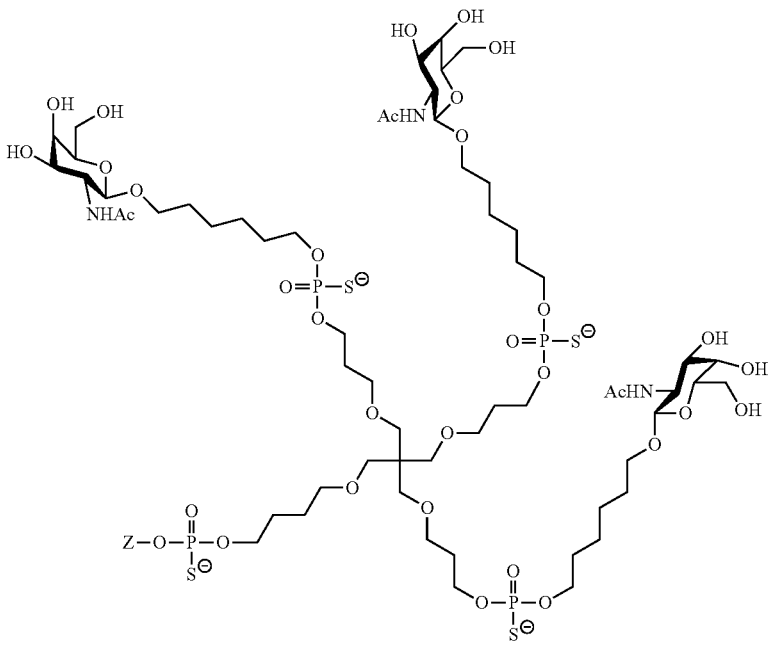
wherein Z is a nucleic acid.

In a tenth aspect, the present invention provides conjugate compounds having the structure:
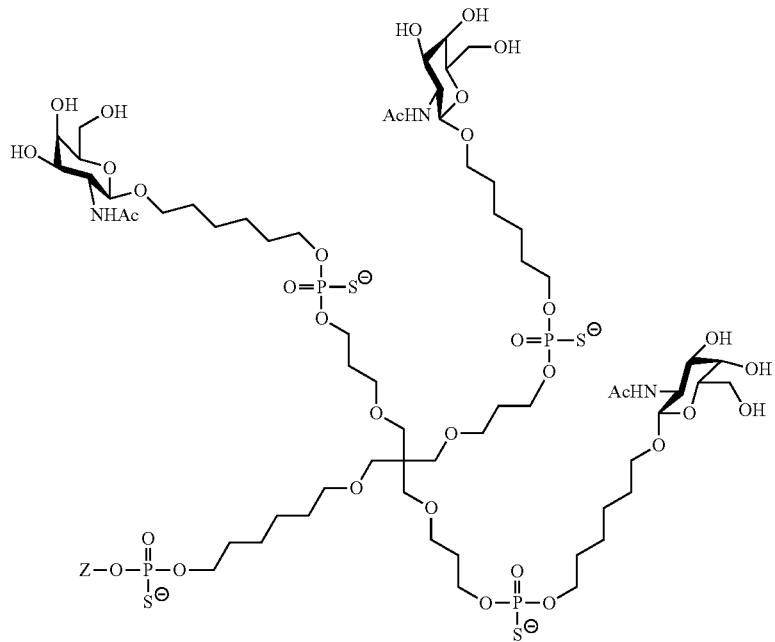
wherein Z is a nucleic acid.
In an eleventh aspect, the present invention provides conjugate compounds having the structure:
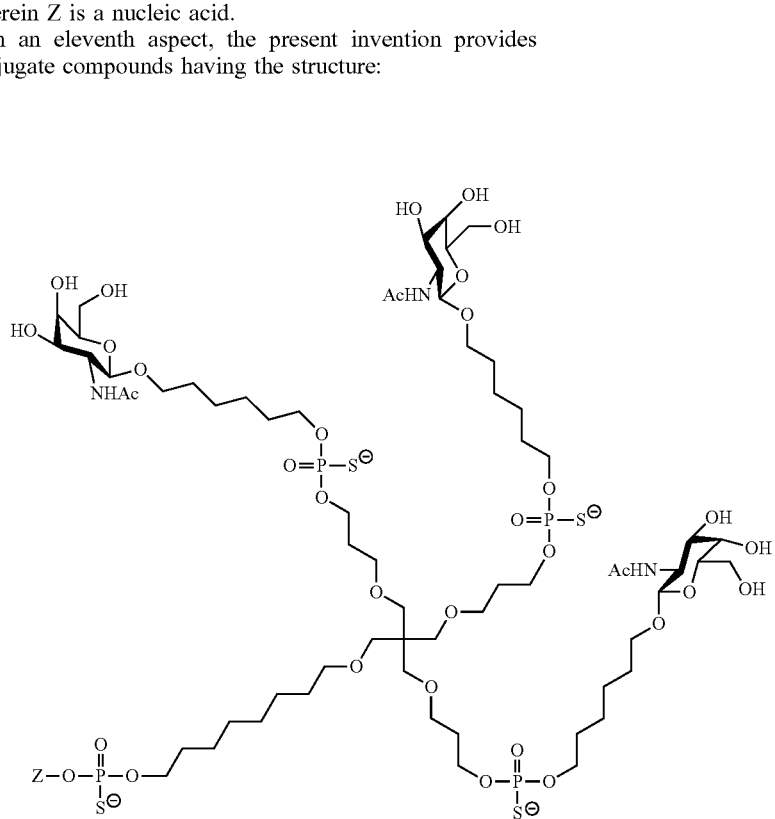
wherein Z is a nucleic acid.

In all cases described herein, the nucleic acid may be selected from the group consisting of DNA, RNA, PNA and LNA.

The nucleic acid may be a functional nucleic acid, whereby preferably the functional nucleic acid is selected from the group consisting of mRNA, micro-RNA, shRNA, combinations of RNA and DNA, siRNA, siNA, antisense nucleic acid, ribozymes, aptamers and spiegelmers. In particular, the nucleic acid may be siRNA.

The nucleic acid may be selected from RNAi, siRNA, antisense nucleic acid, ribozymes, aptamers and spiegelmers.

The nucleic acids may be of any length and can have any number of nucleotides such that they are effective for RNAi. Preferably, the siRNAs range from 15 to 30 nucleotides. The duplex region of a double stranded RNA may range from 15 to 30 nucleotide base pairs using the Watson-crick base pairing. The duplex region may have 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 base pairs.

Preferably, the nucleic acid has 19 to 23 base pairs. For example, the nucleic acid may be 19, 20, 21, 22 or 23 base pairs in length.

The double stranded iRNAs may be blunt ended at one end or on both ends. The double stranded iRNAs may have overhangs of 1 or more nucleotides one or both strands at one or both ends. The overhangs may be 1, 2, 3, 4, 5, 6, 7, 8, 9, or 10 nucleotides n length.

For any of the above aspects, the nucleic acid may be a modified nucleic acid. The modification may be selected from substitutions or insertions with analogues of nucleic acids or bases and chemical modification of the base, sugar or phosphate moieties.

The nucleic acid may: a) be blunt ended at both ends; b) have an overhang at one end and a blunt end at the other; or c) have an overhang at both ends.

One or more nucleotides on the first and/or second strand may be modified, to form modified nucleotides. One or more of the odd numbered nucleotides of the first strand may be modified. One or more of the even numbered nucleotides of the first strand may be modified by at least a second modification, wherein the at least second modification is different from the modification on the one or more add nucleotides. At least one of the one or more modified even numbered nucleotides may be adjacent to at least one of the one or more modified odd numbered nucleotides.

A plurality of odd numbered nucleotides in the first strand may be modified in the nucleic acid of the invention. A plurality of even numbered nucleotides in the first strand may be modified by a second modification. The first strand may comprise adjacent nucleotides that are modified by a common modification. The first strand may also comprise adjacent nucleotides that are modified by a second different modification.

One or more of the odd numbered nucleotides of the second strand may be modified by a modification that is different to the modification of the odd numbered nucleotides on the first strand and/or one or more of the even numbered nucleotides of the second strand may be by the same modification of the odd numbered nucleotides of the first strand. At least one of the one or more modified even numbered nucleotides of the second strand may be adjacent to the one or more modified odd numbered nucleotides. A plurality of odd numbered nucleotides of the second strand may be modified by a common modification and/or a plurality of even numbered nucleotides may be modified by the same modification that is present on the first strand odd numbered nucleotides. A plurality of odd numbered nucleotides on the second strand may be modified by a second modification, wherein the second modification is different from the modification of the first strand odd numbered nucleotides.

The second strand comprises adjacent nucleotides that are modified by a common modification, which may be a second modification that is different from the modification of the odd numbered nucleotides of the first strand.

In the nucleic acid of the invention, each of the odd numbered nucleotides in the first strand and each of the even numbered nucleotides in the second strand may be modified with a common modification and, each of the even numbered nucleotides may be modified in the first strand with a second modification and each of the odd numbered nucleotides may be modified in the second strand with a second different modification.

The nucleic acid of the invention may have the modified nucleotides of the first strand shifted by at least one nucleotide relative to the unmodified or differently modified nucleotides of the second strand.

The modification and/or modifications may each and individually be selected from the group consisting of 3' terminal deoxy thymine, 2' O methyl, a 2' deoxy modification, a 2' amino modification, a 2' alkyl modification, a morpholino modification, a phosphoramidate modification, 5'-phosphorothioate group modification, a 5' phosphate or 5' phosphate mimic modification and a cholesteryl derivative or a dodecanoic acid bisdecylamide group modification and/or the modified nucleotide may be any one of a locked nucleotide, an abasic nucleotide or a non natural base comprising nucleotide. At least one modification may be 2'-O-methyl and/or at least one modification may be 2'-F.

By nucleic acid it is meant a nucleic acid comprising two strands comprising nucleotides, that is able to interfere with gene expression. Inhibition may be complete or partial and results in down regulation of gene expression in a targeted manner. The nucleic acid comprises two separate polynucleotide strands; the first strand, which may also be a guide strand; and a second strand, which may also be a passenger strand. The first strand and the second strand may be part of the same polynucleotide molecule that is self complementary which 'folds' to form a double stranded molecule. The nucleic acid may be an siRNA molecule.

The first strand may also be referred to as an antisense strand. The second strand may also be referred to as a sense strand.

The nucleic acid may comprise ribonucleotides, modified ribonucleotides, deoxynucleotides, deoxyribonucleotides, or nucleotide analogous. The nucleic acid may further comprise a double stranded nucleic acid portion or duplex region formed by all or a portion of the first strand (also known in the art as a guide strand) and all or a portion of the second strand (also known in the art as a passenger strand). The duplex region is defined as beginning with the first base pair formed between the first strand and the second strand and ending with the last base pair formed between the first strand and the second strand, inclusive.

By duplex region refers it is meant the region in two complementary or substantially complementary oligonucleotides that form base pairs with one another, either by Watson-Crick base pairing or any other manner that allows for a duplex between oligonucleotide strands that are complementary or substantially complementary. For example, an oligonucleotide strand having 21 nucleotide units can base pair with another oligonucleotide of 21 nucleotide units, yet only 19 nucleotides on each strand are complementary or substantially complementary, such that the "duplex region" consists of 19 base pairs. The remaining base pairs may exist as 5' and 3' overhangs, or as single stranded regions. Further, within the duplex region, 100% complementarity is not required; substantial complementarity is allowable within a duplex region. Substantial complementarity refers to complementarity between the strands such that they are capable of annealing under biological conditions. Techniques to empirically determine if two strands are capable of annealing under biological conditions are well known in the art. Alternatively, two strands can be synthesised and added together under biological conditions to determine if they anneal to one another.

The portion of the first strand and second strand that form at least one duplex region may be fully complementary and are at least partially complementary to each other.

Depending on the length of an nucleic acid, a perfect match in terms of base complementarity between the first strand and second strand is not necessarily required. However, the first and second strands must be able to hybridise under physiological conditions.

The complementarity between the first strand and second strand in the at least one duplex region may be perfect in that there are no nucleotide mismatches or additional/deleted nucleotides in either strand. Alternatively, the complementarity may not be perfect. The complementarity may be at least 70%, 75%, 80%, 85%, 90% or 95%.

The first strand and the second strand may each comprise a region of complementarity which comprises at least 15 contiguous nucleotides differing by no more than 3 nucleotides.

An "overhang" as used herein has its normal and customary meaning in the art, i.e. a single stranded portion of a nucleic acid that extends beyond the terminal nucleotide of a complementary strand in a double strand nucleic acid. The term "blunt end" includes double stranded nucleic acid whereby both strands terminate at the same position, regardless of whether the terminal nucleotide(s) are base paired. The terminal nucleotide of a first strand and a second strand at a blunt end may be base paired. The terminal nucleotide of a first strand and a second strand at a blunt end may not be paired. The terminal two nucleotides of an first strand and a second strand at a blunt end may be base paired. The terminal two nucleotides of an first strand and a second strand at a blunt end may not be paired.

The nucleic acid may have an overhang at one end and a blunt end at the other. The nucleic acid may have an overhang at both ends. The nucleic acid may be blunt ended at both ends. The nucleic acid may be blunt ended at the end with the 5' end of the first strand and the 3' end of the second strand or at the 3'-end of the first strand and the 5' end of the second strand.

The nucleic acid may comprise an overhang at a 3' or 5' end. The nucleic acid may have a 3' overhang on the first strand. The nucleic acid may have a 3' overhang on the second strand. The nucleic acid may have a 5' overhang on the first strand. The nucleic acid may have a 5' overhang on the second strand. The nucleic acid may have an overhang at both the 5' end and 3' end of the first strand. The nucleic acid may have an overhang at both the 5' end and 3' end of the second strand. The nucleic acid may have a 5' overhang on the first strand and a 3' overhang on the second strand. The nucleic acid may have a 3' overhang on the first strand and a 5' overhang on the second strand. The nucleic acid may have a 3' overhang on the first strand and a 3' overhang on the second strand. The nucleic acid may have a 5' overhang on the first strand and a 5' overhang on the second strand.

An overhang at the 3'-end or 5' end of the second strand or the first strand may be selected from consisting of 1, 2, 3, 4 and 5 nucleotides in length. Optionally, an overhang may consist of 1 or 2 nucleotides, which may or may not be modified.

Unmodified polynucleotides, particularly ribonucleotides, may be prone to degradation by cellular nucleases, and, as such, modification/modified nucleotides may be included in the nucleic acid of the invention.

One or more nucleotides on the second and/or first strand of the nucleic acid of the invention may be modified.

Modifications of the nucleic acid of the present invention generally provide a powerful tool in overcoming potential limitations including, but not limited to, in vitro and in vivo stability and bioavailability inherent to native RNA molecules. The nucleic acid according to the invention may be modified by chemical modifications. Modified nucleic acid can also minimise the possibility of inducing interferon activity in humans. Modification can further enhance the functional delivery of a nucleic acid to a target cell. The modified nucleic acid of the present invention may comprise one or more chemically modified ribonucleotides of either or both of the first strand or the second strand. A ribonucleotide may comprise a chemical modification of the base, sugar or phosphate moieties. The ribonucleic acid may be modified by substitution or insertion with analogues of nucleic acids or bases.

One or more nucleotides of a nucleic acid of the present invention may be modified. The nucleic acid may comprise at least one modified nucleotide. The modified nucleotide may be on the first strand. The modified nucleotide may be in the second strand. The modified nucleotide may be in the duplex region. The modified nucleotide may be outside the duplex region, i.e., in a single stranded region. The modified nucleotide may be on the first strand and may be outside the duplex region. The modified nucleotide may be on the second strand and may be outside the duplex region. The 3'-terminal nucleotide of the first strand may be a modified nucleotide. The 3'-terminal nucleotide of the second strand may be a modified nucleotide. The 5'-terminal nucleotide of the first strand may be a modified nucleotide. The 5'-terminal nucleotide of the second strand may be a modified nucleotide.

An nucleic acid of the invention may have 1 modified nucleotide or a nucleic acid of the invention may have about 2-4 modified nucleotides, or a nucleic acid may have about 4-6 modified nucleotides, about 6-8 modified nucleotides, about 8-10 modified nucleotides, about 10-12 modified nucleotides, about 12-14 modified nucleotides, about 14-16 modified nucleotides about 16-18 modified nucleotides, about 18-20 modified nucleotides, about 20-22 modified nucleotides, about 22-24 modified nucleotides, 24-26 modified nucleotides or about 26-28 modified nucleotides. In each case the nucleic acid comprising said modified nucleotides retains at least 50% of its activity as compared to the same nucleic acid but without said modified nucleotides. The nucleic acid may retain 55%, 60%, 65%, 70%, 75%, 80%, 85%, 90%, 95% or 100% or above of its activity as compared to the same nucleic acid but without said modified nucleotides The modified nucleotide may be a purine or a pyrimidine. At least half of the purines may be modified. At least half of the pyrimidines may be modified. All of the purines may be modified. All of the pyrimidines may be modified. The modified nucleotides may be selected from the group consisting of a 3' terminal deoxy thymine (dT) nucleotide, a 2' O methyl modified nucleotide, a 2' modified nucleotide, a 2' deoxy modified nucleotide, a locked nucleotide, an abasic nucleotide, a 2' amino modified nucleotide, a 2' alkyl modified nucleotide, a morpholino nucleotide, a phosphoramidate, a non natural base comprising nucleotide, a nucleotide comprising a 5'-phosphorothioate group, a nucleotide comprising a 5' phosphate or 5' phosphate mimic and a terminal nucleotide linked to a cholesteryl derivative or a dodecanoic acid bisdecylamide group.

The nucleic acid may comprise a nucleotide comprising a modified nucleotide, wherein the base is selected from 2-aminoadenosine, 2,6-diaminopurine,inosine, pyridin-4-one, pyridin-2-one, phenyl, pseudouracil, 2,4,6-trimethoxy benzene, 3-methyl uracil, dihydrouridine, naphthyl, aminophenyl, 5-alkylcytidine (e.g., 5-methylcytidine), 5-alkyluridine (e.g., ribothymidine), 5-halouridine (e.g., 5-bromouridine), 6-azapyrimidine, 6-alkylpyrimidine (e.g. 6-methyluridine), propyne, quesosine, 2-thiouridine, 4-thiouridine, wybutosine, wybutoxosine, 4-acetylcytidine, 5-(carboxyhydroxymethyl)uridine, 5'-carboxymethylaminomethyl-2-thiouridine, 5-carboxymethylaminomethyluridine, beta-D-glalactosylqueosine, 1-methyladenosine, 1-methylinosine, 2,2-dimethylguanosine, 3-methylcytidine, 2-methyladenosine, 2-methylguanosine, N6-methyladenosine, 7-methylguanosine, 5-methoxyaminomethyl-2-thiouridine, 5-methylaminomethyluridine, 5-methylcarbonylmethyluridine, 5-methyloxyuridine, 5-methyl-2-thiouridine, 2-methylthio-N6-isopentenyladenosine, beta-D-mannosylqueosine, uridine-5-oxyacetic acid and 2-thiocytidine.

Nucleic acids discussed herein include unmodified RNA as well as RNA which have been modified, e.g., to improve efficacy, and polymers of nucleoside surrogates. Unmodified RNA refers to a molecule in which the components of the nucleic acid, namely sugars, bases, and phosphate moieties, are the same or essentially the same as that which occur in nature, for example as occur naturally in the human body. Modified nucleotide as used herein refers to a nucleotide in which one or more of the components of the nucleic acid, namely sugars, bases, and phosphate moieties, are different from that which occur in nature. While they are referred to as modified nucleotides they will of course, because of the modification, include molecules which are not nucleotides, for example a polynucleotide molecules in which the ribo-phosphate backbone is replaced with a non-ribophosphate construct that allows hybridisation between strands i.e. the modified nucleotides mimic the ribophosphate backbone.

Many of the modifications described below that occur within a nucleic acid will be repeated within a polynucleotide molecule, such as a modification of a base, or a phosphate moiety, or the a non-linking O of a phosphate moiety. In some cases the modification will occur at all of the possible positions/nucleotides in the polynucleotide but in many cases it will not. A modification may only occur at a 3' or 5' terminal position, may only occur in a terminal regions, such as at a position on a terminal nucleotide or in the last 2, 3, 4, 5, or 10 nucleotides of a strand. A modification may occur in a double strand region, a single strand region, or in both. A modification may occur only in the double strand region of an nucleic acid of the invention or may only occur in a single strand region of an nucleic acid of the invention. A phosphorothioate modification at a non-linking O position may only occur at one or both termini, may only occur in a terminal region, e.g., at a position on a terminal nucleotide or in the last 2, 3, 4 or 5 nucleotides of a strand, or may occur in duplex and/or in single strand regions, particularly at termini. The 5' end or 3' ends may be phosphorylated.

Stability of an nucleic acid of the invention may be increased by including particular bases in overhangs, or to include modified nucleotides, in single strand overhangs, e.g., in a 5' or 3' overhang, or in both. Purine nucleotides may be included in overhangs. All or some of the bases in a 3' or 5' overhang may be modified. Modifications can include the use of modifications at the 2' OH group of the ribose sugar, the use of deoxyribonucleotides, instead of ribonucleotides, and modifications in the phosphate group, such as phosphothioate modifications. Overhangs need not be homologous with the target sequence.

Nucleases can hydrolyze nucleic acid phosphodiester bonds. However, chemical modifications to nucleic acids can confer improved properties, and, can render oligoribonucleotides more stable to nucleases.

Modified nucleic acids, as used herein, can include one or more of:

(i) alteration, e.g., replacement, of one or both of the non-linking phosphate oxygens and/or of one or more of the linking phosphate oxygens (referred to as linking even if at the 5' and 3' terminus of the nucleic acid of the invention);

(ii) alteration, e.g., replacement, of a constituent of the ribose sugar, e.g., of the 2' hydroxyl on the ribose sugar;

(iii) replacement of the phosphate moiety with "dephospho" linkers;

(iv) modification or replacement of a naturally occurring base;

(v) replacement or modification of the ribose-phosphate backbone;

(vi) modification of the 3' end or 5' end of the RNA, e.g., removal, modification or replacement of a terminal phosphate group or conjugation of a moiety, e.g., a fluorescently labeled moiety, to either the 3' or 5' end of RNA.

The terms replacement, modification, alteration, indicates a difference from a naturally occurring molecule.

Specific modifications are discussed in more detail below.

Examples of modified phosphate groups include phosphorothioate, phosphoroselenates, borano phosphates, borano phosphate esters, hydrogen phosphonates, phosphoroamidates, alkyl or aryl phosphonates and phosphotriesters. Phosphorodithioates have both non-linking oxygens replaced by sulphur. One, each or both non-linking oxygens in the phosphate group can be independently any one of S, Se, B, C, H, N, or OR (R is alkyl or aryl).

The phosphate linker can also be modified by replacement of a linking oxygen with nitrogen (bridged phosphoroamidates), sulfur (bridged phosphorothioates) and carbon (bridged methylenephosphonates). The replacement can occur at a terminal oxygen. Replacement of the non-linking oxygens with nitrogen is possible.

A modified nucleotide can include modification of the sugar groups. The 2' hydroxyl group (OH) can be modified or replaced with a number of different "oxy" or "deoxy" substituents.

Examples of "oxy"-2' hydroxyl group modifications include alkoxy or aryloxy (OR, e.g., R=H, alkyl, cycloalkyl, aryl, aralkyl, heteroaryl or sugar); polyethyleneglycols (PEG), O(CH2CH2O)nCH2CH2OR; "locked" nucleic acids (LNA) in which the 2' hydroxyl is connected, e.g., by a methylene bridge, to the 4' carbon of the same ribose sugar; O-AMINE (AMINE=NH2; alkylamino, dialkylamino, heterocyclyl, arylamino, diaryl amino, heteroaryl amino, or diheteroaryl amino, ethylene diamine, polyamino) and aminoalkoxy, O(CH2)nAMINE, (e.g., AMINE=NH2; alkylamino, dialkylamino, heterocyclyl, arylamino, diaryl amino, heteroaryl amino, or diheteroaryl amino, ethylene diamine, polyamino).

"Deoxy" modifications include hydrogen halo; amino (e.g., NH2; alkylamino, dialkylamino, heterocyclyl, arylamino, diaryl amino, heteroaryl amino, diheteroaryl amino, or amino acid); NH(CH2CH2NH)nCH2CH2-AMINE (AMINE=NH2; alkylamino, dialkylamino, heterocyclyl, arylamino, diaryl amino, heteroaryl amino, or diheteroaryl amino), —NHC(O)R (R=alkyl, cycloalkyl, aryl, aralkyl, heteroaryl or sugar), cyano; mercapto; alkyl-thio-alkyl; thioalkoxy; and alkyl, cycloalkyl, aryl, alkenyl and alkynyl, which may be optionally substituted with e.g., an amino functionality. Other substitutents of certain embodiments include 2'-methoxyethyl, 2'-OCH3, 2'-O-allyl, 2'-C-allyl, and 2'-fluoro.

The sugar group can also contain one or more carbons that possess the opposite stereochemical configuration than that of the corresponding carbon in ribose. Thus, a modified nucleotides may contain a sugar such as arabinose.

Modified nucleotides can also include "abasic" sugars, which lack a nucleobase at C—I'. These abasic sugars can further contain modifications at one or more of the constituent sugar atoms.

The 2' modifications may be used in combination with one or more phosphate linker modifications (e.g., phosphorothioate).

The phosphate group can be replaced by non-phosphorus containing connectors.

Examples of moieties which can replace the phosphate group include siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo and methyleneoxymethylimino. In certain embodiments, replacements may include the methylenecarbonylamino and methylenemethylimino groups.

The phosphate linker and ribose sugar may be replaced by nuclease resistant nucleotides.

Examples include the mophilino, cyclobutyl, pyrrolidine and peptide nucleic acid (PNA) nucleoside surrogates. In certain embodiments, PNA surrogates may be used.

The 3' and 5' ends of an oligonucleotide can be modified. Such modifications can be at the 3' end or the 5' end or both ends of the molecule. They can include modification or replacement of an entire terminal phosphate or of one or more of the atoms of the phosphate group. For example, the 3' and 5' ends of an oligonucleotide can be conjugated to other functional molecular entities such as labeling moieties, e.g., fluorophores (e.g., pyrene, TAMRA, fluorescein, Cy3 or Cy5 dyes) or protecting groups (based e.g., on sulfur, silicon, boron or ester). The functional molecular entities can be attached to the sugar through a phosphate group and/or a linker. The terminal atom of the linker can connect to or replace the linking atom of the phosphate group or the C-3' or C-5' O, N, S or C group of the sugar. Alternatively, the linker can connect to or replace the terminal atom of a nucleotide surrogate (e.g., PNAs). These spacers or linkers can include e.g., —(CH2)n-, —(CH2)nN—, —(CH2)nO—, —(CH2)nS—, O(CH2CH2O)nCH2CH2OH (e.g., n=3 or 6), abasic sugars, amide, carboxy, amine, oxyamine, oxyimine, thioether, disulfide, thiourea, sulfonamide, or morpholino, or biotin and fluorescein reagents. The 3' end can be an —OH group.

Other examples of terminal modifications include dyes, intercalating agents (e.g., acridines), cross-linkers (e.g., psoralene, mitomycin C), porphyrins (TPPC4, texaphyrin, Sapphyrin), polycyclic aromatic hydrocarbons (e.g., phenazine, dihydrophenazine), artificial endonucleases (e.g., EDTA), lipophilic carriers (e.g., cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl) lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]2, polyamino, alkyl, substituted alkyl, radiolabeled markers, enzymes, haptens (e.g., biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles).

Terminal modifications can be added for a number of reasons, including to modulate activity or to modulate resistance to degradation. Terminal modifications useful for modulating activity include modification of the 5' end with phosphate or phosphate analogs. Nucleic acids of the invention, on the first or second strand, may be 5' phosphorylated or include a phosphoryl analog at the 5' prime terminus. 5'-phosphate modifications include those which are compatible with RISC mediated gene silencing. Suitable modifications include: 5'-monophosphate ((HO)2(O)P—O-5'); 5'-diphosphate ((HO)2(O)P—O—P(HO)(O)—O-5'); 5'-triphosphate ((HO)2(O)P—O—(HO)(O)P—O—P(HO)(O)—O-5'); 5'-guanosine cap (7-methylated or non-methylated) (7m-G-O -5'-(HO)(O)P—O—(HO)(O)P—O—P(HO)(O)—O—O-5'); 5'-adenosine cap (Appp), and any modified or unmodified nucleotide cap structure (N—O-5'-(HO)(O)P—O—(HO)(O)P—O—P(HO)(O)—O-5'); 5'-monothiophosphate (phosphorothioate; (HO)2(S)P—O-5'); 5'-monodithiophosphate (phosphorodithioate; (HO)(HS)(S)P—O-5'), 5'-phosphorothiolate ((HO)2(O)P—S-5'); any additional combination of oxygen/sulfur replaced monophosphate, diphosphate and triphosphates (e.g., 5'-alpha-thiotriphosphate, 5'-gamma-thiotriphosphate, etc.), 5'-phosphoramidates ((HO)2(O)P—NH-5', (HO)(NH2)(O)P—O-5'), 5'-alkylphosphonates (R=alkyl=methyl, ethyl, isopropyl, propyl, etc., e.g., RP(OH)(O)—O-5'-, (OH)2(O)P-5'-CH2-), 5'vinylphosphonate, 5'-alkyletherphosphonates (R=alkylether=methoxymethyl (MeOCH2-), ethoxymethyl, etc., e.g., RP(OH)(O)—O-5'-).

The nucleic acid of the present invention may include one or more phosphorothioate modifications on one or more of the terminal ends of the first and/or the second strand. Optionally, each or either end of the first strand may comprise one or two or three phosphorothioate modified nucleotides. Optionally, each or either end of the second strand may comprise one or two or three phosphorothioate modified nucleotides. Optionally, both ends of the first strand and the 5' end of the second strand may comprise two phosphorothioate modified nucleotides. By phosphorothioate modified nucleotide it is meant that the linkage between the nucleotide and the adjacent nucleotide comprises a phosphorothioate group instead of a standard phosphate group.

Terminal modifications can also be useful for monitoring distribution, and in such cases the groups to be added may include fluorophores, e.g., fluorscein or an Alexa dye. Terminal modifications can also be useful for enhancing uptake, useful modifications for this include cholesterol. Terminal modifications can also be useful for cross-linking an RNA agent to another moiety.

Adenine, guanine, cytosine and uracil are the most common bases found in RNA. These bases can be modified or replaced to provide RNA's having improved properties. E.g., nuclease resistant oligoribonucleotides can be prepared with these bases or with synthetic and natural nucleobases (e.g., inosine, thymine, xanthine, hypoxanthine, nubularine, isoguanisine, or tubercidine) and any one of the above modifications. Alternatively, substituted or modified analogs of any of the above bases and "universal bases" can be employed. Examples include 2-aminoadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 5-halouracil, 5-(2-aminopropyl)uracil, 5-amino allyl uracil, 8-halo, amino, thiol, thioalkyl, hydroxyl and other 8-substituted adenines and guanines, 5-trifluoromethyl and other 5-substituted uracils and cytosines, 7-methylguanine, 5-substituted pyrimidines, 6-azapyrimidines and N-2, N-6 and O-6 substituted purines, including 2-aminopropyladenine, 5-propynyluracil and 5-propynylcytosine, dihydrouracil, 3-deaza-5-azacytosine, 2-aminopurine, 5-alkyluracil, 7-alkylguanine, 5-alkyl cytosine, 7-deazaadenine, N6,N6-dimethyladenine, 2,6-diaminopurine, 5-amino-allyl-uracil, N3-methyluracil, substituted 1,2,4-triazoles, 2-pyridinone, 5-nitroindole, 3-nitropyrrole, 5-methoxyuracil, uracil-5-oxyacetic acid, 5-methoxycarbonylmethyluracil, 5-methyl-2-thiouracil, 5-methoxycarbonylmethyl-2-thiouracil, 5-methylaminomethyl-2-thiouracil, 3-(3-amino-3-carboxypropyl)uracil, 3-methylcytosine, 5-methylcytosine, N<4>-acetyl cytosine, 2-thiocytosine, N6-methyladenine, N6-isopentyladenine, 2-methylthio-N6-isopentenyladenine, N-methylguanines, or O-alkylated bases.

As used herein, the terms "non-pairing nucleotide analog" means a nucleotide analog which includes a non-base pairing moiety including but not limited to: 6 des amino adenosine (Nebularine), 4-Me-indole, 3-nitropyrrole, 5-nitroindole, Ds, Pa, N3-Me ribo U, N3-Me riboT, N3-Me dC, N3-Me-dT, N1-Me-dG, N1-Me-dA, N3-ethyl-dC, N3-Me dC. In some embodiments the non-base pairing nucleotide analog is a ribonucleotide. In other embodiments it is a deoxyribonucleotide.

As used herein, the term, "terminal functional group" includes without limitation a halogen, alcohol, amine, carboxylic, ester, amide, aldehyde, ketone, ether groups.

Certain moieties may be linked to the 5' terminus of the first strand or the second strand and includes abasic ribose moiety, abasic deoxyribose moiety, modifications abasic ribose and abasic deoxyribose moieties including 2' O alkyl modifications; inverted abasic ribose and abasic deoxyribose moieties and modifications thereof, C6-imino-Pi; a mirror nucleotide including L-DNA and L-RNA; 5'OMe nucleotide; and nucleotide analogs including 4',5'-methylene nucleotide; 1-(β-D-erythrofuranosyl)nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 12-aminododecyl phosphate; hydroxypropyl phosphate; 1,5-anhydrohexitol nucleotide; alpha-nucleotide; threo-pentofuranosyl nucleotide; acyclic 3',4'-seco nucleotide; 3,4-dihydroxybutyl nucleotide; 3,5-dihydroxypentyl nucleotide, 5'-5'-inverted abasic moiety; 1,4-butanediol phosphate; 5'-amino; and bridging or non bridging methylphosphonate and 5'-mercapto moieties.

The nucleic acids of the invention may be included one or more inverted nucleotides, for example inverted thymidine or inverted adenine (for example see Takei, et al., 2002. JBC 277 (26):23800-06).

As used herein, the term "inhibit", "down-regulate", or "reduce" with respect to gene expression means the expression of the gene, or level of RNA molecules or equivalent RNA molecules encoding one or more proteins or protein subunits (e.g., mRNA), or activity of one or more proteins or protein subunits, is reduced below that observed in the absence of a nucleic acid of the invention; for example the expression may be reduced to 90%, 80%, 70%, 60%, 50%, 40%, 30%, 20%, 10%, 5% or less than that observed in the absence of an inhibitor.

The nucleic acid of the present invention may comprise an abasic nucleotide. The term "abasic" as used herein, refers to moieties lacking a base or having other chemical groups in place of a base at the 1' position, for example a 3',3'-linked or 5',5'-linked deoxyabasic ribose derivative.

The nucleic acid may comprise one or more nucleotides on the second and/or first strands that are modified. Alternating nucleotides may be modified, to form modified nucleotides.

Alternating as described herein means to occur one after another in a regular way. In other words, alternating means to occur in turn repeatedly. For example if one nucleotide is modified, the next contiguous nucleotide is not modified and the following contiguous nucleotide is modified and so on. One nucleotide may be modified with a first modification, the next contiguous nucleotide may be modified with a second modification and the following contiguous nucleotide is modified with the first modification and so on, where the first and second modifications are different.

One or more of the odd numbered nucleotides of the first strand of the nucleic acid of the invention may be modified wherein the first strand is numbered 5' to 3'. The term "odd numbered" as described herein means a number not divisible by two. Examples of odd numbers are 1, 3, 5, 7, 9, 11 and so on. One or more of the even numbered nucleotides of the first strand of the nucleic acid of the invention may be modified, wherein the first strand is numbered 5' to 3'. The term "even numbered" as described herein means a number which is evenly divisible by two. Examples of even numbers are 2, 4, 6, 8, 10, 12, 14 and so on. One or more of the odd numbered nucleotides of the second strand of the nucleic acid of the invention may be modified wherein the second strand is numbered 3' to 5'. One or more of the even numbered nucleotides of the second strand of the nucleic acid of the invention may be modified, wherein the second strand is numbered 3' to 5'.

One or more nucleotides on the first and/or second strand may be modified, to form modified nucleotides. One or more of the odd numbered nucleotides of the first strand may be modified. One or more of the even numbered nucleotides of the first strand may be modified by at least a second modification, wherein the at least second modification is different from the modification on the one or more add nucleotides. At least one of the one or more modified even numbered nucleotides may be adjacent to at least one of the one or more modified odd numbered nucleotides.

A plurality of odd numbered nucleotides in the first strand may be modified in the nucleic acid of the invention. A plurality of even numbered nucleotides in the first strand may be modified by a second modification. The first strand may comprise adjacent nucleotides that are modified by a common modification. The first strand may also comprise adjacent nucleotides that are modified by a second different modification.

One or more of the odd numbered nucleotides of the second strand may be modified by a modification that is different to the modification of the odd numbered nucleotides on the first strand and/or one or more of the even numbered nucleotides of the second strand may be by the same modification of the odd numbered nucleotides of the first strand. At least one of the one or more modified even numbered nucleotides of the second strand may be adjacent to the one or more modified odd numbered nucleotides. A plurality of odd numbered nucleotides of the second strand may be modified by a common modification and/or a plurality of even numbered nucleotides may be modified by the same modification that is present on the first stand odd numbered nucleotides. A plurality of odd numbered nucleotides on the second strand may be modified by a second modification, wherein the second modification is different from the modification of the first strand odd numbered nucleotides.

The second strand may comprise adjacent nucleotides that are modified by a common modification, which may be a second modification that is different from the modification of the odd numbered nucleotides of the first strand.

In the nucleic acid of the invention, each of the odd numbered nucleotides in the first strand and each of the even numbered nucleotides in the second strand may be modified with a common modification and, each of the even numbered nucleotides may be modified in the first strand with a second modification and each of the odd numbered nucleotides may be modified in the second strand with the second modification.

The nucleic acid of the invention may have the modified nucleotides of the first strand shifted by at least one nucleotide relative to the unmodified or differently modified nucleotides of the second strand.

One or more or each of the odd numbered nucleotides may be modified in the first strand and one or more or each of the even numbered nucleotides may be modified in the second strand. One or more or each of the alternating nucleotides on either or both strands may be modified by a second modification. One or more or each of the even numbered nucleotides may be modified in the first strand and one or more or each of the even numbered nucleotides may be modified in the second strand. One or more or each of the alternating nucleotides on either or both strands may be modified by a second modification. One or more or each of the odd numbered nucleotides may be modified in the first strand and one or more of the odd numbered nucleotides may be modified in the second strand by a common modification. One or more or each of the alternating nucleotides on either or both strands may be modified by a second modification. One or more or each of the even numbered nucleotides may be modified in the first strand and one or more or each of the odd numbered nucleotides may be modified in the second strand by a common modification. One or more or each of the alternating nucleotides on either or both strands may be modified by a second modification.

In a twelfth aspect, the present invention provides a composition comprising a compound according to any of the above aspects and a suitable carrier or excipient.

In a thirteenth aspect, the present invention provides a compound according to any of the first to eleventh aspects or a composition according to the twelfth aspect for use in medicine.

The compound or composition may be for use in the treatment of liver diseases, genetic diseases, hemophilia and bleeding disorders, liver fibrosis, non-alcoholic steotohepatitis (NASH), non-alcoholic fatty liver disease (NAFLD), viral hepatitis, rare diseases (e.g. acromegaly), metabolic diseases (e.g. hypercholesterolemia, dyslipidemia, hypertriglyceridemia), cardiovascular diseases, obesity, thalassemia, liver injury (e.g. drug induced liver injury), hemochromatosis, alcoholic liver diseases, alcohol dependence, anemia, and anemia of chronic diseases.

The compound or composition may be for use in the treatment of liver disease, anemia, chronic diseases, Thalassemia; drug induced liver injury, hemochromatosis and anemia of chronic disease.

In a fourteenth aspect, the present invention provides a method of delivery of nucleic acids to hepatocytes comprising contacting the hepatocyte with a compound according to any of the first to eleventh aspects.

In a fifteenth aspect, the present invention provides a process for making a compound of formula (I), (II) or (III), according to any of the first to eleventh aspects, the process comprising adding together each component to form the compound of formula (I), (II) or (III).

Building blocks of the following structures may be used in the method of manufacture:

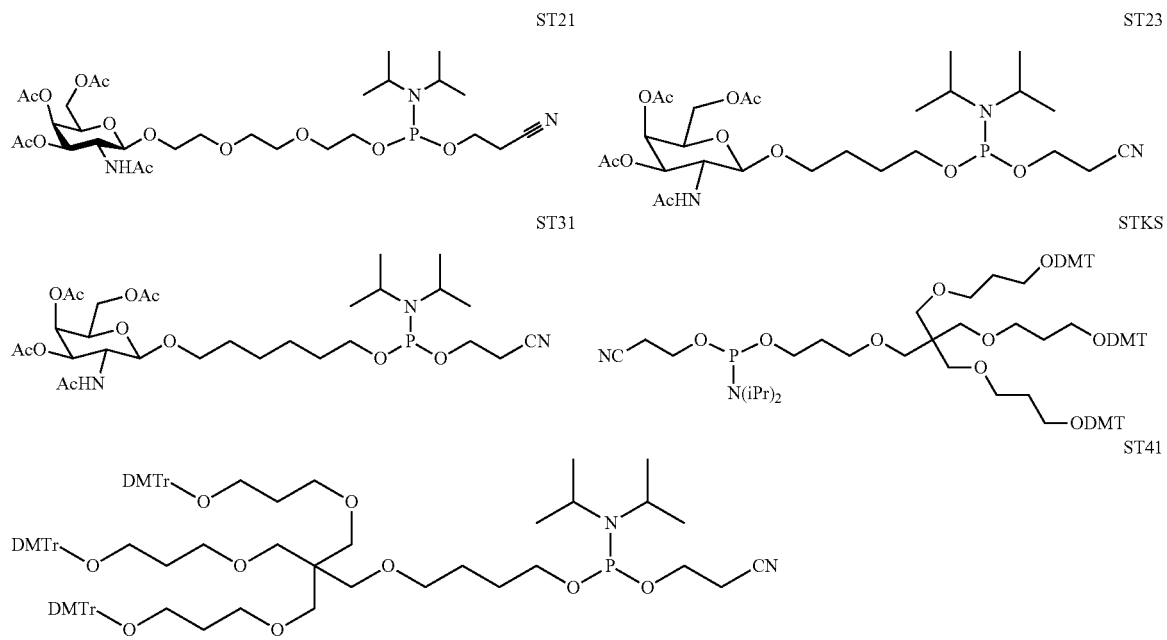

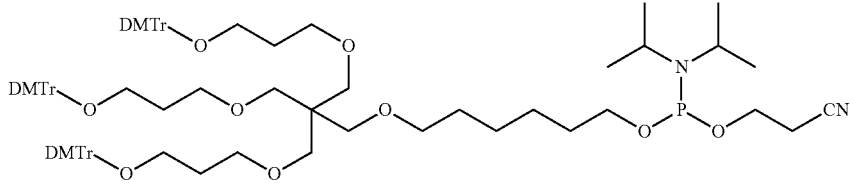

ST43

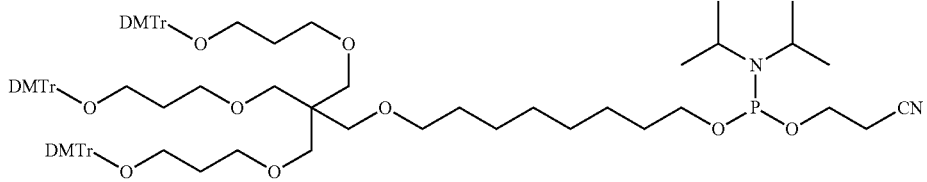

ST45 wherein DMTr=4,4'-dimethoxytrityl (DMTr).

RNA Modifications

Modifications of the siRNA molecules of the present invention generally provides a powerful tool in overcoming potential limitations including, but not limited to, in vitro and in vivo stability and bioavailability inherent to native RNA molecules. The siRNA according to the invention may be modified by chemical modifications. Modified siRNA can also minimize the possibility of activating interferon activity in humans. Modification can further enhance the functional delivery of a siRNA to a target cell. The modified siRNA of the present invention may comprise one or more chemically modified ribonucleotides of either or both of the antisense strand or the sense strand. A ribonucleotide may comprise a chemical modification of the base, sugar or phosphate moieties. The ribonucleic acid may be modified by substitution or insertion with analogues of nucleic acids or bases.

One or more nucleotides of a siRNA of the present invention may comprise a modified base. In one aspect, the siRNA comprises at least one nucleotide comprising a modified base. In one embodiment, the modified base in on the antisense strand. In another embodiment, the modified base in on the sense strand. In another embodiment, the modified base is in the duplex region. In another embodiment, the modified base is outside the duplex region, i.e., in a single stranded region. In another embodiment, the modified base is on the antisense strand and is outside the duplex region. In another embodiment, the modified base is on the sense strand and is outside the duplex region. In another embodiment, the 3'-terminal nucleotide of the antisense strand is a nucleotide with a modified base. In another embodiment, the 3'-terminal nucleotide of the sense strand is nucleotide with a modified base. In another embodiment, the 5'-terminal nucleotide of the antisense strand is nucleotide with a modified base. In another embodiment, the 5'-terminal nucleotide of the sense strand is nucleotide with a modified base.

In one embodiment, a siRNA may have 1 modified base. In another embodiment, a siRNA may have about 2-4 modified bases. In another embodiment, a siRNA has about 4-6 modified bases. In another embodiment, a siRNA has about 6-8 modified bases. In another embodiment, a siRNA has about 8-10 modified bases. In another embodiment, a siRNA has about 10-12 modified bases. In another embodiment, a siRNA has about 12-14 modified bases. In another embodiment, a siRNA has about 14-16 modified bases. In another embodiment, a siRNA has about 16-18 modified bases. In another embodiment, a siRNA has about 18-20 modified bases. In another embodiment, a siRNA has about 20-22 modified bases. In another embodiment, a siRNA has about 22-24 modified bases. In another embodiment, a siRNA has about 24-26 modified bases. In another embodiment, a siRNA has about 26-28 modified bases. In each case the siRNA comprising said modified bases retains at least 50% of its activity as compared to the same siRNA but without said modified bases.

The modified base may be a purine or a pyrimidine. In another embodiment, at least half of the purines are modified. In another embodiment, at least half of the pyrimidines are modified. In another embodiment, all of the purines are modified. In another embodiment, all of the pyrimidines are modified. In another embodiment, the siRNA may comprise a nucleotide comprising a modified base, wherein the base is selected from 2-aminoadenosine, 2,6-diaminopurine, inosine, pyridin-4-one, pyridin-2-one, phenyl, pseudouracil, 2,4,6-trimethoxy benzene, 3-methyl uracil, dihydrouridine, naphthyl, aminophenyl, 5-alkylcytidine (e.g., 5-methylcytidine), 5-alkyluridine (e.g., ribothymidine), 5-halouridine (e.g., 5-bromouridine), 6-azapyrimidine, 6-alkylpyrimidine (e.g. 6-methyluridine), propyne, quesosine, 2-thiouridine, 4-thiouridine, wybutosine, wybutoxosine, 4-acetylcytidine, 5-(carboxyhydroxymethyl)uridine, 5'-carboxymethylaminomethyl-2-thiouridine, 5-carboxymethylaminomethyluridine, beta-D-galactosylqueosine, 1-methyladenosine, 1-methylinosine, 2,2-dimethylguanosine, 3-methylcytidine, 2-methyladenosine, 2-methylguanosine, N6-methyladenosine, 7-methylguanosine, 5-methoxyaminomethyl-2-thiouridine, 5-methylaminomethyluridine, 5-methylcarbonylmethyluridine, 5-methyloxyuridine, 5-methyl-2-thiouridine, 2-methylthio-N6-isopentenyladenosine, beta-D-mannosylqueosine, uridine-5-oxyacetic acid and 2-thiocytidine.

In another aspect, a siRNA of the present invention comprises an abasic nucleotide. The term "abasic" as used herein, refers to moieties lacking a base or having other chemical groups in place of a base at the 1' position, for example a 3',3'-linked or 5',5'-linked deoxyabasic ribose derivative. As used herein, a nucleotide with a modified base does not include abasic nucleotides. In one aspect, the siRNA comprises at least one abasic nucleotide. In one embodiment, the abasic nucleotide is on the antisense strand. In another embodiment, the abasic nucleotide is on the sense strand. In another embodiment, the abasic nucleotide is in the duplex region. In another embodiment, the abasic nucleotide is outside the duplex region. In another embodiment, the abasic nucleotide is on the antisense strand and is outside the duplex region. In another embodiment, the abasic nucleotide is on the sense strand and is outside the duplex region. In another embodiment, the 3'-terminal nucleotide of the antisense strand is an abasic nucleotide. In another embodiment, the 3'-terminal nucleotide of the sense strand is an abasic nucleotide. In another embodiment, the 5'-terminal nucleotide of the antisense strand is an abasic nucleotide. In another embodiment, the 5'-terminal nucleotide of the sense strand is an abasic nucleotide. In another embodiment, a siRNA has a number of abasic nucleotides selected from 1, 2, 3, 4, 5 and 6.

Modifications to Sugar Moiety

Another aspect relates to modifications to a sugar moiety. One or more nucleotides of a siRNA of the present invention may comprise a modified ribose moiety. Modifications at the 2'-position where the 2'-OH is substituted include the non-limiting examples selected from alkyl, substituted alkyl, alkaryl-, arylalkyl-, —F, —Cl, —Br, —CN, —CF3, —OCF3, —OCN, —O-alkyl, —S-alkyl, HS-alkyl-O, —O-alkenyl, —S-alkenyl, —N-alkenyl, —SO-alkyl, -alkyl-OSH, -alkyl-OH, —O-alkyl-OH, —O-alkyl-SH, —S-alkyl-OH, —S-alkyl-SH, -alkyl-S-alkyl, -alkyl-O-alkyl, —ONO2, —NO2, —N3, —NH2, alkylamino, dialkylamino-, aminoalkyl-, aminoalkoxy, aminoacid, aminoacyl-, —ONH2, —O-aminoalkyl, —O-aminoacid, —O-aminoacyl, heterocycloalkyl-, heterocycloalkaryl-, aminoalkylamino-, polyalkylamino-, substituted silyl-, methoxyethyl- (MOE), alkenyl and alkynyl. "Locked" nucleic acids (LNA) in which the 2' hydroxyl is connected, e.g., by a methylene bridge, to the 4' carbon of the same ribose sugar is further included as a 2' modification of the present invention. Preferred substituents are 2'-methoxyethyl, 2'-O—CH3, 2'-O-allyl, 2'-C-allyl, and 2'-fluoro.

In one embodiment, the siRNA comprises 1-5 2'-modified nucleotides. In another embodiment, the siRNA comprises 5-10 2'-modified nucleotides. In another embodiment, the siRNA comprises 15-20 2'-modified nucleotides. In another embodiment, the siRNA comprises 20-25 2'-modified nucleotides. In another embodiment, the siRNA comprises 25-30 2'-modified nucleotides.

In one embodiment, the siRNA comprises 1-5 2'-O—CH3 modified nucleotides. In another embodiment, the siRNA comprises 5-10 2'-O—CH3 modified nucleotides. In another embodiment, the siRNA comprises 15-20 2'-O—CH3 modified nucleotides. In another embodiment, the siRNA comprises 20-25 2'-O—CH3 modified nucleotides. In another embodiment, the siRNA comprises 25-30 2'-O—CH3 modified nucleotides.

In one embodiment, the siRNA duplex region comprises 1-5 2'-O—CH3 modified nucleotides. In another embodiment, the siRNA duplex region comprises 5-10 2'-O—CH3 modified nucleotides. In another embodiment, the siRNA duplex region comprises 15-20 2'-O—CH3 modified nucleotides. In another embodiment, the siRNA duplex region comprises 20-25 2'-O—CH3 modified nucleotides. In another embodiment, the siRNA duplex region comprises 25-30 2'-O—CH3 modified nucleotides.

In one embodiment, the siRNA comprises an antisense strand of 19 nucleotides in length and a sense strand 19 nucleotides in length, wherein said antisense strand comprises 2'-O—CH3 modifications at nucleotides 1, 3, 5, 7, 9, 11, 13, 15, 17 and 19, and wherein said sense strand comprises 2'-O—CH3 modifications at nucleotides 2, 4, 6, 8, 10, 12 ,14, 16 and 18, wherein said antisense strand is numbered from 5'-3' and said sense strand is numbered from 3'-5'. In another embodiment, the siRNA comprises an antisense strand 20 nucleotides in length and a sense strand 20 nucleotides in length, wherein said antisense strand comprises 2'-O—CH3 modifications at nucleotides 1, 3, 5, 7, 9, 11, 13, 15, 17 and 19, and wherein said sense strand comprises 2'-O—CH3 modifications at nucleotides 2, 4, 6, 8, 10, 12 ,14, 16, 18 and 20 wherein said antisense strand is numbered from 5'-3' and said sense strand is numbered from 3'-5'.

In another embodiment, the siRNA comprises an antisense strand 21 nucleotides in length and a sense strand 21 nucleotides in length, wherein said antisense strand comprises 2'-O—CH3 modifications at nucleotides 1, 3, 5, 7, 9, 11, 13, 15, 17, 19 and 21, and wherein said sense strand comprises 2'-O—CH3 modifications at nucleotides 2, 4, 6, 8, 10, 12 ,14, 16, 18 and 20, wherein said antisense strand is numbered from 5'-3' and said sense strand is numbered from 3'-5'. In another embodiment, the siRNA comprises an antisense strand 22 nucleotides in length and a sense strand 22 nucleotides in length, wherein said antisense strand comprises 2'-O—CH3 modifications at nucleotides 1, 3, 5, 7, 9, 11, 13, 15, 17, 19 and 21, and wherein said sense strand comprises 2'-O—CH3 modifications at nucleotides 2, 4, 6, 8, 10, 12 ,14, 16, 18, 20 and 22, wherein said antisense strand is numbered from 5'-3' and said sense strand is numbered from 3'-5'. In another embodiment, the siRNA comprises an antisense strand 23 nucleotides in length and a sense strand 23 nucleotides in length, wherein said antisense strand comprises 2'-O—CH3 modifications at nucleotides 1, 3, 5, 7, 9, 11, 13, 15, 17, 19, 21 and 23, and wherein said sense strand comprises 2'-O—CH3 modifications at nucleotides 2, 4, 6, 8, 10, 12 ,14, 16, 18, 20 and 22 wherein said antisense strand is numbered from 5'-3' and said sense strand is numbered from 3'-5'.

In another embodiment, the siRNA comprises an antisense strand 18-23 nucleotides in length and a sense strand 18-23 nucleotides in length, wherein said antisense strand comprises 2'-O—CH3 modifications at nucleotides 3, 5, 7, 9, 11, 13, 15 and 17, and wherein said sense strand comprises 2'-O—CH3 modifications at nucleotides 4, 6, 8, 10, 12 ,14 and 16, wherein said antisense strand is numbered from 5'-3' and said sense strand is numbered from 3'-5'. In another embodiment, the siRNA comprises an antisense strand 18-23 nucleotides in length and a sense strand 18-23 nucleotides in length, wherein said antisense strand comprises 2'-O—CH3 modifications at nucleotides 5, 7, 9, 11, 13 and 15, and wherein said sense strand comprises 2'-O—CH3 modifications at nucleotides 6, 8, 10, 12 and 14, wherein said antisense strand is numbered from 5'-3' and said sense strand is numbered from 3'-5'. In another embodiment, the siRNA comprises an antisense strand 18-23 nucleotides in length and a sense strand 18-23 nucleotides in length, wherein said antisense strand comprises 2'-O—CH3 modifications at nucleotides 7, 9, 11, 13 and wherein said sense strand comprises 2'-O—CH3 modifications at nucleotides 8, 10 and 12, wherein said antisense strand is numbered from 5'-3' and said sense strand is numbered from 3'-5'. In another embodiment, the siRNA comprises an antisense strand 18-23 nucleotides in length and a sense strand 18-23 nucleotides in length, wherein said antisense strand comprises 2'-O—CH3 modifications at nucleotides 7, 9 and 11, and wherein said sense strand comprises 2'-O—CH3 modifications at nucleotides 8, 10 and 12, wherein said antisense strand is numbered from 5'-3' and said sense strand is numbered from 3'-5'. In another embodiment, the siRNA comprises an antisense strand 18-23 nucleotides in length and a sense strand 18-23 nucleotides in length, wherein said antisense strand comprises 2'-O—CH3 modifications at nucleotides 7 and 9, and wherein said sense strand comprises 2'-O—CH3 modifications at nucleotides 8 and 10, wherein said antisense strand is numbered from 5'-3' and said sense strand is numbered from 3'-5'. In another embodiment, the siRNA comprises an antisense strand 18-23 nucleotides in length and a sense strand 18-23 nucleotides in length, wherein said antisense strand comprises 2'-O—CH3 modifications at nucleotides 9 and 11, and wherein said sense strand comprises 2'-O—CH3 modifications at nucleotides 8 and 10, wherein said antisense strand is numbered from 5'-3' and said sense strand is numbered from 3'-5'.

Pattern

In one aspect, the antisense duplex region comprises a plurality of groups of modified nucleotides, referred to herein as "modified groups", wherein each modified group consists of one or more identically modified nucleotides, wherein each modified group is flanked on one or both sides by a second group of nucleotides, referred to herein as "flanking groups", wherein each said flanking group consists of one or more nucleotides that are either unmodified or modified in a manner different from the nucleotides of said modified group. In one embodiment, each modified group in the antisense duplex region is identical, i.e., each modified group consists of an equal number of identically modified nucleotides. In another embodiment, each flanking group has an equal number of nucleotide. In another embodiment, each flanking group is identical. In another embodiment, the nucleotides of said modified groups in the antisense duplex region comprise a modified base. In another embodiment, the nucleotides of said modified groups comprise a modified phosphate backbone. In another embodiment, the nucleotides of said modified groups comprise a modified 2' position.

In another aspect, the sense duplex region comprises a plurality of groups of modified groups, wherein each modified group consists of one or more identically modified nucleotides, wherein each modified group is flanked on one or both sides by a flanking group, wherein each said flanking group consists of one or more nucleotides that are either unmodified or modified in a manner different from the nucleotides of said modified group. In one embodiment, each modified group in the sense duplex region is identical. In another embodiment, each flanking group has an equal number of nucleotides. In another embodiment, each flanking group is identical. In another embodiment, the nucleotides of said modified groups in the sense duplex region comprise a modified base. In another embodiment, the nucleotides of said modified groups comprise a modified phosphate backbone. In another embodiment, the nucleotides of said modified groups comprise a modified 2' position.

In another aspect, the antisense duplex region and the sense duplex region each comprise a plurality of modified groups, wherein each modified group consists of one or more identically modified nucleotides, wherein each modified group is flanked on one or both sides by a flanking group, wherein each said flanking group consists of one or more nucleotides that are either unmodified or modified in a manner different from the nucleotides of said modified group. In one embodiment, each modified group in the antisense duplex region and the sense duplex region are identical. In another embodiment, each flanking group in the antisense duplex region and the sense duplex region each have an equal number of nucleotides. In another embodiment, each flanking group in the antisense duplex region and in the sense duplex region are identical. In another embodiment, the nucleotides of said modified groups in the antisense duplex region and the sense duplex region each comprise the same modified groups and the same flanking groups. In another embodiment, the nucleotides of said modified groups in the antisense duplex region and the sense duplex region each comprise a modified base. In another embodiment, the nucleotides of said modified groups in the antisense duplex region and the sense duplex region each comprise a modified phosphate backbone. In another embodiment, the nucleotides of said modified groups in the antisense duplex region and the sense duplex region each comprise a modified 2' position.

In one aspect, the antisense strand comprises a plurality of groups of modified nucleotides, referred to herein as "modified groups", wherein each modified group consists of one or more identically modified nucleotides, wherein each modified group is flanked on one or both sides by a second group of nucleotides, referred to herein as "flanking groups", wherein each said flanking group consists of one or more nucleotides that are either unmodified or modified in a manner different from the nucleotides of said modified group. In one embodiment, each modified group in the antisense strand is identical, i.e., each modified group consists of an equal number of identically modified nucleotides. In another embodiment, each flanking group has an equal number of nucleotide. In another embodiment, each flanking group is identical. In another embodiment, the nucleotides of said modified groups in the antisense strand comprise a modified base. In another embodiment, the nucleotides of said modified groups comprise a modified phosphate backbone. In another embodiment, the nucleotides of said modified groups comprise a modified 2' position.

In another aspect, the sense strand comprises a plurality of groups of modified groups, wherein each modified group consists of one or more identically modified nucleotides, wherein each modified group is flanked on one or both sides by a flanking group, wherein each said flanking group consists of one or more nucleotides that are either unmodified or modified in a manner different from the nucleotides of said modified group. In one embodiment, each modified group in the sense strand is identical. In another embodiment, each flanking group has an equal number of nucleotides. In another embodiment, each flanking group is identical. In another embodiment, the nucleotides of said modified groups in the sense strand comprise a modified base. In another embodiment, the nucleotides of said modified groups comprise a modified phosphate backbone. In another embodiment, the nucleotides of said modified groups comprise a modified 2' position.

In another aspect, the antisense strand and the sense strand each comprise a plurality of modified groups, wherein each modified group consists of one or more identically modified nucleotides, wherein each modified group is flanked on one or both sides by a flanking group, wherein each said flanking group consists of one or more nucleotides that are either unmodified or modified in a manner different from the nucleotides of said modified group. In one embodiment, each modified group in the antisense strand and the sense strand are identical. In another embodiment, each flanking group in the antisense strand and the sense strand each have an equal number of nucleotides. In another embodiment, each flanking group in the antisense strand and in the sense strand are identical. In another embodiment, the nucleotides of said modified groups in the antisense strand and the sense strand each comprise the same modified groups and the same flanking groups. In another embodiment, the nucleotides of said modified groups in the antisense strand and the sense strand each comprise a modified base. In another embodiment, the nucleotides of said modified groups in the antisense strand and the sense strand each comprise a modified phosphate backbone. In another embodiment, the nucleotides of said modified groups in the antisense strand and the sense strand each comprise a modified 2' position.

In another aspect, the modified groups and the flanking groups form a regular pattern on the antisense stand. In another aspect, the modified groups and the flanking groups form a regular pattern on the sense strand. In one embodiment, the modified groups and the flanking groups form a regular pattern on the both the antisense strand and the sense strand. In another embodiment, the modified groups and the flanking groups form a regular pattern on the antisense duplex region. In another aspect, the modified groups and the flanking groups form a regular pattern on the sense duplex region. In one embodiment, the modified groups and the flanking groups form a regular pattern on the both the antisense duplex region and the sense duplex region.

In another aspect, the pattern is a spatial or positional pattern. A spatial or positional pattern means that (a) nucleotide(s) are modified depending on their position within the nucleotide sequence of a double-stranded portion. Accordingly, it does not matter whether the nucleotide to be modified is a pyrimidine or a purine. Rather the position of a modified nucleotide is dependent upon: (a) its numbered position on a strand of nucleic acid, wherein the nucleotides are numbered from the 5'-end to the 3'-end with the 5'-end nucleotide of the strand being position one (both the antisense strand and sense strand are numbered from their respective 5'-end nucleotide), or (b) the position of the modified group relative to a flanking group. Thus, according to this embodiment, the modification pattern will always be the same, regardless of the sequence which is to be modified.

In one embodiment, each modified group on both the antisense strand and the sense strand is identical. In one embodiment, each modified group on both the antisense duplex region and the sense duplex region is identical. In another embodiment, each modified group and each flanking group on both the antisense strand and the sense strand are identical. In one embodiment, each modified group and each flanking group on both the antisense duplex region and the sense duplex region are identical.

In one embodiment, each modified group, each modified group position, each flanking group and each flanking group position on both the antisense strand and the sense strand are identical. In one embodiment, each modified group, each modified group position, each flanking group and each flanking group position on both the antisense duplex region and the sense duplex region are identical. In another embodiment, the modified groups on the antisense strand are complementary with the modified groups on the sense strand (the modified groups on the antisense strand and the sense strand are perfectly aligned across from one another). In another embodiment, there are no mismatches in the modified groups such that each modified group on the antisense strand is base paired with each modified group on the sense strand.

In another embodiment, each modified group on the sense strand is shifted by 1, 2, 3, 4 or 5 nucleotides relative to the modified groups on the antisense strand. For example, if each modified group on the sense strand is shifted by one nucleotide or one group of nucleotides and a modified group started at position one on the antisense strand, a modified group on the sense strand would begin at position two. In another embodiment, the modified groups of the antisense strand do not overlap the modified groups of the sense strand, i.e., no nucleotide of a modified group on the antisense strand is base paired with a nucleotide of a modified group on the sense strand.

In one embodiment, deoxyribonucleotides at an end of a strand of nucleic acid are not considered when determining a position of a modified group, i.e., the positional numbering begins with the first ribonucleotide or modified ribonucleotide. In another embodiment, abasic nucleotides at an end of a strand of nucleic acid are not considered when determining a position of a modified group.

In one aspect, a modified group comprises a 5'-end nucleotide of either or both of the antisense strand and the sense strand. In another embodiment, a flanking group comprises the 5'-end nucleotide of either or both of the antisense strand and the sense strand. In another embodiment, the 5'-end nucleotide of either or both of the antisense strand and the sense strand is unmodified. In another embodiment, a modified group comprises the 5'-most nucleotide of either or both of the antisense duplex region and sense duplex region. In another embodiment, a flanking group comprises the 5'-most nucleotide of either or both of the antisense duplex region or the sense duplex region. In another embodiment, the 5'-most nucleotide of either or both of the antisense duplex region or the sense duplex region is unmodified. In one embodiment, the modification at the 2' position is selected from the group comprising amino, fluoro, methoxy, alkoxy and C1-C3-alkyl. In another embodiment, the modification may be selected from 2'-O-methyl, 2'-amino-2'-deoxy, 2'-deoxy-2'-fluoro, 2'-O-methyl, 2'-O-alkyl, and 2'-O—(C1-C3-alkyl). In another embodiment, the modification at the 2' position is 2'-O-methyl.

In another aspect, each modified group consists of one nucleotide and each flanking group consists of one nucleotide. In one embodiment, each modified group on the antisense strand is aligned with a flanking group on the sense strand. In another embodiment, the alignment of each modified group on the antisense strand with the modified group on the sense strand is shifted by one or more nucleotides.

Modifications to Phosphate Backbone

Another aspect relates to modifications to a phosphate backbone. All or a portion of the nucleotides of the siRNA of the invention may be linked through phosphodiester bonds, as found in unmodified nucleic acid. A siRNA of the present invention however, may comprise a modified phosphodiester linkage. The phosphodiester linkages of either the antisense stand or the sense strand may be modified to independently include at least one heteroatom selected from nitrogen and sulfur. In one embodiment, a phosphoester group connecting a ribonucleotide to an adjacent ribonucleotide is replaced by a modified group. In one embodiment, the modified group replacing the phosphoester group is selected from phosphorothioate, methylphosphonate, phosphorodithioate or phosphoramidate group.

In one embodiment, all of the nucleotides of the antisense strand are linked through phosphodiester bonds. In another embodiment, all of the nucleotides of the antisense duplex region are linked through phosphodiester bonds. In another embodiment, all of the nucleotides of the sense strand are linked through phosphodiester bonds. In another embodiment, all of the nucleotides of the sense duplex region are linked through phosphodiester bonds. In another embodiment, the antisense strand comprises a number of modified phosphoester groups selected from 1, 2, 3, 4, 5, 6, 7, 8, 9 or 10. In another embodiment, the antisense duplex region comprises a number of modified phosphoester groups selected from 1, 2, 3, 4, 5, 6, 7, 8, 9 or 10. In another embodiment, the sense strand comprises a number of modified phosphoester groups selected from 1, 2, 3, 4, 5, 6, 7, 8, 9 or 10. In another embodiment, the sense duplex region comprises a number of modified phosphoester groups selected from 1, 2, 3, 4, 5, 6, 7, 8, 9 or 10.

5' and 3' End Modifications

The siRNA of the present invention may include nucleic acid molecules comprising one or more modified nucleotides, abasic nucleotides, acyclic or deoxyribonucleotide at the terminal 5'- or 3'-end on either or both of the sense or antisense strands. In one embodiment, the 5'- and 3'-end nucleotides of both the sense and antisense strands are unmodified. In another embodiment, the 5'-end nucleotide of the antisense strand is modified. In another embodiment, the 5'-end nucleotide of the sense strand is modified. In another embodiment, the 3'-end nucleotide of the antisense strand is modified. In another embodiment, the 3'-end nucleotide of the sense strand is modified. In another embodiment, the 5'-end nucleotide of the antisense strand and the 5'-end nucleotide of the sense strand are modified. In another embodiment, the 3'-end nucleotide of the antisense strand and the 3'-end nucleotide of the sense strand are modified. In another embodiment, the 5'-end nucleotide of the antisense strand and the 3'-end nucleotide of the sense strand are modified. In another embodiment, the 3'-end nucleotide of the antisense strand and the 5'-end nucleotide of the sense strand are modified. In another embodiment, the 3'-end nucleotide of the antisense strand and both the 5'- and 3'-end nucleotides of the sense strand are modified. Both the 5'- and 3'-end nucleotides of the antisense strand may be modified. In another embodiment, both the 5'- and 3'-end nucleotides of the sense strand are modified.

The 5'-end nucleotide of the antisense strand may be phosphorylated. In another embodiment, the 5'-end nucleotide of the sense strand is phosphorylated. In another embodiment, the 5'-end nucleotides of both the antisense strand and the sense strand are phosphorylated. In another embodiment, the 5'-end nucleotide of the antisense strand is phosphorylated and the 5'-end nucleotide of the sense strand has a free hydroxyl group (5'-OH). In another embodiment, the 5'-end nucleotide of the antisense strand is phosphorylated and the 5'-end nucleotide of the sense strand is modified. In another embodiment the 5'-end nucleotide of the antisense strand carries a 5'E vinylphosphonate.

Modifications to the 5'- and 3'-end nucleotides are not limited to the 5' and 3' positions on these terminal nucleotides. Examples of modifications to end nucleotides include, but are not limited to, biotin, inverted (deoxy) abasics, amino, fluoro, chloro, bromo, CN, CF, methoxy, imidazole, carboxylate, thioate, $C_1$ to $C_{10}$ lower alkyl, substituted lower alkyl, alkaryl or arylalkyl, $OCF_3$, OCN, O-, S-, or N-alkyl; O-, S-, or N-alkenyl; SO—CH3; $SO_2CH_3$; $ONO_2$; $NO_2$, $N_3$; heterocycloalkyl; heterocycloalkaryl; aminoalkylamino; polyalkylamino or substituted silyl, as, among others, described, e.g., in PCT patent application WO 99/54459, European patents EP 0 586 520 B1 or EP 0 618 925 B1, incorporated by reference in their entireties. As used herein, "alkyl" means $C_1$-$C_{12}$-alkyl and "lower alkyl" means $C_1$-$C_6$-alkyl, including $C_1$-, $C_2$-, $C_3$-, $C_4$-, $C_5$- and $C_6$-alkyl.

In another aspect, the 5'-end of the antisense strand, the 5'-end of the sense strand, the 3'-end of the antisense strand or the 3'-end of the sense strand may be covalently connected to a prodrug moiety. In one embodiment, the moiety may be cleaved in an endosome. In another the moiety may be cleaved in the cytoplasm.

Examples of different kinds of end modification(s) are presented in Table 1.

TABLE 1

Examples of end modifications

| | | Antisense strand | Sense strand |
|---|---|---|---|
| 1. | 5'-end | free OH | free OH |
| | 3'-end | free OH | free OH |
| 2. | 5'-end | free OH | free OH |
| | 3'-end | end modification | end modification |
| 3. | 5'-end | free OH | free OH |
| | 3'-end | free OH | end modification |
| 4. | 5'-end | free OH | free OH |
| | 3'-end | end modification | free OH |
| 5. | 5'-end | free OH | end modification |
| | 3'-end | free OH | free OH |
| 6. | 5'-end | free OH | end modification |
| | 3'-end | end modification | free OH |
| 7. | 5'-end | free OH | end modification |
| | 3'-end | free OH | end modification |
| 8. | 5'-end | free OH | end modification |
| | 3'-end | end modification | end modification |

In another embodiment, the terminal 3' nucleotide or two terminal 3'-nucleotides on either or both of the antisense strand or sense strand is a 2'-deoxynucleotide. In another embodiment, the 2'-deoxynucleotide is a 2'-deoxy-pyrimidine. In another embodiment, the 2'-deoxynucleotide is a 2' deoxy-thymidine.

shRNA (Short Hairpin Loop RNA) and Linked siRNA

Another aspect relates to shRNA and linked siRNA. The antisense strand and the sense strand may be covalently linked to each other. Such linkage may occur between any of the nucleotides forming the antisense strand and sense strand, respectively and can be formed by covalent or non-covalent linkages. Covalent linkage may be formed by linking both strands one or several times and at one or several positions, respectively, by a compound preferably selected from the group comprising methylene blue and bifunctinoal groups. Such bifunctional groups are preferably selected from the group comprising bis(2-chloroethyl) amine, N-acetly-N'-(p-glyoxylbenzoyl)cystamine, 4-thiouracile and psoralene.

Further, the antisense strand and the sense strand may be linked by a loop structure. The loop structure may be comprised of a non-nucleic acid polymer such as polyethylene glycol. The 5'-end of the antisense strand may be linked to the 3'-terminus of the sense strand or The 3'-end of the antisense strand may be linked to the 5'-end of the sense strand. The loop may consists of a nucleic acid, a locked nucleic acid (LNA), a peptide nucleic acid (PNA), or the loop may be formed by polymers The length of the loop may be sufficient for linking the two strands covalently in a manner that a back folding can occur through a loop structure or similar structure.

The ribonucleic acid constructs may be incorporated into suitable vector systems. Preferably the vector comprises a promoter for the expression of RNAi. The promoter may be selected from any known in the art such as pol III, U6, H1 or 7SK.

The nucleic acids according to the present invention may comprise one or more phosphorothioate internucleotide linkage. Preferably the phosphorothioate internucleotide linkages may be distributed across the entire nucleotide sequences and may occur in any number at any position. Preferably the nucleic acids can comprise between one to ten phosphorothioate internucleotide linkages. Preferably the antisense strand has at least 1 phosphorothioate modification at each end. Preferably the antisense strand has 1-3 phosphorothioate modification at each end. Most preferably the antisense strand has 2 phosphorothioate modification at each end. Preferably the sense strand has at least 1 phosphorothioate modification at the 3' end. Preferably the sense strand has 1-3 phosphorothioate modification at the 3' end. Most preferably the sense strand has 2 phosphorothioate modifications at the 3' end.

siRNA with Overhangs

An overhang at the 3'-end or 5' end of the sense strand or the antisense strand may be selected from consisting of 1, 2, 3, 4 and 5 nucleotides in length. Alternatively, the siRNA molecule may be blunt-ended on both ends and may have a length of 16, 17, 18, 19, 20, 21, 22, 23, 24, 25, 26, 27, 28 or 29 consecutive nucleotides.

In one embodiment, the siRNA molecule is blunt-ended on one end and the double stranded or douplex portion of the siRNA molecule has a length selected from 16, 17, 18, 19, 20, 21, 22, 23, 24, 25, 26, 27, 28 or 29 consecutive nucleotides.

In one embodiment, the siRNA molecule has overhangs on both ends on either strand and the double stranded or duplex portion of the siRNA molecule has a length of 16, 17, 18, 19, 20, 21, 22, 23, 24, 25, 26, 27, 28 or 29 consecutive nucleotides.

The overhang may comprise at least one deoxyribonucleotides and/or a TT dinucleotide. Manufacture of the nucleic acid molecules of the present invention The nucleic acid of the present invention can be produced using routine methods in the art including chemically synthesis or expressing the nucleic acid either in vitro (e.g., run off transcription) or in vivo. For example, using solid phase chemical synthesis or using an expression vector. In one embodiment, the expression vector can produce the nucleic acid of the invention in a target cell. Methods for the synthesis of the nucleic acid molecule described herein are known to persons skilled in the art.

Formulations for Delivery of the Nucleic Acids of the Present Invention siRNAs and conjugated compounds can be delivered to cells, both in vitro and in vivo, by a variety of methods known to those skilled in the art, including direct contact with cells ("naked" siRNA) or by combination with one or more agents that facilitate targeting or delivery into cells. Such agents and methods include lipoplexes, liposomes, iontophoresis, hydrogels, cyclodextrins, nanocapsules, micro- and nanospheres and proteinaceous vectors. The nucleic acid/vehicle combination may be locally delivered in vivo by direct injection or by use of an infusion pump. The siRNA and conjugates of the invention can be delivered in vivo by various means including intravenous subcutaneous, intramuscular or intradermal injection or inhalation. The molecules can be used as pharmaceutical agents. Preferably, pharmaceutical agents prevent, modulate the occurrence, treat or alleviate a symptom of a disease state in a subject.

There is also provided the use of a composition comprising surface-modified liposomes containing poly (ethylene glycol) lipids (PEG-modified, or long-circulating liposomes or stealth liposomes). These formulations offer a method for increasing stability of a liposome or lipoplex solutions by preventing their aggregation and fusion. The formulations also have the added benefit in vivo of resisting opsonization and elimination by the mononuclear phagocytic system (MPS or RES), thereby enabling longer blood circulation times and enhanced tissue exposure for the encapsulated drug. Such liposomes have been may accumulate selectively in tumors, presumably by extravasation and capture in the neovascularized target tissues The long-circulating liposomes enhance the pharmacokinetics and pharmacodynamics of DNA and RNA, particularly compared to conventional cationic liposomes which are known to accumulate in tissues of the MPS (Liu et al., J. Biol. Chem. 1995,42,24864-24780; Choi et al., International PCT Publication No. WO 96/10391; Ansell et al., International PCT Publication No. WO 96/10390; Holland et al., International PCT Publication No. WO 96/10392). Long-circulating liposomes also protect the siRNA from nuclease degradation.

The siRNA conjugates of the present invention may be formulated as pharmaceutical compositions. The pharmaceutical compositions may be used as medicaments or as diagnostic agents, alone or in combination with other agents. For example, one or more siRNA conjugates of the invention can be combined with a delivery vehicle (e.g., liposomes) and excipients, such as carriers, diluents. Other agents such as preservatives and stabilizers can also be added. Methods for the delivery of nucleic acid molecules are known in the art and within the knowledge of the person skilled in the art.

The siRNA conjugates of the present invention can also be administered in combination with other therapeutic compounds, either administrated separately or simultaneously, e.g., as a combined unit dose. In one embodiment, the invention includes a pharmaceutical composition comprising one or more siRNA conjugates according to the present invention in a physiologically/pharmaceutically acceptable excipient, such as a stabilizer, preservative, diluent, buffer, and the like.

Dosage

Dosage levels for the medicament and pharmaceutical compositions of the invention can be determined by those skilled in the art by routine experimentation. In one embodiment, a unit dose may contain between about 0.01 mg/kg and about 100 mg/kg body weight of siRNA. Alternatively, the dose can be from 10 mg/kg to 25 mg/kg body weight, or 1 mg/kg to 10 mg/kg body weight, or 0.05 mg/kg to 5 mg/kg body weight, or 0.1 mg/kg to 5 mg/kg body weight, or 0.1 mg/kg to 1 mg/kg body weight, or 0.1 mg/kg to 0.5 mg/kg body weight, or 0.5 mg/kg to 1 mg/kg body weight.

The pharmaceutical composition may be a sterile injectable aqueous suspension or solution, or in a lyophilized form. In one embodiment, the pharmaceutical composition may comprise lyophilized lipoplexes or an aqueous suspension of lipoplexes. The lipoplexes preferably comprises a siRNA of the present invention. Such lipoplexes may be used to deliver the siRNA of the invention to a target cell either in vitro or in vivo.

The pharmaceutical compositions and medicaments of the present invention may be administered to a mammalian subject in a pharmaceutically effective dose. The mammal may be selected from humans, dogs, cats, horses, cattle, pig, goat, sheep, mouse, rat, hamster and guinea pig.

Routes of Delivery

A conjugated composition that includes a double stranded siRNA can be delivered to a subject by a variety of routes. Exemplary routes include: sub cuteanous, intravenous, topical, rectal, anal, vaginal, nasal, pulmonary, ocular.

The conjugated composition can be incorporated into pharmaceutical compositions suitable for administration with a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The compositions of the present invention may be administered in a number of ways depending upon whether local or systemic treatment is desired and upon the area to be treated. Administration may be topical (including ophthalmic, vaginal, rectal, intranasal, transdermal), oral or parenteral. Parenteral administration includes intravenous drip, subcutaneous, intraperitoneal or intramuscular injection, or intrathecal or intraventricular administration.

The route and site of administration may be chosen to enhance targeting. For example, to target muscle cells, intramuscular injection into the muscles of interest would be a logical choice. Lung cells might be targeted by administering the iRNA in aerosol form. The vascular endothelial cells could be targeted by coating a balloon catheter with the iRNA and mechanically introducing the DNA.

It will be appreciated by one skilled in the art that the modification, modifications of the sugar moiety, pattern, 5' and 3' end modifications, overhangs, formulations, delivery, dosage and routes of delivery as described above may equally be applied to any type of iRNA molecule and is not limited to siRNAs.

According to the thirteenth aspect of the present invention there is provided the use of the compounds or compositions of the present invention in medicine. GalNAc conjugates according to the invention may be used for the treatment of liver diseases, chronic diseases, Thalassemia, drug induced liver injury, hemochromatosis and anemia or anemia of chronic disease.

In a further aspect of the invention there is provided a method of delivery of nucleic acids to hepatocytes using the conjugates according to the present invention. The method comprises the steps of contacting the hepatocyte with the compound of the present invention. The method may be used in vitro or in vivo, for diagnostic purposes, therapy or research purposes.

The duration of knockdown with siRNA conjugates of the present invention is much more pronounced and more long lasting when compared with compound TTRCF02 which incorporates the standard Biessen/van Berkel type of GalNAc linker (as in structure ST13).

Figure 4:
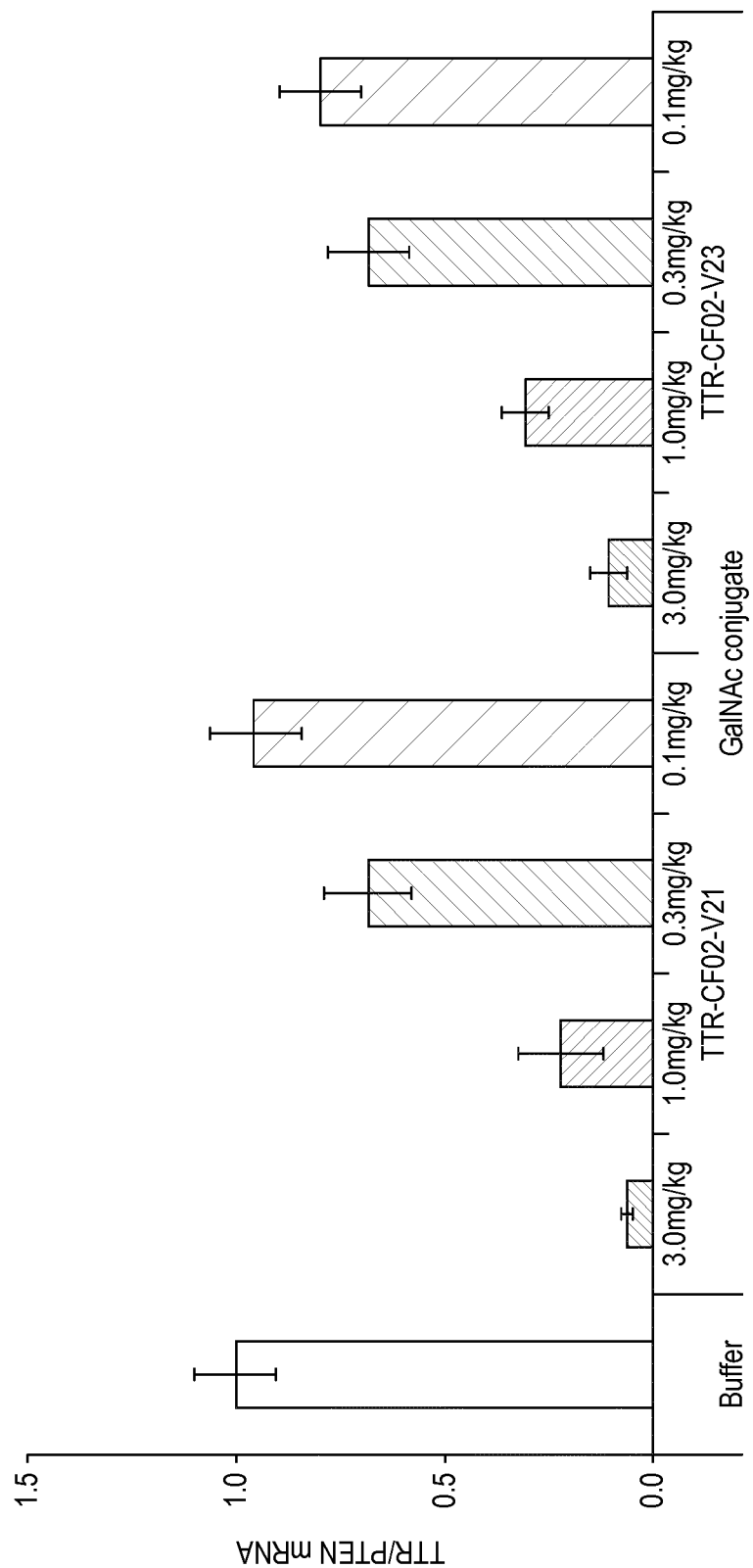

FIG. 4 is a bar chart illustrating a dose titration of TTR knockdown in mice. Mice (4 animals per group) were treated with the respective dose (3, 1, 0.3, 0.1 mg/kg). TTR mRNA level was quantified by TAQman PCR. mRNA level were normalised against PTEN.

Figure 5:
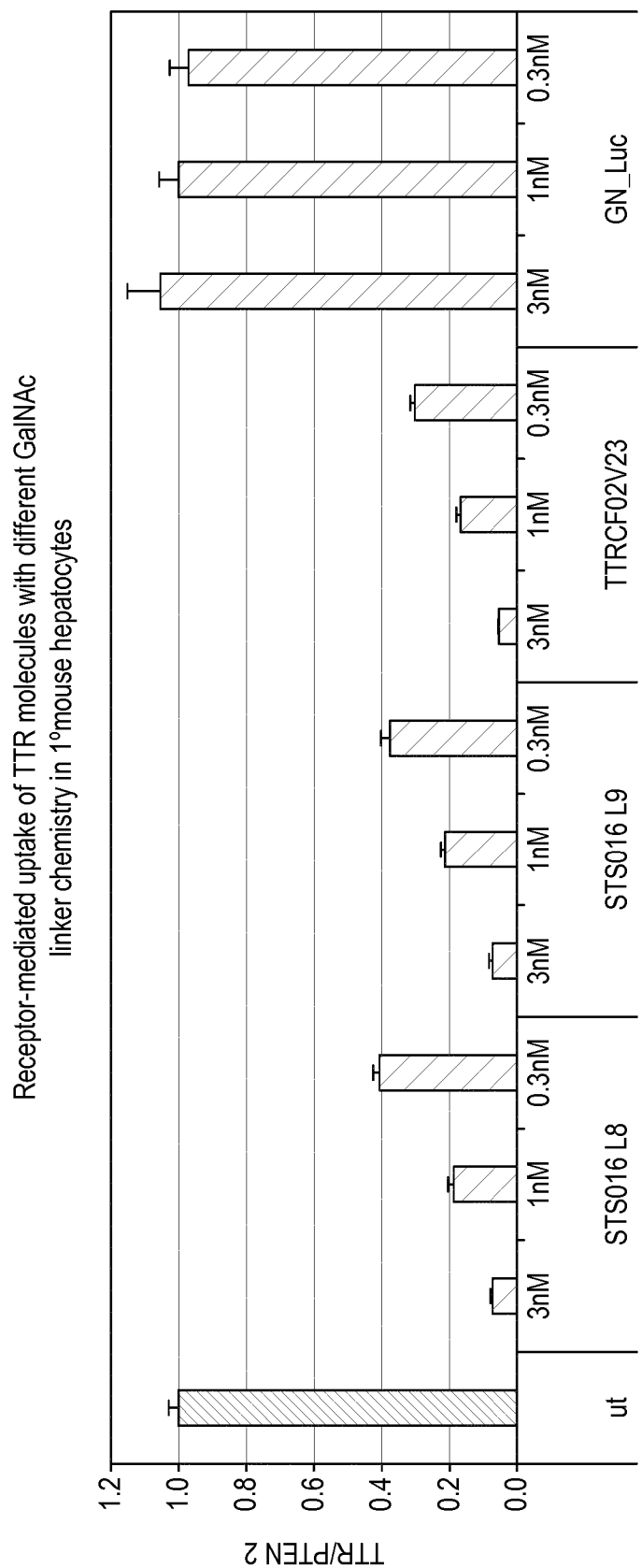

FIG. 5 is a bar chart illustrating the in vitro determination of TTR knockdown of TTR siRNA GalNAc conjugates STS016 L8 and L9. TTR CF02V23 represents the positive control. GN_Luc represents the negative control. mRNA level were normalised against PTEN.

Figure 6:
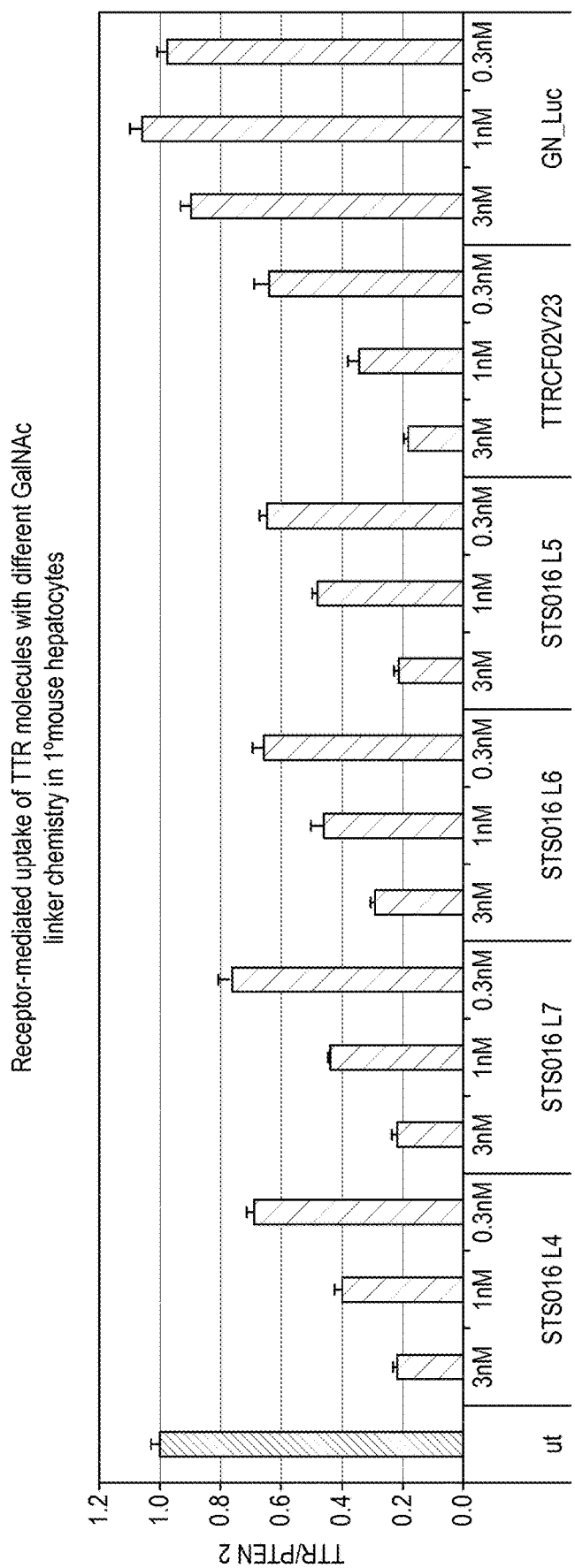

FIG. 6 is a bar chart illustrating the in vitro determination of TTR knockdown of TTR siRNA GalNAc conjugates STS016 L4-L7. TTR CF02V23 represents the positive control. GN_Luc represents the negative control. mRNA level were normalised against PTEN.

Figure 7:
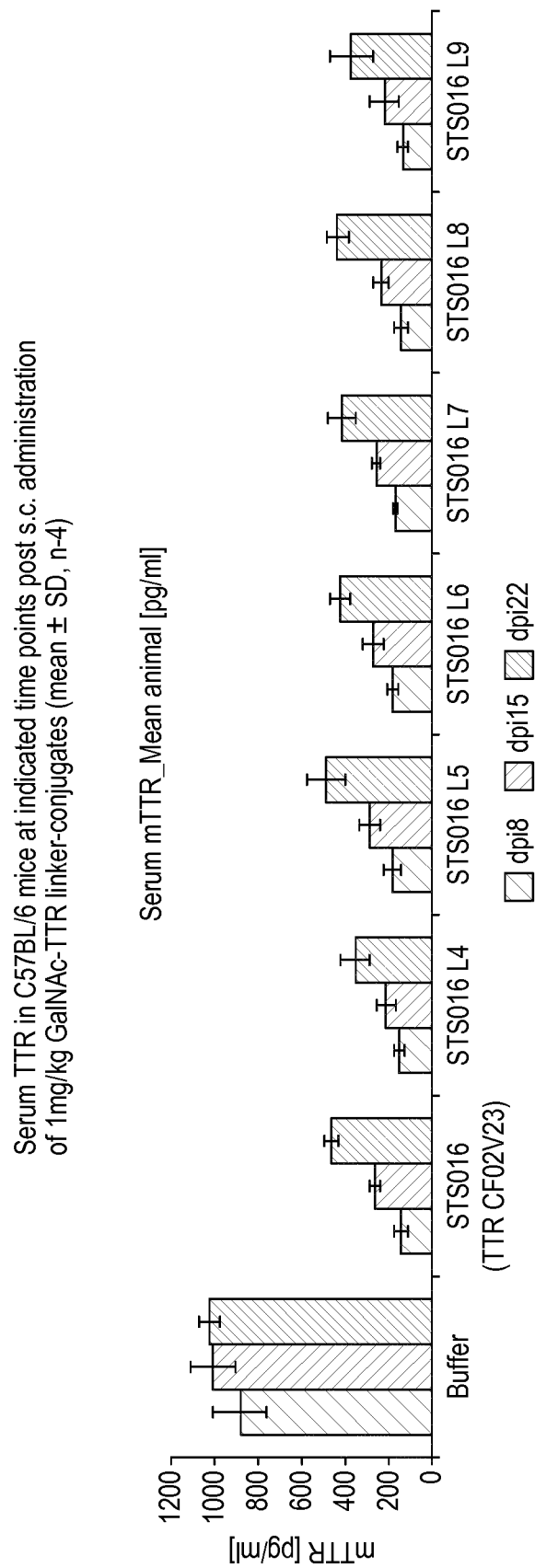

FIG. 7 is a bar chart illustrating in vivo efficacy of TTR knockdown in mice. Mice (4 animals per group) were treated with a single subcuteanous dose of 1 mg/kg. Blood was taken after each timepoint (day 8, 15, 22 post injection) and analysed for TTR level using commercially available murineTTR specific Elisa Kit.

Figure 8:
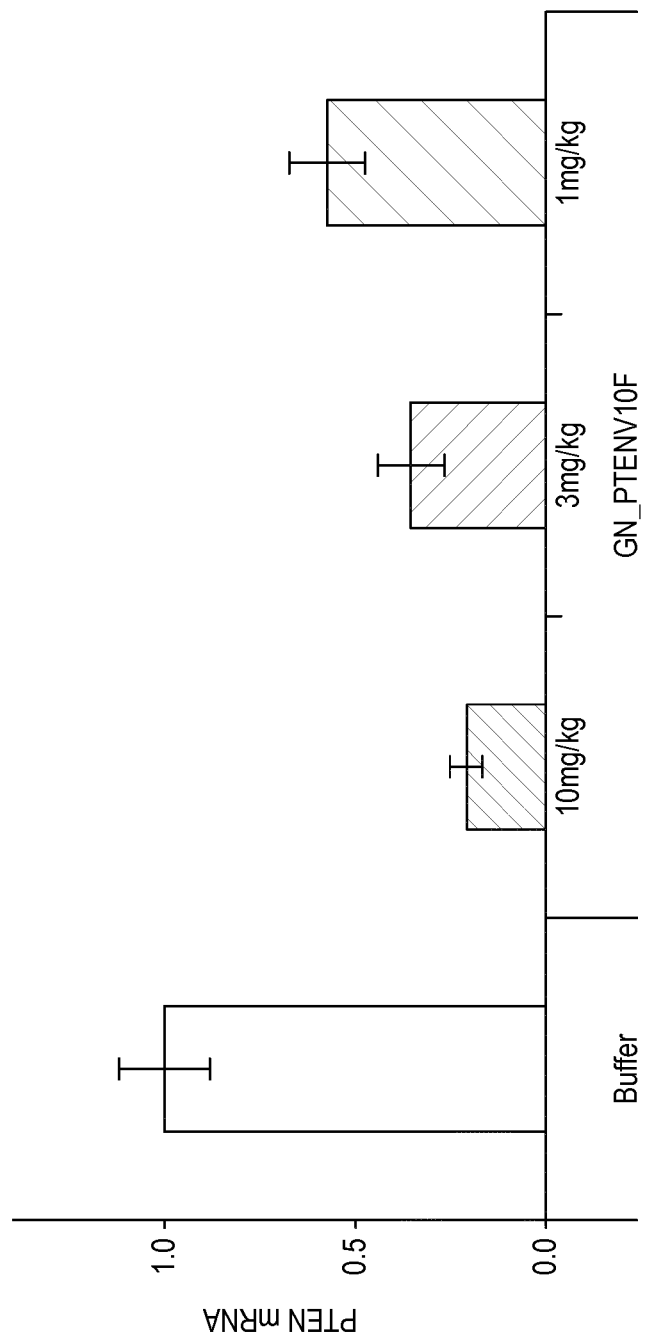

FIG. 8 is a bar chart illustrating in vivo efficacy of PTEN Knockdown in mice. Mice (4 animals per group) were treated with the respective dose (1, 3, 10 mg/kg). PTEN mRNA level was quantified by TAQman PCR. A clear dose dependent knockdown of PTEN was demonstrated.

EXAMPLES

General Information

All reactions were carried out under a nitrogen atmosphere, unless stated otherwise. NMR spectra were recorded on a Bruker 400 MHz Ultrashield™ and all chemical shifts (δ) were determined relative to TMS.

Example 1

Synthesis of GalNAc Phosphoramidites

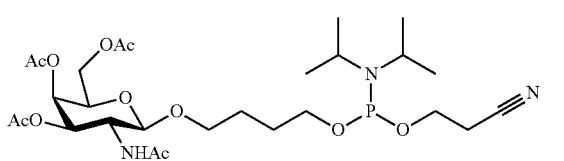

ST23

The synthesis of the respective phosphoramidites follow essentially the procedure described in Prakash et al. Bioorg. Med. Chem. Lett. 25 (2015) 4127-4130.

Galactosamine penta acetate was activated with trimethylsilyl trifluoromethylsulfonate and reacted with 4-Benzyloxy 1-butanol. After hydrogenolytical removal of the Benzyl protecting group the resulting alcohol was transferred into the phosphoramidite following the method described by Dubber, 2003.

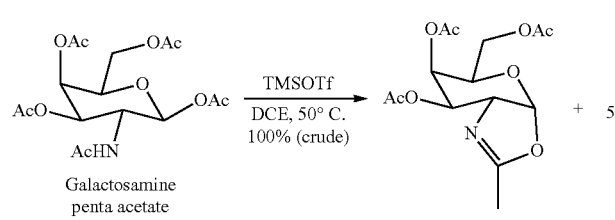
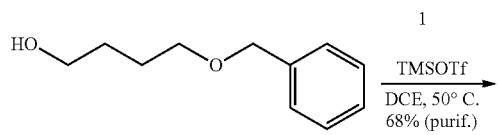
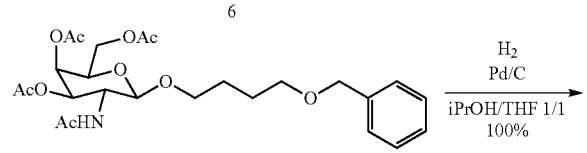
7
Qy: 45.4 g
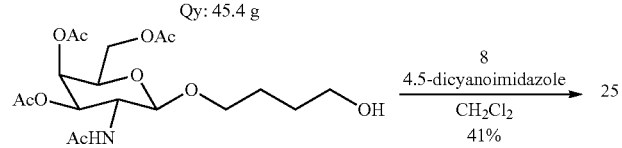
14B
Qy: 7.8 g
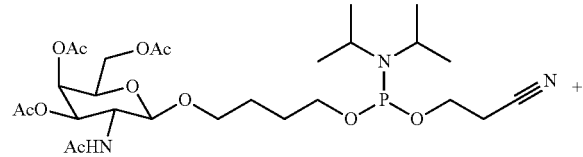
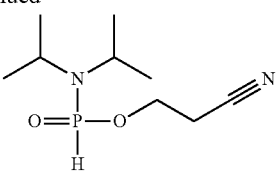
8 = 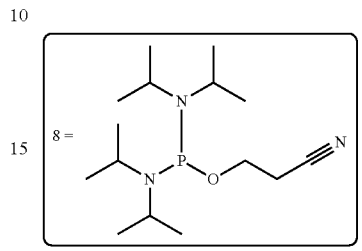
ST21
ST21 was synthesized following the same procedure as above using Benzyl protected triethylene glycol as starting material.
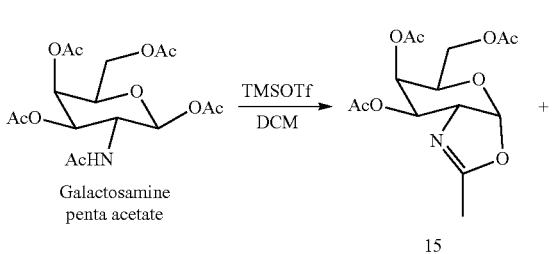
15
Triethyleneglycolmonobenzyl ether
a) TMSOTf, DCE
b) Et₃N, DMAP, TBDMSCl, DCM
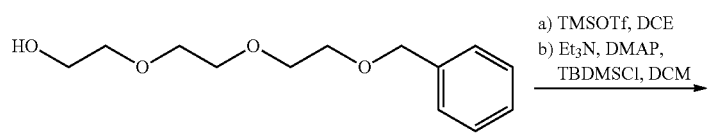
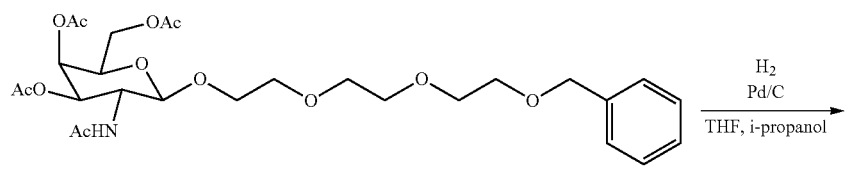
19

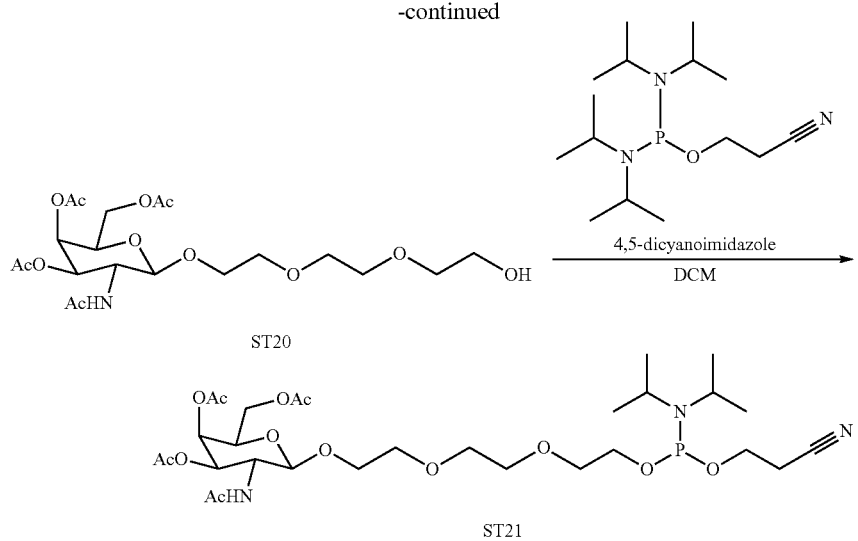

(2R,3R,4R,5R,6R)-5-acetamido-2-(acetoxymethyl)-6-(2-(2-(2-(benzyloxy)ethoxy)ethoxy)ethoxy)tetrahydro-2H-pyran-3,4-diyl diacetate (19)

To a solution of 15 (64.2 g, 166 mmol) in 1,2-dichloroethane (700 mL) was added trimethylsilyl trifluoromethanesulfonate (22.10 g, 99 mmol, 18.04 mL, 0.6 equiv) and the brown suspension was stirred for 15 minutes. Grinded 4A molecular sieves (85 g) were added and stirring was continued for 15 minutes. Triethyleneglycolmonobenzyl ether (51.8 g, 215 mmol, 47.5 mL, 1.3 equiv) was added, via drop wise addition, over a period of 15 minutes and stirring was continued at room temperature. The reaction mixture was filtered over a plug of kieselguhr followed by rinsing with warm dichloromethane. The filtrate was quenched by pouring in ice-cold aqueous saturated $NaHCO_3$ solution (800 mL) and stirred vigerously. The layers were separated and the aqueous layer was extracted twice more with dichloromethane (2×300 mL). The combined organic layers were washed with water (600 mL) and brine (600 mL), dried over $Na_2SO_4$, filtered and concentrated in vacuo to obtain a yellow oil. Purification was performed by flash column chromatography (5-100% EtOAc in heptane) to obtain a mixture of 19 and triethyleneglycolmonobenzyl ether (64 g). This material was dissolved in dichloromethane (430 mL) followed by the addition of triethylamine (38.4 g, 380 mmol, 52.8 ml, 4 equiv) and DMAP (2.321 g, 19.00 mmol, 0.2 equiv). Then, via batch wise addition, was added TBDMSCl (21.47 g, 142 mmol, 1.5 equiv) and stirring was continued at room temperature for 2 hours. The reaction mixture was filtered and followed by pouring in an ice cold saturated solution of NaHCO3 (1 L). The layers were separated and the aqueous layer was extracted twice more with dichloromethane (2×300 mL).

The combined organic layers were washed once with brine (1 L) and dried over $Na_2SO_4$. After concentrating in vacuo, followed by flash column chromatography (70-100% EtOAc in heptane), 19 was obtained as a colourless oil (36 g, yield 30%) $^1$H NMR (400 MHz, Chloroform-d) δ 7.38-7.28 (m, 5H), 6.58 (d, J=9.5 Hz, 1H), 5.26 (d, J=3.3 Hz, 1H), 4.96 (dd, J=11.2, 3.4 Hz, 1H), 4.79 (d, J=8.6 Hz, 1H), 4.53 (d, J=1.3 Hz, 2H), 4.28 (dt, J=11.2, 9.0 Hz, 1H), 4.16-4.06 (m, 2H), 3.88 (dd, J=6.0, 2.7 Hz, 2H), 3.75 (td, J=5.7, 2.7 Hz, 4H), 3.71-3.58 (m, 7H), 2.15 (s, 3H), 2.04 (s, 3H), 1.97 (s, 3H), 1.95 (s, 3H).

(2R,3R,4R,5R,6R)-5-acetamido-2-(acetoxymethyl)-6-(2-(2-(2-hydroxyethoxy)ethoxy)ethoxy)tetrahydro-2H-pyran-3,4-diyl diacetate (ST20)

To a solution of 19 (47.68 g, 84 mmol) in tetrahydrofuran (330 ml) and 2-propanol (330 ml) was added 10% palladium on activated carbon (12.92 g, 12.14 mmol, 1.45 equiv). The reaction mixture was charged with hydrogen (balloon) and stirring was continued at room temperature overnight. The reaction mixture was filtered over kieselguhr and rinsed with warm dichloromethane. After concentrating in vacuo, ST20 was obtained (37 g, yield 94%) $^1$H NMR (400 MHz, DMSO-$d_6$) δ 7.81 (d, J=9.2 Hz, 1H), 5.22 (d, J=3.3 Hz, 1H), 4.97 (dd, J=11.2, 3.4 Hz, 1H), 4.61 (t, J=5.4 Hz, 1H), 4.56 (d, J=8.4 Hz, 1H), 4.03 (s, 3H), 3.88 (dt, J=11.1, 8.9 Hz, 1H), 3.82-3.73 (m, 1H), 3.63-3.45 (m, 9H), 3.41 (t, J=5.1 Hz, 2H), 2.11 (s, 3H), 2.00 (s, 3H), 1.89 (s, 3H), 1.78 (s, 3H).

(2R,3R,4R,5R,6R)-5-acetamido-2-(acetoxymethyl)-6-(2-(2-(2-(((2- cyanoethoxy)(diisopropylamino) phosphino)oxy)ethoxy)ethoxy)ethoxy)tetrahydro-2H-pyran-3,4-diyl diacetate (ST21)

To a solution of 4,5-dicyanoimidazole (961 mg, 8.13 mmol, 0.65 equiv) in anhydrous acetonitrile (8 mL) and dry dichloromethane (40 ml) were added grinded 4A molecular sieves (4.4 g). Then, 2-cyanoethyl tetraisopropylphosphorodiamidite (4903 mg, 16.27 mmol, 5.16 ml, 1.3 equiv) was added via a syringe and stirred at room temperature for 10 minutes. Then, a solution of ST20 (6000 mg, 12.51 mmol) in dry dichloromethane (20 ml) was added to the reaction mixture over a period of 10 minutes. The reaction mixture was filtered over a cotton plug followed by concentrating in vacuo. Purification by flash column chromatography was performed twice (10-100% EtOAc in heptane) to obtain ST21 as a pale yellow oil (6.9 g, yield 74%). $^1$H NMR (400 MHz, DMSO-$d_6$) δ 7.81 (d, J=9.3 Hz, 1H), 5.21 (d, J=3.4 Hz, 1H), 4.97 (dd, J=11.2, 3.4 Hz, 1H), 4.55 (d, J=8.5 Hz, 1H), 4.03 (d, J=3.0 Hz, 3H), 3.88 (dt, J=11.2, 8.9 Hz, 1H), 3.82-3.45 (m, 16H), 2.77 (t, J=6.1 Hz, 2H), 2.11 (s, 3H), 2.00 (s, 3H), 1.89 (s, 3H), 1.77 (s, 3H), 1.13 (dd, J=6.8, 3.1 Hz, 12H).

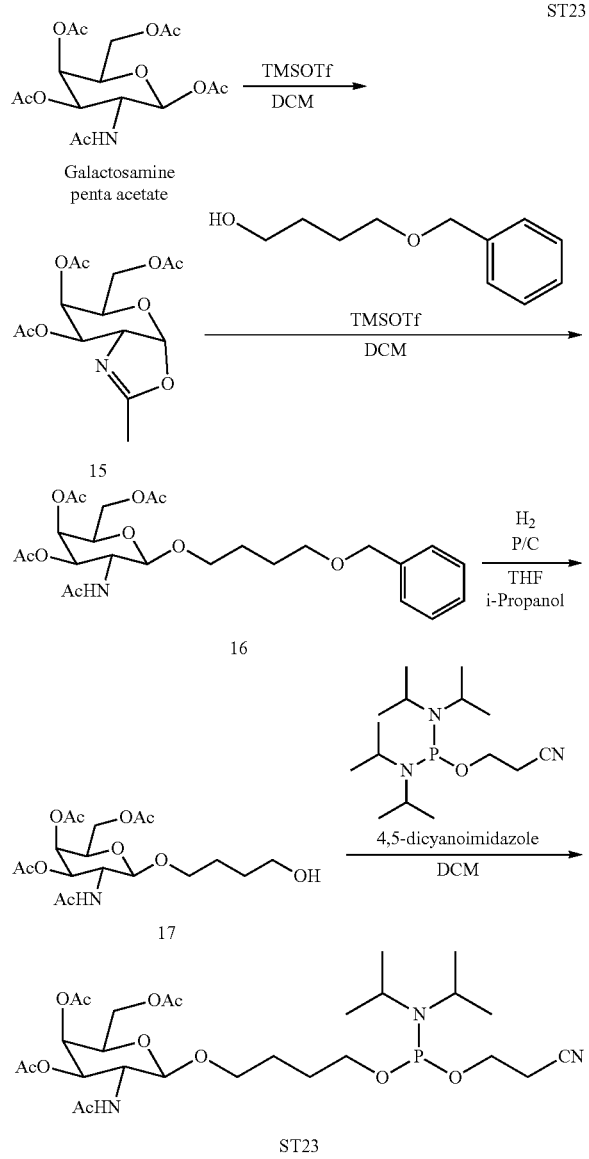

(3aR,5R,6R,7R,7aR)-5-(acetoxymethyl)-2-methyl-5,6,7,7a-tetrahydro-3aH-pyrano[3,2-d]oxazole-6,7-diyl diacetate (15)

To a suspension of Galactosamine pentaacetate (125 g, 321 mmol) in dichloromethane (870 mL) at room temperature was added, via drop wise addition, trimethylsilyltrifluoromethanesulfonate (107 g, 482 mmol, 87 mL, 1.5 equiv) over a period of 30 minutes. The reaction mixture was heated to 40° C. for a period of 2 hours, after which it was cooled back to room temperature and quenched by pouring in an ice-cold aqueous saturated NaHCO$_3$ solution (1000 mL). The layers were separated and the aqueous layer was extracted twice more with dichloromethane (2×300 mL). The combined organic layers were washed with water (500 mL) and brine (800 mL), followed by drying over Na$_2$SO$_4$.

After concentrating in vacuo 15 was obtained as a pale yellow oil (109 g, crude yield 103%). $^1$H NMR (400 MHz, Chloroform-d) δ 6.00 (d, J=6.8 Hz, 1H), 5.47 (t, J=3.0 Hz, 1H), 4.91 (dd, J=7.4, 3.3 Hz, 1H), 4.29-4.06 (m, 3H), 4.03-3.97 (m, 1H), 2.13 (s, 3H), 2.07 (d, J=1.0 Hz, 6H), 2.06 (d, J=1.3 Hz, 3H).

(2R,3R,4R,5R,6R)-5-acetamido-2-(acetoxymethyl)-6-(4-(benzyloxy)butoxy)tetrahydro-2H-pyran-3,4-diyl diacetate (16)

To a solution of 15 (109 g, 331 mmol) in dichloromethane (1200 mL) were added powdered molsieves 4A (75 g) followed by stirring for 15 minutes at room temperature. To the mixture was added 4-benzyloxy-l-butanol (89 g, 497 mmol, 87 mL, 1.5 equiv) and stirring was continued for another 15 minutes. Then, via dropwise addition, was added trimethylsilyltrifluoromethanesulfonate (44.1 g, 199 mmol, 36.0 mL, 0.6 equiv) over a period of 15 minutes. Stirring of the reaction mixture was continued for 2 hours. Filtration of the mixture was performed over a plug of kieselguhr followed by rinsing once with dichloromethane (200 mL). The filtrate was then quenched by pouring in an ice-cold saturated aqueous NaHCO$_3$ solution (1000 mL). The layers were separated followed by extracting the aqueous layer twice more with dichloromethane (2×500 mL). The combined organic layers were washed with water (600 mL) and brine (600 mL) followed by drying over Na$_2$SO$_4$. After concentrating in vacuo, purification was performed by flash column chromatography on silica neutralized with 1% Et$_3$N (20-80% EtOAc in heptane) to obtain 16 as a colourless oil which slowly crystalized (109 g, yield 65%). $^1$H NMR (400 MHz, DMSO-d$_6$) δ 7.83 (d, J=9.3 Hz, 1H), 7.39-7.23 (m, 5H), 5.21 (d, J=3.5 Hz, 1H), 4.96 (dd, J=11.2, 3.5 Hz, 1H), 4.48 (d, J=8.5 Hz, 1H), 4.44 (s, 2H), 4.07-3.97 (m, 3H), 3.87 (dt, J=11.2, 8.8 Hz, 1H), 3.72 (p, J=5.3 Hz, 1H), 3.49-3.37 (m, 3H), 2.10 (s, 3H), 1.99 (s, 3H), 1.89 (s, 3H), 1.76 (s, 3H), 1.54 (qd, J=8.0, 5.2, 4.6 Hz, 4H).

(2R,3R,4R,5R,6R)-5-acetamido-2-(acetoxymethyl)-6-(4-hydroxybutoxy)tetrahydro-2H-pyran-3,4-diyl diacetate (17)

To a solution of 16 (109.6 g, 215 mmol) in tetrahydrofuran (1000 mL) and 2-propanol (1000 mL) was added 10% palladium on carbon (17.17 g, 16.13 mmol, 10%, 0.075 equiv) and the flask was charged with hydrogen (atmospheric pressure). Stirring of the reaction mixture was continued overnight at room temperature. The mixture was filtered over a plug of kieselguhr and concentrated in vacuo. After stripping the material twice with toluene (2×300 mL) and dichloromethane (2×300 mL), 17 was obtained as a white sticky solid (87 g, yield 97%). $^1$H NMR (400 MHz, Methanol-d$_4$) δ 5.33 (dd, J=3.5, 1.0 Hz, 1H), 5.05 (dd, J=11.3, 3.3 Hz, 1H), 4.55 (d, J=8.5 Hz, 1H), 4.20-3.97 (m, 4H), 3.87 (dt, J=10.1, 5.8 Hz, 1H), 3.60-3.48 (m, 3H), 3.30 (p, J=1.8 Hz, 1H), 2.14 (s, 3H), 2.02 (s, 3H), 1.94 (s, 3H), 1.92 (s, 3H), 1.61 (dtd, J=16.8, 11.0, 10.1, 3.6 Hz, 4H).

(2R,3R,4R,5R,6R)-5-acetamido-2-(acetoxymethyl)-6-(4-(((2-cyanoethoxy)(diisopropylamino)phosphino)oxy)butoxy)tetrahydro-2H-pyran-3,4-diyl diacetate (ST23)

To a solution of 4,5-dicyanoimidazole (1.940 g, 16.43 mmol, 0.65 equiv) in dry acetonitrile (20 mL) and dry dichloromethane (20 mL), under an argon atmosphere, were added grinded Molsieves 4A (9 g). Then, 2-cyanoethyl tetraisopropylphosphoro-diamidite (10.00 g, 33.2 mmol, 10.53 mL, 1.31 equiv) was added via a syringe and stirred at room temperature for 10 minutes. Via drop wise addition was then added a solution of 17 (10.6 g, 25.3 mmol) in dry dichloromethane (50 mL) over a period of 10 minutes. After stirring for an additional 30 minutes, the reaction mixture was filtered over a cotton plug and concentrated in vacuo. Purification of the material was performed by multiple flash column chromatograph steps (0-100% EtOAc in heptane with 5% Et$_3$N) to obtain ST23 as a pale yellow oil (11.75 g, yield 72%). $^1$H NMR (400 MHz, DMSO-d$_6$) δ 7.82 (d, J=9.2 Hz, 1H), 5.21 (d, J=3.4 Hz, 1H), 4.96 (dd, J=11.2, 3.5 Hz, 1H), 4.48 (d, J=8.5 Hz, 1H), 4.02 (s, 3H), 3.93-3.82 (m, 1H), 3.78-3.65 (m, 3H), 3.64-3.49 (m, 4H), 3.48-3.40 (m, 1H), 2.76 (t, J=5.9 Hz, 2H), 2.11 (s, 3H), 2.00 (s, 3H), 1.89 (s, 3H), 1.77 (s, 3H), 1.62-1.46 (m, 4H), 1.13 (dd, J=6.8, 3.6 Hz, 12H). $^{31}$P NMR (162 MHz, Chloroform-d) 147 (d, J=8.6 Hz)

(500 mL) was added, via dropwise addition, a solution of 1,6-hexanediol (265 g, 2242 mmol, 3.5 equiv) in tetrahydrofuran (1000 mL) over a period of one hour. After stirring for an additional 30 minutes, a solution of benzyl bromide (76 mL, 641 mmol, 1 equiv) in tetrahydrofuran (500 mL) was added over a period of 30 minutes. Upon complete addition, the reaction mixture was allowed to reach room temperature and stirring was continued overnight. The reaction mixture was cooled to a temperature of 5° C. followed by the slow addition of water (200 mL). The mixture was then concentrated in vacuo, redissolved in dichloromethane (600 mL) and washed with water (3000 mL). The aqueous layer was extracted three more times with dichloromethane (3×500 mL). The combined organic layers were washed with water (3×400 mL) and brine (1×500 mL) followed by drying over Na$_2$SO$_4$ and concentrating in vacuo. Purification was performed by gravity column chromatography (0-50%

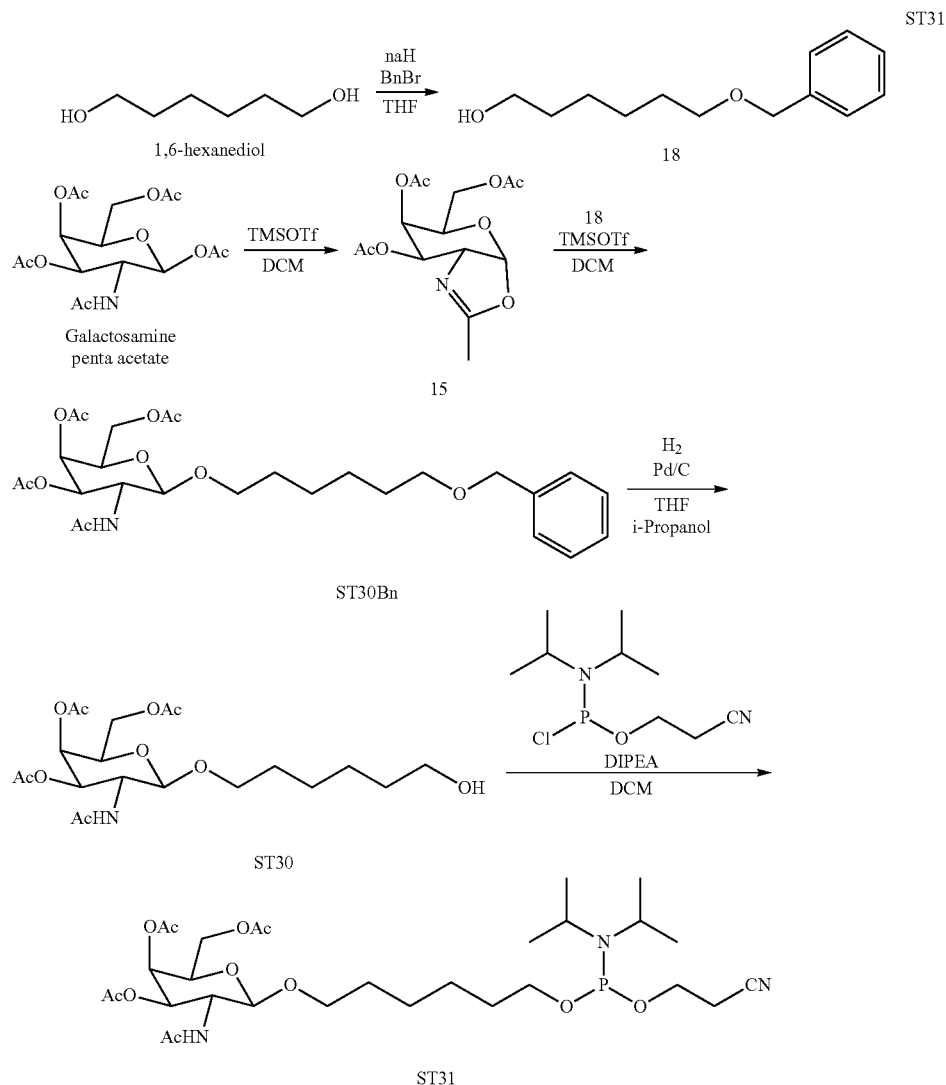

6-(benzyloxy)hexan-1-ol (18)

To a cooled and vigerously stirred suspension of sodium hydride (90 g, 2242 mmol, 3.5 equiv) in tetrahydrofuran EtOAc in heptane) to obtain 18 (25 g, yield 20%). $^1$H NMR (400 MHz, Chloroform-d) δ 7.40-7.27 (m, 5H), 4.50 (s, 2H), 3.64 (t, J=6.7 Hz, 2H), 3.47 (t, J=6.6 Hz, 2H), 1.68-1.51 (m, 4H), 1.47-1.31 (m, 4H), 1.27 (s, 1H).

(2R,3R,4R,5R,6R)-5-acetamido-2-(acetoxymethyl)-6-((6-(benzyloxy)hexyl)oxy)tetrahydro-2H-pyran-3,4-diyl diacetate (ST30Bn)

To a solution of 15 (28 g, 85 mmol) in dichloromethane (320 mL) were added powdered molsieves 4A (10 g) followed by stirring for 5 minutes. Then, 18 (26.6 g, 128 mmol, 1.5 equiv) was added and stirring was continued for another 15 minutes. Trimethylsilyl trifluoromethanesulfonate (9.26 mL, 51.0 mmol, 0.6 equiv) was added, via drop wise addition, over a period of 15 minutes. Stirring was continued at room temperature for 2 hours. The reaction mixture was filtered over a cotton plug followed by quenching with an ice-cold saturated aqueous NaHCO3 solution (300 mL). The layers were separated and extraction was performed twice more with dichloromethane (2×150 mL). The combined organic layers were washed with water (150 mL) and brine (150 mL) followed by drying over $Na_2SO_4$ and concentrating in vacuo. Purification was performed by flash column chromatography (20-100% EtOAc in heptane) to obtain ST30Bn as a colourless oil (25 g, yield 55%). $^1$H NMR (400 MHz, Chloroform-d) δ 7.38-7.27 (m, 5H), 5.43 (t, J=6.9 Hz, 1H), 5.38-5.27 (m, 2H), 4.71 (d, J=8.3 Hz, 1H), 4.50 (s, 2H), 4.21-4.07 (m, 2H), 3.96-3.81 (m, 3H), 3.47 (t, J=6.3 Hz, 3H), 2.14 (s, 3H), 2.05 (s, 3H), 2.00 (s, 3H), 1.94 (s, 3H), 1.68-1.51 (m, 4H), 1.44-1.30 (m, 4H).

(2R,3R,4R,5R,6R)-5-acetamido-2-(acetoxymethyl)-6-((6-hydroxyhexyl)oxy)tetrahydro-2H-pyran-3,4-diyl diacetate (ST30)

To a solution of ST30Bn (29 g, 54 mmol) in tetrahydrofuran (250 mL) and 2-Propanol (250 mL) was added 10% palladium on carbon (0.582 g, 0.547 mmol, 0.075 equiv). The flask was charged with hydrogen (atmospheric pressure) and stirring of the mixture was continued overnight at room temperature. The reaction mixture was filtered over a plug of kieselguhr and the filtrate was concentrated in vacuo. After stripping twice with toluene (2×200 mL) and dichloromethane (2×200 mL) ST30 was obtained as a colourless oil (24 g, yield 99%). $^1$H NMR (400 MHz, Methanol-$d_4$) δ 5.37-5.26 (m, 1H), 5.10-4.97 (m, 1H), 4.67-4.48 (m, 2H), 4.20-3.93 (m, 4H), 3.92-3.77 (m, 1H), 3.52 (hept, J=9.4, 8.1 Hz, 3H), 3.36-3.23 (m, 1H), 2.17-2.09 (m, 3H), 2.05-1.98 (m, 3H), 1.97-1.87 (m, 6H), 1.63-1.45 (m, 4H), 1.43-1.29 (m, 4H).

(2R,3R,4R,5R,6R)-5-acetamido-2-(acetoxymethyl)-6-((6-(((2-cyanoethoxy)(diisopropylamino)phosphino)oxy)hexyl)oxy)tetrahydro-2H-pyran-3,4-diyl diacetate (ST31)

To a solution of ST30 (21.2 g, 47.4 mmol) in dry dichloromethane (550 mL), under an argon atmosphere, was added DIPEA (83 mL, 474 mmol, 10 equiv) and Molsieves 4A (30 g). The reaction mixture was cooled to a temperature of 0° C. followed by the drop wise addition of 2-cyanoethyl N,N-diisopropylchlorophosphoramidite (13.46 g, 56.9 mmol, 1.2 equiv) over a period of 10 minutes. Stirring of the mixture was continued while allowing it to warm up over a period of 30 minutes. The reaction mixture was filtered over a cotton plug and directly coated on, with $Et_3N$ treated, silica (60 g). Purification was performed by flash column chromatography (10-60% EtOAc in heptane, 5% $Et_3N$) to obtain ST31 as a yellow tar (24.8 g, yield 78%). $^1$H NMR (400 MHz, DMSO-$d_6$) δ 7.82 (d, J=9.2 Hz, 1H), 5.21 (d, J=3.4 Hz, 1H), 4.96 (dd, J=11.3, 3.4 Hz, 1H), 4.48 (d, J=8.5 Hz, 1H), 4.02 (s, 3H), 3.91-3.81 (m, 1H), 3.79-3.63 (m, 3H), 3.63-3.49 (m, 4H), 3.45-3.37 (m, 1H), 2.76 (t, J=5.8 Hz, 2H), 2.10 (s, 3H), 2.00 (s, 3H), 1.89 (s, 3H), 1.77 (s, 3H), 1.58-1.40 (m, 4H), 1.37-1.22 (m, 4H), 1.13 (dd, J=6.8, 3.9 Hz, 12H).

Example 2

Synthesis of Trebler Synthons

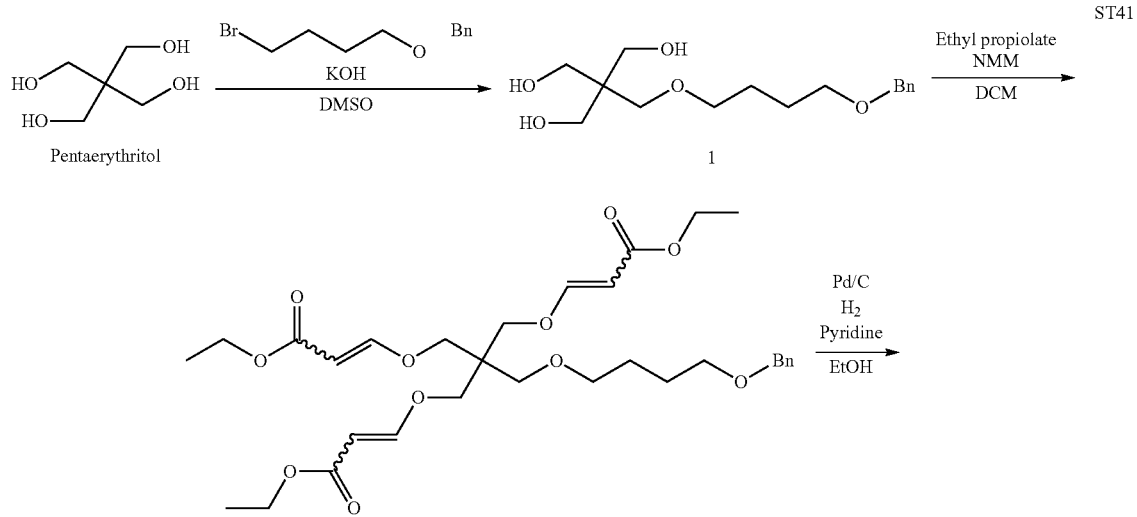

2

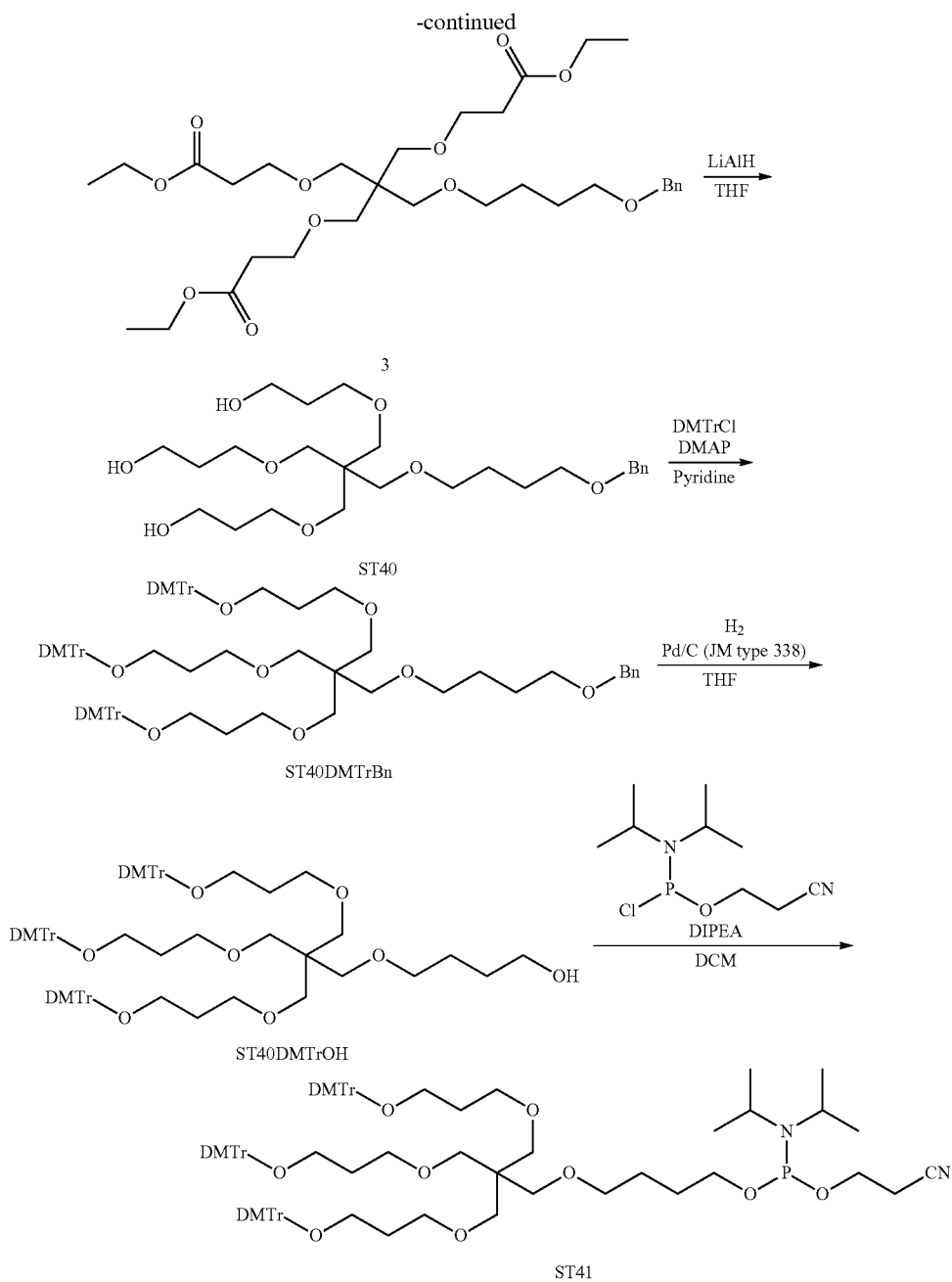

2-((4-(benzyloxy)butoxy)methyl)-2-(hydroxymethyl) propane-1,3-diol (1)

To a suspension of pentaerythritol (160 g, 1175 mmol, 10 equiv) in dimethyl sulfoxide (320 mL) was added potassium hydroxide (65.9 g, 1175 mmol, 10 equiv) followed by stirring for 15 minutes at room temperature. Then, over a period of 1.5 hours, was added a solution of 4-benzyloxy-1-bromobutane (22.32 mL, 118 mmol, 1 equiv) in dimethyl sulfoxide (107 mL). Upon complete addition, stirring of the reaction mixture was continued overnight at room temperature. The reaction mixture was acidified to pH=2 by the addition of 3M aqueous HCl, the now obtained white suspension was filtered over a glass filter. The filtrate was further diluted with water (900 mL), transferred to a separatory funnel and the product was extracted with dichloromethane (3×200 mL). The combined organic layers were washed with water (4×200 mL), dried over $Na_2SO_4$ and concentrated in vacuo. The pale yellow oil was purified by flash column chromatography (50-100% EtOAc in heptane) to obtain 1 as a colourless oil (20.46 gram, yield 58%). $^1$H NMR (400 MHz, Chloroform-d) δ 7.41-7.27 (m, 5H), 4.50 (s, 2H), 3.70 (s, 6H), 3.52-3.43 (m, 6H), 2.54 (s, 3H), 1.71-1.64 (m, 4H).

diethyl 3,3'-((2-((4-(benzyloxy)butoxy)methyl)-2-(((3-ethoxy-3-oxoprop-1-en-1-yl)oxy)methyl)propane-1,3-diyl)bis(oxy))diacrylate (2)

To a solution of 1 (20.46 g, 68.6 mmol) in dichloromethane (300 mL) was added N-methylmorpholine (33.9 mL, 309 mmol, 4.5 equiv). The reaction mixture was cooled upon an icebath and to the reaction mixture was added ethyl propiolate (27.8 mL, 274 mmol, 4 equiv) via a single stream. Stirring of the reaction mixture was continued for 15 minutes, followed by allowing the reaction mixture to warm up to room temperature. After 2 hours reaction time, the reaction mixture was concentrated in vacuo to obtain a dark brown oil. Purification of the crude material was performed by flash column chromatography (0-37% EtOAc in heptane) to obtain 2 as a yellow oil (31.56 g, yield 78%). $^1$H NMR (400 MHz, Chloroform-d) δ 7.54 (d, J=12.6 Hz, 3H), 7.39-7.28 (m, 5H), 5.23 (d, J=12.6 Hz, 3H), 4.50 (s, 2H), 4.16 (q, J=7.1 Hz, 6H), 3.87 (s, 6H), 3.53-3.33 (m, 6H), 1.69-1.55 (m, 4H), 1.26 (t, J=7.1 Hz, 12H).

diethyl 3,3'-((2-((4-(benzyloxy)butoxy)methyl)-2-((3-ethoxy-3-oxopropoxy)methyl)propane-1,3-diyl) bis(oxy))dipropanoate (3)

To a solution of 2 (31.56 g, 53.2 mmol) in ethanol (1463 mL) was added 10% palladium on carbon (2.83 g, 2.66 mmol, 0.05 equiv) and pyridine (2.153 mL, 26.6 mmol, 0.5 equiv). The reaction mixture was charged with hydrogen (atmospheric pressure) and stirring of the mixture was continued overnight at room temperature. The reaction mixture was filtered over a plug of kieselguhr, followed by concentrating the filtrate in vacuo. This afforded 3 as a yellow oil (29.75 g, yield 93%). $^1$H NMR (400 MHz, Chloroform-d) δ 7.38-7.27 (m, 5H), 4.51 (s, 2H), 4.13 (q, J=7.1 Hz, 6H), 3.64 (t, J=6.5 Hz, 6H), 3.48 (t, J=6.2 Hz, 2H), 3.39-3.33 (m, 8H), 3.30 (s, 2H), 2.52 (t, J=6.5 Hz, 6H), 1.70-1.56 (m, 4H), 1.26 (t, J=7.1 Hz, 9H).

3,3'-((2-((4-(benzyloxy)butoxy)methyl)-2-((3-hydroxypropoxy)methyl)propane-1,3-diyl)bis(oxy))bis (propan-1-ol) (ST40)

A solution of 2.4 M lithium aluminium hydride in tetrahydrofuran (76 mL, 183 mmol, 6.2 equiv) in dry tetrahydrofuran (331 mL) was cooled to a temperature of 0° C. Then, via drop wise addition, was added a solution of 3 (17.7 g, 29.6 mmol) in dry tetrahydrofuran (200 mL) at such a rate that the temperature was kept below 10° C. Upon complete addition stirring was continued overnight while allowing the reaction mixture to slowly reach room temperature. The reaction was further diluted with tetrahydrofuran (100 mL) and cooled to a temperature of 0° C. Quenching of the reaction mixture was performed by the slow addition of water (2.0 mL), 4M aqueous NaOH (2.0 mL) and water (6.0 mL). The white precipitate was removed by filtration over a dry Na$_2$SO$_4$ plug followed by rinsing twice with tetrahydrofuran. The filtrate was concentrated in vacuo and purification of this was performed by flash column chromatography (0-10% MeOH in dichloromethane) to obtain ST40 as a colourless oil (9.55 g, yield 68%). $^1$H NMR (400 MHz, Chloroform-d) δ 7.39-7.27 (m, 5H), 4.51 (s, 2H), 3.74 (q, J=5.2 Hz, 6H), 3.58 (t, J=5.5 Hz, 6H), 3.49 (t, J=6.1 Hz, 2H), 3.40 (s, 8H), 3.33 (s, 2H), 3.27 (s, 3H), 1.79 (p, J=5.3 Hz, 6H), 1.71-1.58 (m, 4H).

8,8-bis((3-(bis(4-methoxyphenyl)(phenyl)methoxy) propoxy)methyl)-1,1-bis(4-methoxyphenyl)-1,16-diphenyl-2,6,10,15-tetraoxahexadecane (ST40DMTrBn)

Residual water was removed from ST40 (9.55 g, 20.21 mmol) by stripping twice with pyridine, followed by redissolving in pyridine (464 mL) under an argon atmosphere. To the reaction mixture were added moleculair sieves 3A (20 g) and stirring was continued for 15 minutes. Solid DMTrCl (30.8 g, 91 mmol, 4.5 equiv) was added and stirring of the now dark orange mixture was continued overnight. The reaction was filtered over a cotton plug and the filtrate was coated on, with Et$_3$N neutralized, silica. Purification was performed by flash column chromatography (0-40% EtOAc in heptane, 5% Et$_3$N) to obtain ST40DMTrBn as a yellow foaming oil (25.3 g, yield 84%). $^1$H NMR (400 MHz, Chloroform-d) δ 7.43-7.37 (m, 6H), 7.33-7.21 (m, 23H), 7.19-7.13 (m, 3H), 6.82-6.75 (m, 12H), 4.46 (s, 2H), 3.74 (s, 18H), 3.43 (t, J=6.3 Hz, 2H), 3.39 (t, J=6.5 Hz, 6H), 3.26-3.17 (m, 10H), 3.06 (t, J=6.4 Hz, 6H), 1.78 (p, J=6.4 Hz, 6H), 1.64-1.49 (m, 4H).

4-(3-(3-(bis(4-methoxyphenyl)(phenyl)methoxy) propoxy)-2,2-bis((3-(bis(4-methoxyphenyl)(phenyl) methoxy)propoxy)methyl)propoxy)butan-1-ol (ST40DMTrOH)

To a solution of ST40DMTrBn (25.3 g, 18.34 mmol) in tetrahydrofuran (275 mL) was added 5% palladium on carbon, Johnson Matthey type 338 (5.85 g, 2.75 mmol, 0.15 equiv). The flask was charged with hydrogen (atmospheric pressure) and after 45 minutes reaction time it was flushed with nitrogen. The reaction mixture was filtered over a plug of kieselguhr and concentrated in vacuo. Purification was performed by flash column chromatography (0-40% EtOAc in heptane, 5% Et$_3$N) to obtain ST40DMTrOH as a white foaming solid (11.95 g, yield 50%). $^1$H NMR (400 MHz, Chloroform-d) δ 7.44-7.37 (m, 6H), 7.34-7.21 (m, 18H), 7.20-7.13 (m, 3H), 6.83-6.75 (m, 12H), 3.75 (s, 18H), 3.60-3.53 (m, 2H), 3.39 (t, J=6.4 Hz, 6H), 3.27 (t, 2H), 3.22 (s, 8H), 3.07 (t, J=6.4 Hz, 6H), 2.26 (t, J=5.9 Hz, 1H), 1.79 (p, J=6.5 Hz, 6H), 1.60-1.51 (m, 4H).

4-(3-(3-(bis(4-methoxyphenyl)(phenyl)methoxy) propoxy)-2,2-bis((3-(bis(4-methoxyphenyl)(phenyl) methoxy)propoxy)methyl)propoxy)butyl (2-cyanoethyl) diisopropylphosphoramidite (ST41)

To a solution of ST40DMtrOH (11.95 g, 9.27 mmol) in dry dichloromethane (162 mL) was added DIPEA (16.18 mL, 93 mmol, 10 equiv) and moleculair sieves 4A (25 g) followed by cooling to a temperature of 0° C. Then, to the reaction was added 2-cyanoethyl N,N-diisopropylchlorophosphoramidite (2.61 g, 11.03 mmol, 1.2 equiv) via drop wise addition over a period of 15 minutes. Stirring of the reaction mixture was continued for another 15 minutes while allowing it to reach room temperature. The reaction mixture was filtered over a cotton plug and the filtrate was coated on, with Et$_3$N treated, silica (50 g). Purification was performed by flash column chromatography (0-35% EtOAc in heptane, 5% Et$_3$N) to obtain ST41 as a colourless tar (10.65 g, yield 77%). $^1$H NMR (400 MHz, Chloroform-d) δ 7.44-7.37 (m, 6H), 7.33-7.21 (m, 18H), 7.20-7.13 (m, 3H), 6.83-6.75 (m, 12H), 3.86-3.70 (m, 20H), 3.67-3.50 (m, 4H), 3.39 (t, J=6.4 Hz, 6H), 3.29-3.16 (m, 10H), 3.06 (t, J=6.4 Hz, 6H), 2.57 (t, 2H), 1.78 (p, J=6.4 Hz, 6H), 1.65-1.49 (m, 4H), 1.16 (dd, J=9.1, 6.8 Hz, 12H).

ST43
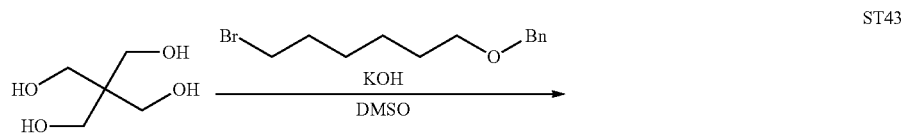
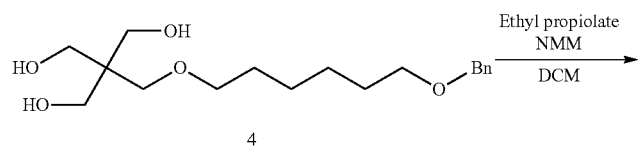
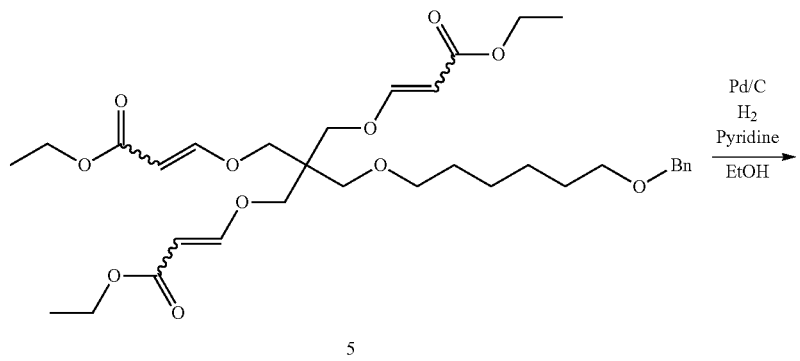
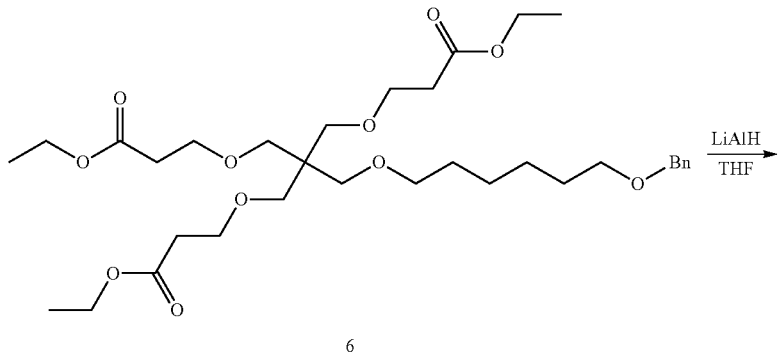
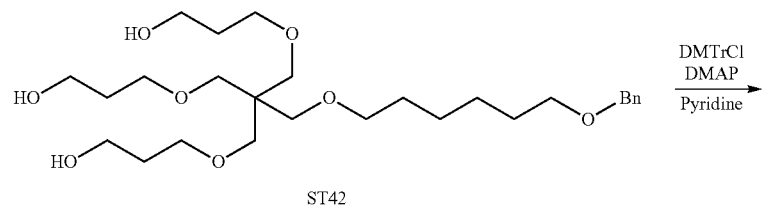
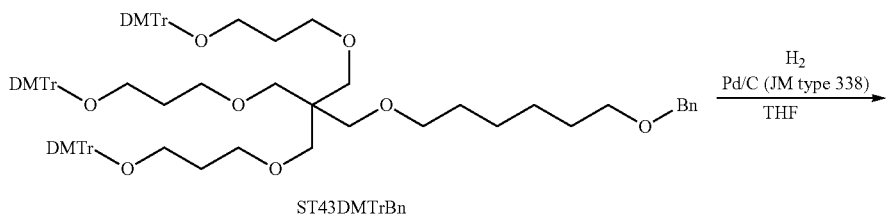

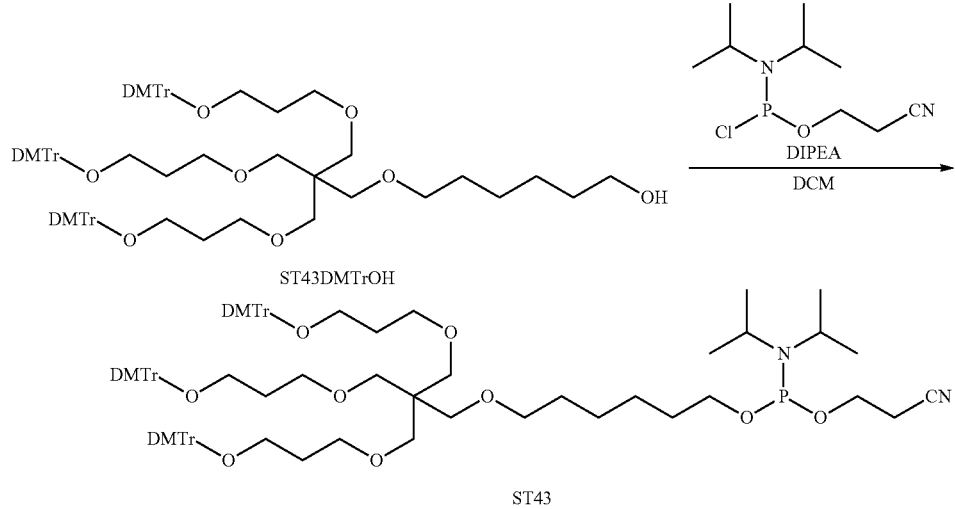

2-(((6-(benzyloxy)hexyl)oxy)methyl)-2-(hydroxymethyl)propane-1,3-diol (4)

To a suspension of pentaerythritol (55.2 g, 406 mmol, 10 equiv) in dimethyl sulfoxide (110 mL) was added potassium hydroxide (22.76 g, 406 mmol, 10 equiv) followed by stirring for 15 minutes at room temperature. Then, over a period of 1.5 hours, was added a solution of benzyl 6-bromohexyl ether (11 g, 40.6 mmol, 1 equiv) in dimethyl sulfoxide (36.6 mL). Upon complete addition, stirring of the reaction mixture was continued overnight at room temperature. The reaction mixture was acidified to pH~1 by the addition of 3M aqueous HCl and the now obtained white emulsion was further diluted with water (700 mL), transferred to a separatory funnel and the product was extracted with dichloromethane (4×70 mL). The combined organic layers were washed with water (3×70 mL), dried over $Na_2SO_4$ and concentrated in vacuo. The pale yellow oil was purified by flash column chromatography (50-100% EtOAc in heptane) to obtain 4 as a colourless oil (9.16 gram, yield 67%). $^1$H NMR (400 MHz, Chloroform-d) δ 7.38-7.27 (m, 5H), 4.50 (s, 2H), 3.70 (s, 6H), 3.49-3.39 (m, 6H), 2.83 (s, 3H), 1.66-1.52 (m, 4H), 1.45-1.28 (m, 4H).

diethyl 3,3'-((2-(((6-(benzyloxy)hexyl)oxy)methyl)-2-(((3-ethoxy-3-oxoprop-1-en-1-yl)oxy)methyl)propane-1,3-diyl)bis(oxy))diacrylate (5)

To a solution of 2 (9.1 g, 27.9 mmol) in dichloromethane (150 mL) was added N-methylmorpholine (13.79 mL, 125 mmol, 4.5 equiv). The reaction mixture was cooled upon an icebath and to the reaction mixture was added ethyl propiolate (11.30 mL, 112 mmol, 4 equiv) via a single stream. Stirring of the reaction mixture was continued for 15 minutes, followed by allowing the reaction mixture to warm up to room temperature. After 2 hours reaction time, the reaction mixture was concentrated in vacuo to obtain a dark brown oil. Purification of the crude material was performed by flash column chromatography (0-30% EtOAc in heptane) to obtain 5 as a pale yellow oil (15.85 g, yield 79%). $^1$H NMR (400 MHz, Chloroform-d) δ 7.54 (d, J=12.6 Hz, 3H), 7.37-7.27 (m, 5H), 5.23 (d, J=12.6 Hz, 3H), 4.50 (s, 2H), 4.16 (q, J=7.1 Hz, 6H), 3.88 (s, 6H), 3.46 (t, J=6.5 Hz, 2H), 3.41 (s, 2H), 3.36 (t, J=6.5 Hz, 2H), 1.65-1.49 (m, 4H), 1.43-1.21 (m, 13H).

diethyl 3,3'-((2-(((6-(benzyloxy)hexyl)oxy)methyl)-2-((3-ethoxy-3-oxopropoxy)methyl)propane-1,3-diyl)bis(oxy))dipropanoate (6)

To a solution of 5 (15.85 g, 25.5 mmol) in ethanol (750 mL) was added 10% palladium on carbon (1.359 g, 1.277 mmol, 0.05 equiv) and pyridine (1.033 mL, 12.77 mmol, 0.5 equiv). The reaction mixture was charged with hydrogen (atmospheric pressure) and stirring of this was continued overnight at room temperature. The reaction mixture was filtered over a plug of kieselguhr followed by concentrating the filtrate in vacuo which afforded 6 as a pale yellow oil (15.27 g, yield 91%). $^1$H NMR (400 MHz, Chloroform-d) δ 7.37-7.27 (m, 5H), 4.50 (s, 2H), 4.14 (q, J=7.1 Hz, 6H), 3.64 (t, J=6.5 Hz, 6H), 3.47 (t, J=6.7 Hz, 2H), 3.40-3.26 (m, 10H), 2.52 (t, J=6.5 Hz, 6H), 1.69-1.46 (m, 4H), 1.44-1.30 (m, 4H), 1.26 (t, J=7.1 Hz, 9H).

3,3'-((2-(((6-(benzyloxy)hexyl)oxy)methyl)-2-((3-hydroxypropoxy)methyl)propane-1,3-diyl)bis(oxy))bis(propan-1-ol) (ST42)

A solution of 6 (19.27 g, 30.7 mmol) in dry tetrahydrofuran (360 mL) was cooled to a temperature of 0° C. Then, via drop wise addition, was added 2.4 M lithium aluminium hydride in tetrahydrofuran (128 mL, 307 mmol, 10 equiv) over a period of 1 hour. Upon complete addition, stirring was continued overnight while allowing the reaction mixture to slowly reach room temperature. Upon cooling, the reaction was quenched by the slow addition of water (11.7 mL), 4M aqueous NaOH (11.7 mL) and water (35 mL). The white precipitate was removed by filtration over a dry $Na_2SO_4$ plug followed by rinsing twice with tetrahydrofuran. The filtrate was concentrated in vacuo and purification was performed by flash column chromatography (0-6% MeOH in dichloromethane) to obtain ST42 as a colourless oil (11.64 g, yield 72%). $^1$H NMR (400 MHz, Chloroform-d) δ 7.38-7.27 (m, 5H), 4.50 (s, 2H), 3.74 (t, J=5.4 Hz, 6H), 3.58 (t, J=5.5 Hz, 6H), 3.47 (t, J=6.6 Hz, 2H), 3.40 (s, 6H), 3.36 (t, J=6.5 Hz, 2H), 3.32 (s, 2H), 3.29 (s, 3H), 1.79 (p, J=5.4 Hz, 6H), 1.70-1.49 (m, 4H), 1.44-1.28 (m, 4H).

8,8-bis((3-(bis(4-methoxyphenyl)(phenyl)methoxy) propoxy)methyl)-1,1-bis(4-methoxyphenyl)-1,18-diphenyl-2,6,10,17-tetraoxaoctadecane (ST43DMTrBn)

Residual water was removed from ST42 (4.00 g, 7.99 mmol) by stripping twice with pyridine, followed by redissolving in pyridine (165 mL) under an argon atmosphere. To the reaction mixture were added moleculair sieves 4A (8 g) and stirring was continued for 15 minutes. Solid DMTrCl (13.54 g, 39.9 mmol, 5 equiv) was added and stirring of the now dark orange mixture was continued at room temperature. After 2 hours additional DMTrCl (4.06 g, 11.98 mmol, 1.5 equiv) was added and stirring was continued overnight. The reaction was filtered over a cotton plug and the filtrate was coated on, with $Et_3N$ neutralized, silica (40 g). Purification was performed by flash column chromatography (0-35% EtOAc in heptane, 5% $Et_3N$) to obtain ST43DMTrBn as a yellow foaming oil (10.44 g, yield 86%). $^1$H NMR (400 MHz, Chloroform-d) δ 7.43-7.37 (m, 6H), 7.34-7.21 (m, 23H), 7.19-7.12 (m, 3H), 6.82-6.76 (m, 12H), 4.47 (s, 2H), 3.74 (s, 18H), 3.41 (dt, J=14.6, 6.5 Hz, 8H), 3.26-3.16 (m, 10H), 3.06 (t, J=6.4 Hz, 6H), 1.78 (p, J=6.5 Hz, 6H), 1.56 (p, 2H), 1.45 (p, J=6.6 Hz, 2H), 1.38-1.21 (m, 4H).

6-(3-(3-(bis(4-methoxyphenyl)(phenyl)methoxy) propoxy)-2,2-bis((3-(bis(4-methoxyphenyl)(phenyl) methoxy)propoxy)methyl)propoxy)hexan-1-ol (ST43DMTrOH)

To a solution of ST43DMTrBn (10.2 g, 7.25 mmol) in tetrahydrofuran (200 mL) was added 5% palladium on carbon, Johnson Matthey type 338 (2.313 g, 1.08 mmol, 0.15 equiv). The flask was charged with hydrogen (atmospheric pressure) and after 50 minutes reaction time it was flushed with nitrogen. The reaction mixture was filtered over a plug of Kieselguhr and concentrated in vacuo. Purification was performed by flash column chromatography (0-40% EtOAc in heptane, 5% $Et_3N$) to obtain ST43DMTrOH as a white foam (3.83 g, yield 38%). $^1$H NMR (400 MHz, Chloroform-d) δ 7.44-7.36 (m, 6H), 7.34-7.21 (m, 18H), 7.20-7.13 (m, 3H), 6.84-6.73 (m, 12H), 3.75 (s, 18H), 3.62-3.53 (m, 2H), 3.40 (t, J=6.4 Hz, 6H), 3.27-3.16 (m, 10H), 3.07 (t, J=6.4 Hz, 6H), 1.79 (p, J=6.4 Hz, 6H), 1.56-1.41 (m, 4H), 1.37-1.23 (m, 5H).

6-(3-(3-(bis(4-methoxyphenyl)(phenyl)methoxy) propoxy)-2,2-bis((3-(bis(4-methoxyphenyl)(phenyl) methoxy)propoxy)methyl)propoxy)hexyl (2-cyanoethyl) diisopropylphosphoramidite (ST43)

To a solution of ST43DMtrOH (3.83 g, 2.76 mmol) in dry dichloromethane (50 mL) was added DIPEA (4.82 mL, 27.6 mmol, 10 equiv) and moleculair sieves 4A (7 g) followed by cooling to a temperature of 0° C. Then, to the reaction was added 2-cyanoethyl N,N-diisopropylchlorophosphoramidite (0.948 g, 4.00 mmol, 1.45 equiv) via drop wise addition over a period of 15 minutes. Stirring of the reaction mixture was continued for another 15 minutes while allowing it to reach room temperature. The reaction mixture was filtered over a cotton plug and the filtrate was coated on, with $Et_3N$ treated, silica (10 g). Purification was performed by flash column chromatography (0-30% EtOAc in heptane, 5% $Et_3N$) to obtain ST43 as a colourless tar (3.48 g, yield 83%). $^1$H NMR (400 MHz, Chloroform-d) δ 7.44-7.37 (m, 6H), 7.33-7.20 (m, 18H), 7.19-7.13 (m, 3H), 6.83-6.75 (m, 12H), 3.87-3.69 (m, 20H), 3.66-3.51 (m, 4H), 3.39 (t, J=6.4 Hz, 6H), 3.28-3.15 (m, 10H), 3.07 (t, J=6.4 Hz, 6H), 2.60 (t, J=6.5 Hz, 2H), 1.79 (p, J=6.4 Hz, 6H), 1.58 (p, J=3.9 Hz, 2H), 1.46 (p, J=6.7 Hz, 2H), 1.39-1.23 (m, 4H), 1.17 (t, J=7.3 Hz, 12H).

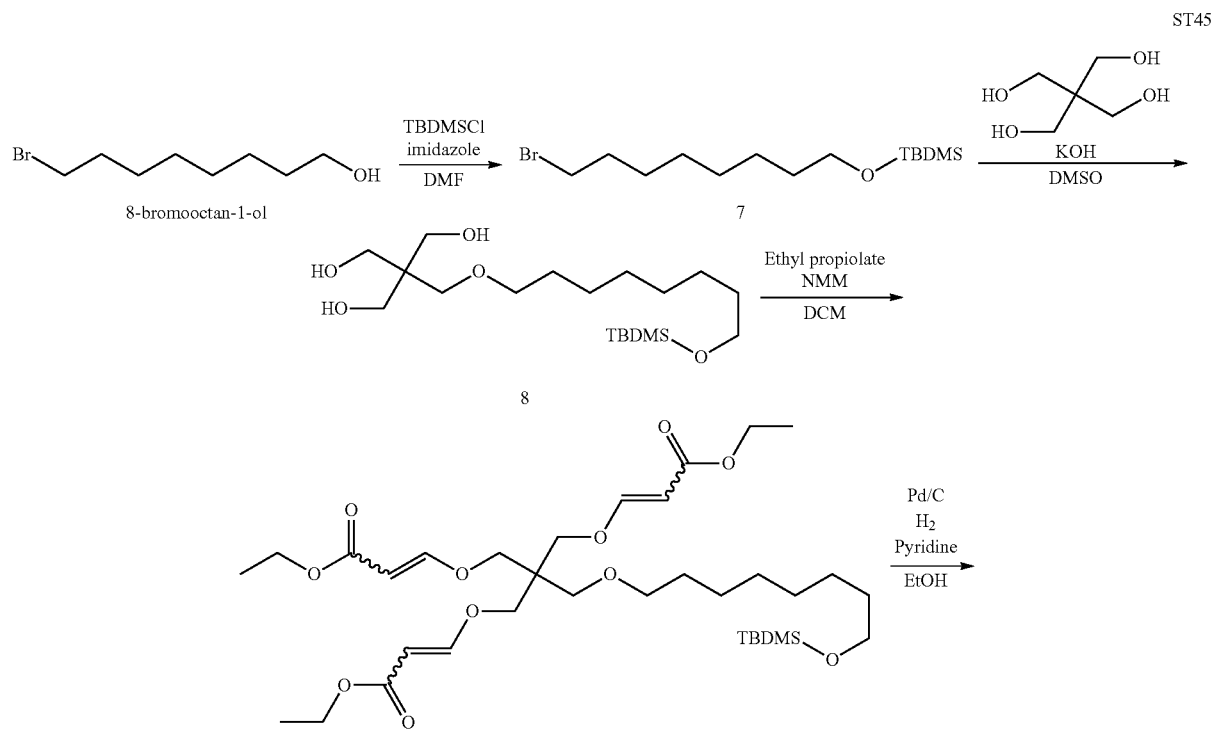

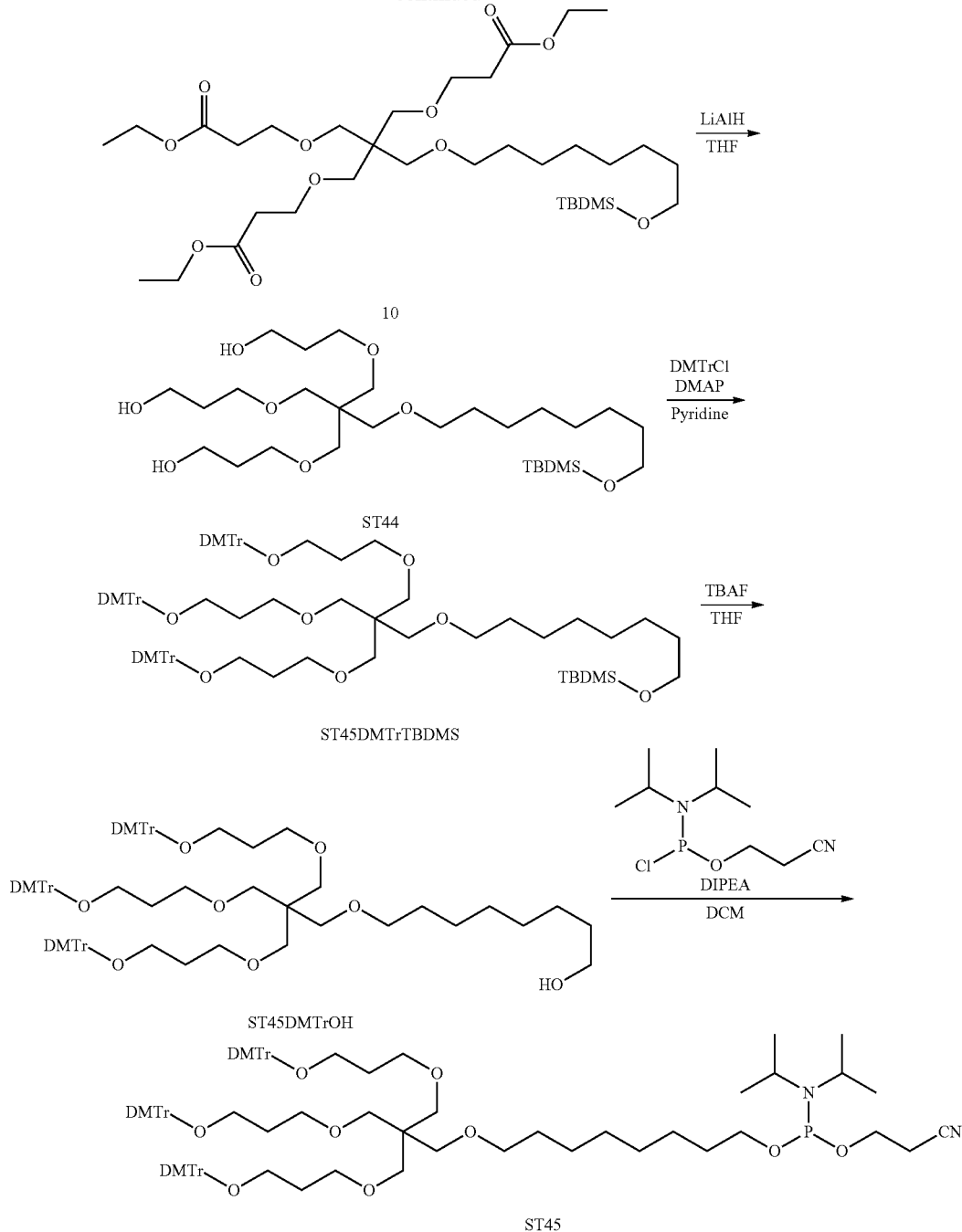

((8-bromooctyl)oxy)(tert-butyl)dimethylsilane (7)

To a solution of 8-bromooctan-1-ol (8 g, 38.3 mmol) in dry N,N-dimethylformamide (10 mL) was added imidazole (6.51 g, 96 mmol, 2.5 equiv). Once a clear solution was obtained, TBDMS-Cl (7.50 g, 49.7 mmol, 1.2 equiv) was added portion wise to observe an exothermic reaction which reached a maximum temperature of 40° C. Stirring of the reaction mixture was continued overnight at room temperature. The obtained yellow suspension was diluted with Et$_2$O (40 mL) and washed with brine (40 mL). The aqueous layer was extracted twice more with Et$_2$O (2×40 mL) and the combined organic layers were dried over Na$_2$SO$_4$. After concentrating in vacuo, purification was performed by flash column chromatography (0-40% EtOAc in heptane) to obtain 7 as a colourless oil (11.73 g, yield 95%). $^1$H NMR (400 MHz, Chloroform-d) δ 3.60 (t, J=6.6, 1.7 Hz, 2H), 3.41 (t, J=6.9 Hz, 2H), 1.85 (p, J=7.0 Hz, 2H), 1.60-1.37 (m, 4H), 1.37-1.24 (m, 6H), 0.89 (s, 9H), 0.05 (s, 6H).

2-(((8-((tert-butyldimethylsilyl)oxy)octyl)oxy)methyl)-2-(hydroxymethyl)propane-1,3-diol (8)

To a suspension of pentaerythritol (16.84 g, 124 mmol, 10 equiv) in dimethyl sulfoxide (45 mL) was added potassium hydroxide (6.94 g, 124 mmol, 10 equiv) and this was stirred for 15 minutes at room temperature. Then, over a period of 2 hours, was added 7 (4 g, 12.37 mmol, 1 equiv). Upon complete addition, stirring of the reaction mixture was continued overnight at room temperature. The reaction mixture was extracted three times with Et$_2$O (3×150 mL) and all organic layers were washed separately with brine (50 mL). The combined aqueous layers were then extracted once more with Et$_2$O (50 mL). The combined organic layers were dried over Na$_2$SO$_4$ and concentrated in vacuo. The pale yellow oil was purified by flash column chromatography (0-100% EtOAc in heptane) to obtain 8 as a colourless oil (0.53 g, yield 11%). $^1$H NMR (400 MHz, Chloroform-d) δ 3.72 (d, J=3.7 Hz, 6H), 3.60 (t, J=6.6 Hz, 2H), 3.47 (s, 2H), 3.42 (t, J=6.5 Hz, 2H), 2.73 (s, 3H), 1.63-1.44 (m, 4H), 1.30 (s, 8H), 0.89 (s, 9H), 0.05 (s, 6H).

ethyl 15,15-bis(((3-ethoxy-3-oxoprop-1-en-1-yl)oxy)methyl)-2,2,3,3-tetramethyl-4,13,17-trioxa-3-silaicos-18-en-20-oate (9)

To a solution of 8 (2.94 g, 7.76 mmol) in dichloromethane (30 mL) was added N-methylmorpholine (3.84 mL, 34.9 mmol, 4.5 equiv) and ethyl propiolate (3.7 mL, 36.5 mmol, 4.7 equiv). An exothermic reaction was observed and it was cooled back to a temperature of 20° C. with the use of an ice bath. Stirring of the reaction mixture was continued overnight at room temperature. The reaction mixture was concentrated in vacuo to obtain a dark brown oil. Purification of this was performed by flash column chromatography (0-40% EtOAc in heptane) to obtain 9 as a pale yellow oil (3.84 g, yield 73%). $^1$H NMR (400 MHz, Chloroform-d) δ 7.54 (d, J=12.6 Hz, 3H), 5.23 (d, J=12.6 Hz, 3H), 4.16 (q, J=7.1 Hz, 6H), 3.89 (s, 6H), 3.59 (t, J=6.6 Hz, 2H), 3.42 (s, 2H), 3.36 (t, J=6.5 Hz, 2H), 1.56-1.45 (m, 4H), 1.35-1.22 (m, 17H), 0.89 (s, 9H), 0.05 (s, 6H).

ethyl 15,15-bis((3-ethoxy-3-oxopropoxy)methyl)-2,2,3,3-tetramethyl-4,13,17-trioxa-3-silaicosan-20-oate (10)

To a solution of 9 (3.84 g, 5.71 mmol) in ethanol (167 mL) was added 10% palladium on carbon (0.304 g, 0.285 mmol, 0.05 equiv) and pyridine (0.213 mL, 2.85 mmol, 0.5 equiv). The reaction mixture was charged with hydrogen (atmospheric pressure) and stirring of the mixture was continued overnight at room temperature. The reaction mixture was filtered over a plug of kieselguhr followed by concentrating the filtrate in vacuo, which afforded 10 as a yellow oil (3.86 g, yield 100%). $^1$H NMR (400 MHz, Chloroform-d) δ 4.14 (q, J=7.1 Hz, 6H), 3.64 (t, J=6.5 Hz, 6H), 3.59 (t, J=6.7 Hz, 2H), 3.40-3.28 (m, 10H), 2.53 (t, J=6.5 Hz, 6H), 1.55-1.46 (m, 4H), 1.35-1.23 (m, 17H), 0.89 (s, 9H), 0.05 (s, 6H).

15,15-bis((3-hydroxypropoxy)methyl)-2,2,3,3-tetramethyl-4,13,17-trioxa-3-silaicosan-20-ol (ST44)

A solution of 10 (3.86 g, 5.69 mmol) in dry tetrahydrofuran (67 mL) was cooled to a temperature of −5° C. Then, via drop wise addition, was added 2.4 M lithium aluminium hydride in tetrahydrofuran (24 mL, 57 mmol, 10 equiv) over a period of 1 hour. Upon complete addition stirring was continued overnight while allowing the reaction mixture to slowly reach room temperature. The next day, the reaction mixture was cooled to a temperature of 0° C. and was quenched by the batch wise addition of sodium sulfate decahydrate (18.32 g, 56.9 mmol, 10 equiv). The white precipitate was removed by filtration over a dry Na$_2$SO$_4$ plug followed by rinsing twice with tetrahydrofuran. The filtrate was concentrated in vacuo and purification was performed by flash column chromatography (0-7% MeOH in dichloromethane) to obtain ST44 as a pale yellow oil (1.96 g, yield 60%). $^1$H NMR (400 MHz, Chloroform-d) δ 3.75 (t, J=5.3 Hz, 6H), 3.64-3.55 (m, 8H), 3.48-3.27 (m, 13H), 1.80 (h, J=5.4, 4.8 Hz, 6H), 1.58-1.46 (m, 4H), 1.36-1.25 (m, 8H), 0.89 (s, 9H), 0.05 (s, 6H).

8,8-bis((3-(bis(4-methoxyphenyl)(phenyl)methoxy)propoxy)methyl)-1,1-bis(4-methoxyphenyl)-20,20,21,21-tetramethyl-1-phenyl-2,6,10,19-tetraoxa-20-siladocosane (ST45DMTrTBDMS)

Residual water was removed from ST44 (1.94 g, 3.51 mmol) by stripping twice with pyridine, followed by redissolving in pyridine (70 mL) under an argon atmosphere. To the reaction mixture were added moleculair sieves 4A (4 g) and stirring was continued for 15 minutes. Solid DMTrCl (4.16 g, 12.28 mmol, 3.5 equiv) was added in batches over a period of two hours. After another 1.5 hours additional DMTrCl (2.38 g, 7.02 mmol, 2 equiv) was added and stirring of the now dark orange mixture was continued overnight at room temperature. The reaction was quenched by the addition of MeOH (4.4 mL, 109 mmol, 31 equiv) and it was stirred for 15 minutes. Then, the reaction mixture was filtered over a cotton plug and the filtrate was coated on, with Et$_3$N neutralized, silica (20 g). Purification was performed by flash column chromatography (0-100% EtOAc in heptane, 5% Et$_3$N) to obtain ST45DMTrTBDMS as a yellow foaming oil (0.44 g, yield 8%). Starting material and intermediates were recovered in a 60% yield. $^1$H NMR (400 MHz, Chloroform-d) δ 7.43-7.38 (m, 6H), 7.27 (q, J=8.1, 7.3 Hz, 18H), 7.19-7.13 (m, 3H), 6.81-6.76 (m, 12H), 3.76 (s, 18H), 3.58 (td, J=6.5, 3.0 Hz, 2H), 3.44 (dt, J=33.9, 6.4 Hz, 6H), 3.35-3.16 (m, 10H), 3.07 (t, J=6.4 Hz, 6H), 1.79 (h, J=6.3 Hz, 6H), 1.52-1.39 (m, 4H), 1.34-1.20 (m, 8H), 0.89 (s, 9H), 0.04 (s, 6H).

8-(3-(3-(bis(4-methoxyphenyl)(phenyl)methoxy)propoxy)-2,2-bis((3-(bis(4-methoxyphenyl)(phenyl)methoxy)propoxy)methyl)propoxy)octan-1-ol (ST45DMTrOH)

To a solution of ST45DMTrTBDMS (2.20 g, 1.507 mmol) in dry tetrahydrofuran (12 mL) was added 1M TBAF in tetrahydrofuran (1.688 mL, 1.688 mmol, 1.12 equiv) and this was stirred at room temperature overnight. The reaction mixture was concentrated in vacuo and purification was performed by flash column chromatography (0-100% EtOAc in heptane, 5% Et$_3$N) to obtain ST45DMTrOH as a colourless oil (1.74 g, yield 83%). $^1$H NMR (400 MHz, Chloroform-d) δ 7.44-7.37 (m, 6H), 7.34-7.21 (m, 18H), 7.20-7.12 (m, 3H), 6.82-6.75 (m, 12H), 3.75 (s, 18H), 3.59 (q, J=6.5 Hz, 2H), 3.40 (t, J=6.5 Hz, 6H), 3.26-3.15 (m, 10H), 3.07 (t, J=6.4 Hz, 6H), 1.79 (p, J=6.4 Hz, 6H), 1.56-1.39 (m, 4H), 1.37-1.20 (m, 9H).

8-(3-(3-(bis(4-methoxyphenyl)(phenyl)methoxy)
propoxy)-2,2-bis((3-(bis(4-methoxyphenyl)(phenyl)
methoxy)propoxy)methyl)propoxy)octyl (2-cyano-
ethyl) diisopropylphosphoramidite (ST45)

To a solution of ST45DMtrOH (1.9 g, 1.412 mmol) in dry dichloromethane (25 mL) was added DIPEA (2.466 mL, 14.12 mmol, 10 equiv) and moleculair sieves 4A (3.8 g) followed by cooling to a temperature of 0° C. Then, to the reaction was added 2-cyanoethyl N,N-diisopropylchlorophosphoramidite (0.401 g, 1.694 mmol, 1.2 equiv) via drop wise addition over a period of 5 minutes. Stirring of the reaction mixture was continued for another 15 minutes while allowing it to reach room temperature. The reaction mixture was filtered over a cotton plug and the filtrate was coated on, with Et$_3$N treated, silica (7.5 g). Purification was performed by flash column chromatography (0-100% EtOAc in heptane, 5% Et$_3$N) to obtain ST45 as a clear oil (1.37 g, yield 59%). $^1$H NMR (400 MHz, Chloroform-d) δ 7.44-7.37 (m, 6H), 7.33-7.20 (m, 18H), 7.19-7.13 (m, 3H), 6.82-6.74 (m, 12H), 3.88-3.70 (m, 20H), 3.68-3.52 (m, 4H), 3.39 (t, J=6.4 Hz, 6H), 3.30-3.15 (m, 10H), 3.07 (t, J=6.4 Hz, 6H), 2.61 (t, J=6.6 Hz, 2H), 1.79 (h, J=6.5, 5.9 Hz, 6H), 1.63-1.54 (m, 2H), 1.50-1.40 (m, 2H), 1.37-1.21 (m, 8H), 1.17 (t, J=6.4 Hz, 12H).

Example 3

Synthesis of Nucleic Acid Conjugates

All Oligonucleotides were synthesized on an AKTA oligopilot synthesizer. Commercially available solid support and 2'-O-Methyl RNA phosphoramidites, 2'Fluoro, 2'Deoxy RNA phosphoramidites and commercially available long trebler phosphoramidite (STKS) (Glen research) were used. Oligonucleotide synthesis, deprotection and purification followed standard procedures that are known in the art. Oligonucleotide and oligonucleotide conjugate synthesis was performed by a commercial oligonucleotide manufacturer (Biospring, Frankfurt, Germany).

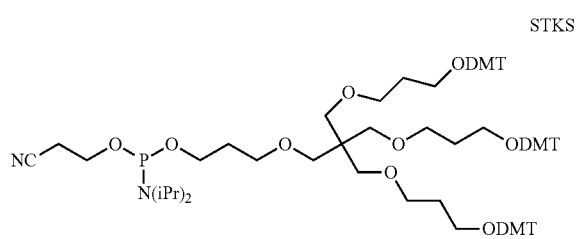

STKS

Conjugation of the GalNAc synthons (ST21, ST23, ST31) or trebler synthons (STKS, ST41, ST43, ST45) was achieved by coupling of the respective phosphoramidite to the 5' end of the oligochain under standard phosphoramidite coupling conditions. Phosphorothioates were introduced using standard commercially available thiolation reagents (EDITH, Link technologies).

The single strands were cleaved off the CPG by using aqueous Methylamine and the resulting crude oligonucleotide was purified by Ionexchange chromatography (Resource Q, 6 mL, GE Healthcare) on a AKTA Pure HPLC System using a Sodium chloride gradient. Product containing fractions were pooled, desalted on a size exclusion column (Zetadex, EMP Biotech) and lyophilised.

For Duplexation, equimolar amounts of the respective single strands were dissolved in water and heated to 80° C. for 5 min. After cooling the resulting Duplex was lyophilised.

TABLE 2

Mass spectrometry data for oligonucleotides

| Oligonucleotide | MS found | MS calculated |
|---|---|---|
| antisense strand (TTR and STS016) | 6943 Da | 6943.33 Da |
| TTR CF02 sense strand | 8603.17 Da | 8604 Da |
| TTR CF02V20 sense strand | 8490.38 Da | 8490.62 Da |
| TTR CF02V21 sense strand | 8554.87 Da | 8554.62 Da |
| TTR CF02V22 sense strand | 8310.02 Da | 8310.47 Da |
| TTR CF02V23 sense strand | 8374.13 Da | 8374.47 Da |
| STS016 L4 sense strand | 8388 Da | 8388.47 Da |
| STS016 L5 sense strand | 8471 Da | 8472.47 Da |
| STS016 L6 sense strand | 8415 Da | 8416.47 Da |
| STS016 L7 sense strand | 8500 Da | 8500.47 Da |
| STS016 L8 sense strand | 8444 Da | 8444.47 Da |
| STS016 L9 sense strand | 8528 Da | 8528.47 Da |
| GN_Luc antisense | 6260 Da | 6259.93 Da |
| GN_Luc sense | 7799 Da | 7800.21 Da |
| GN_PTENV10F antisense | 6320.43 Da | 6318 Da |
| GN_PTENV10F sense | 7727.24 Da | 7727.17 Da |

Synthesis of Comparative Nucleic Acid Conjugate
Molecule—TTR CF02

Oligonucleotide sequence:

```
Antisense strand
5'u(ps)u(ps)a uag agc aag aac acu g(ps)u(ps)u 3'

Sense strand
3'aminohexyl aau auc ucg uuc uug uga c(ps)a(ps)a 5'
```

Modifications key:

bold=2'OMe ribonucleotide underline=2'F/2'deoxyribonucleotide ps=phosphorothioate The sense strand was modified postsynthetically with an activated ester (NHS) of the GalNAc linker ST13:

ST13

The synthesis of ST13 and coupling was performed similar to published procedures (Ostergaard, Bioconjug Chem. 2015 Aug. 19; 26(8):1451-5), with the difference that NHS was used instead of PFP active ester.

Structure of the final conjugate (TTR CF02):

Sequences:
Modifications key for the following sequences:
bold=2'O-Methyl ribonucleotide
underline=2'Fluoro/2'deoxyribonucleotide
ps=phosphorothioate linkage TTR CF02:
Antisense strand
5'u(ps)u(ps)a uag agc aag aac acu g(ps)u(ps)u 3'

Sense strand
3'ST13 aminohexyl aau auc ucg uuc uug uga c(ps)a(ps)a 5'

TTR CF02V20
Antisense strand
5'u(ps)u(ps)a uag agc aag aac acu g(ps)u(ps)u 3'

Sense strand
3'a(ps)a(ps)u auc ucg uuc uug uga caa STKS (ST21)₃ 5'

TTR CF02V21
Antisense strand
5'u(ps)u(ps)a uag agc aag aac acu g(ps)u(ps)u 3'

Sense strand
3'a(ps)a(ps)u auc ucg uuc uug uga caa (ps) STKS (ps) (ST21)₃ 5'

TTR CF02V22
Antisense strand
5'u(ps)u(ps)a uag agc aag aac acu g(ps)u(ps)u 3'

Sense strand
3'a(ps)a(ps)u auc ucg uuc uug uga caa STKS (ST23)₃ 5'

TTR CF02V23
Antisense strand
5'u(ps)u(ps)a uag agc aag aac acu g(ps)u(ps)u 3'

Sense strand
3'a(ps)a(ps)u auc ucg uuc uug uga caa (ps) STKS (ps) (ST23)₃ 5'

Modifications key for the following sequences:

f denotes 2'Fluoro 2'deoxyribonucleotide m denotes 2'O Methyl ribonucleotide (ps) denotes phosphorothioate linkage STS016-L4
Antisense strand:
5' mU (ps) fU (ps) mA fU mA fG mA fG mC fA mA fG mA fA mC fA mC fU mG (ps) fU (ps) mU 3'

Sense strand:
5' (ST23 (ps))₃ ST41 (ps) fA mA fC mA fG mU fG mU fU mC fU mU fG mC fU mC fU mA fU (ps) mA (ps) fA 3'

STS016-L5
Antisense strand:
5' mU (ps) fU (ps) mA fU mA fG mA fG mC fA mA fG mA fA mC fA mC fU mG (ps) fU (ps) mU 3'

Sense strand:
5' (ST31 (ps))3 ST41 (ps) fA mA fC mA fG mU fG mU fU mC fU mU fG mC fU mC fU mA fU (ps) mA (ps) fA 3'

STS016-L6
Antisense strand:
5' mU (ps) fU (ps) mA fU mA fG mA fG mC fA mA fG mA fA mC fA mC fU mG (ps) fU (ps) mU 3'

Sense strand:
5' (ST23 (ps))₃ ST43 (ps) fA mA fC mA fG mU fG mU fU mC fU mU fG mC fU mC fU mA fU (ps) mA (ps) fA 3'

STS016-L7
Antisense strand:
5' mU (ps) fU (ps) mA fU mA fG mA fG mC fA mA fG mA fA mC fA mC fU mG (ps) fU (ps) mU 3'

Sense strand:
5' (ST31 (ps))₃ ST43 (ps) fA mA fC mA fG mU fG mU fU mC fU mU fG mC fU mC fU mA fU (ps) mA (ps) fA 3'

STS016-L8
Antisense strand:
5' mU (ps) fU (ps) mA fU mA fG mA fG mC fA mA fG mA fA mC fA mC fU mG (ps) fU (ps) mU 3'

Sense strand:
5' (ST23 (ps))₃ ST45 (ps) fA mA fC mA fG mU fG mU fU mC fU mU fG mC fU mC fU mA fU (ps) mA (ps) fA STS016-L9
Antisense strand:
5' mU (ps) fU (ps) mA fU mA fG mA fG mC fA mA fG mA fA mC fA mC fU mG (ps) fU (ps) mU 3'

Sense strand:
5' (ST31 (ps))₃ ST45 (ps) fA mA fC mA fG mU fG mU fU mC fU mU fG mC fU mC fU mA fU (ps) mA (ps) fA 3'

GN_Luc (non targeting control)
Antisense strand:
5'mU (ps)fC(ps)mGfAmAfGmUfAmUfUmCfCmGfCmGfUmA (ps)

fC(ps)mG 3'

Sense strand:
5' (ST23(ps))₃ STKS (ps) fCmGfUmAfCmGfCmGfGmAfAmUfAm

CfUmUfC (ps)mG (ps)fA 3'

GN_PTENV10F
Antisense
5'mU(ps)fA(ps)fAmGfUmUmCfUmAfGmCfUmGfUmGfGmU(ps)fG (ps)mG 3'

Sense
5' (ST23(ps))₃ STKS (ps) fCmCfAmCfCmAfCmAfGmCfUmAfGm

AfAmCfU(ps)mU(ps)fA 3'

Example 4

In Vivo Assay and Duration of TTR Knockdown in Mice 8 weeks old male C57BL/6JOlaHsd mice were injected with the respective dose with a single subcutaneous injection of 300 uL/kg (4 animals per group).

At each timepoint mice were sacrificed, the liver were harvested and analysed for TTR mRNA using TAQman analysis.

Target Gene Expression In Vivo:

Total RNA was isolated from fresh liver tissue essentially as described in Fehring et al. 2014:

For target mRNA knockdown analyses, tissues were dissected immediately after sacrifice of the mice and instantly snap-frozen in liquid nitrogen. Approximately 20 mg of tissue was homogenized in a Mixer Mill MM 301 (Retsch GmbH, Haan, Germany) using tungsten carbide beads (Qiagen, Hilden, Germany). TotalRNA was isolated from the lysate with the Invisorb Spin Tissue RNA MiniKit (Invitek, Berlin, Germany). Depending on the tissue, 25-100 ng total RNA was used for quantitative TaqMan RT-PCR with the amplicon sets obtained from BioTez GmBH, Berlin, Germany: The TaqMan RT-PCR reactions were carried out with an ABI PRISM 7700 Sequence Detector (Software: Sequence Detection System v1.6.3 (ABI Life Technologies)) or StepOnePlus Real Time PCR System (ABI) using a standard protocol for RT-PCR (as described in Fehring et al. 2014) with primers and probes at a concentration of 300 and 100 nmol/l respectively. TaqMan data were calculated by using the comparative Ct method. mRNA level were normalised against PTEN.

Amplicon Sets for Detection of TTR mRNA

| | | |
|---|---|---|
| mmTTR: | 467U22 | TGGACACCAAATCGTACTGGAA |
| mmTTR: | 550L22 | CAGAGTCGTTGGCTGTGAAAAC |
| mmTTR: | 492U27FL | ACTTGGCATTTCCCCGTTCCATGAATT |

Amplicon Sets for Detection of PTEN mRNA

| | |
|---|---|
| PTEN | CACCGCCAAATTTAACTGCAGA |
| PTEN | AAGGGTTTGATAAGTTCTAGCTGT |
| PTEN | TGCACAGTATCCTTTTGAAGACCATAACCCA |

Figure 1:
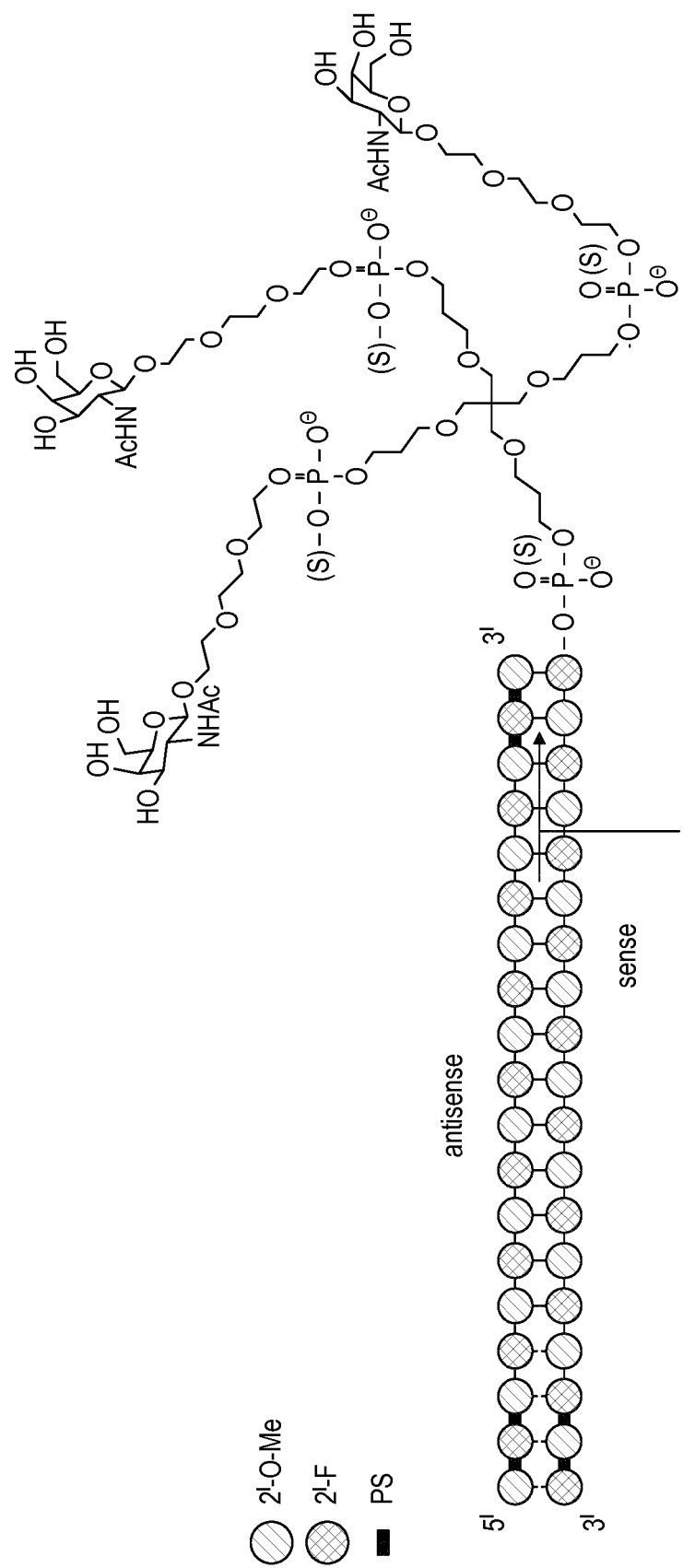
FIG. 1 provides an illustration of a modified double stranded siRNA conjugated to a three saccharide ligand moiety modified with thiophosphate groups.
Figure 2:
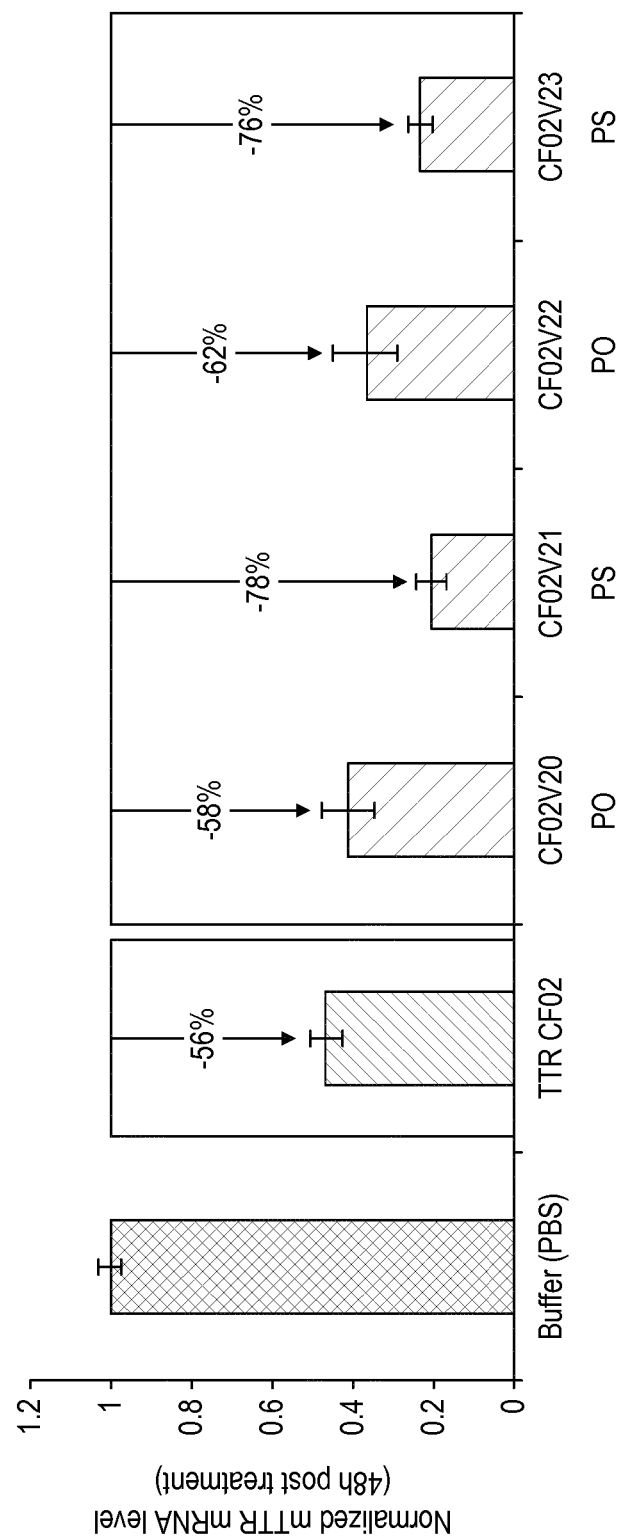
FIG. 2 is a bar chart illustrating in vivo efficacy in mice with in vivo efficacy of TTR knockdown in mice. Mice (4 animals per group) were treated with a single subcuteanous dose of 1 mg/kg and sacrifised after 2 days post injection. TTR mRNA level was quantified by TAQman PCR. The level of knockdown is shown above the bars. mRNA level were normalised against PTEN. The introduction of phosphorothioates in the GalNAc linker system as in TTR CF02V21 and TTR CF02V23 showed substantially greater potency compared to standard phosphodiester linkage (as in TTR CF02V20 and TTR CF02V22).

The above method was used, with a single subcutaneous dose of 1 mg/kg. Mice were sacrificed 2 days post injection. The tested compounds were TTR CF02, TTR CF02V20, TTR CF02V21, TTR CF02V22 and TTR CF02V23. Introduction of phosphorothioates in the GalNAc linker system (TTR CF02V21 and TTR CF02V23) showed substantially greater potency compared to standard phosphodiester linkage (TTR CF02V20 and TTR CF02V22). Results are shown in FIG. 2.

Figure 3:
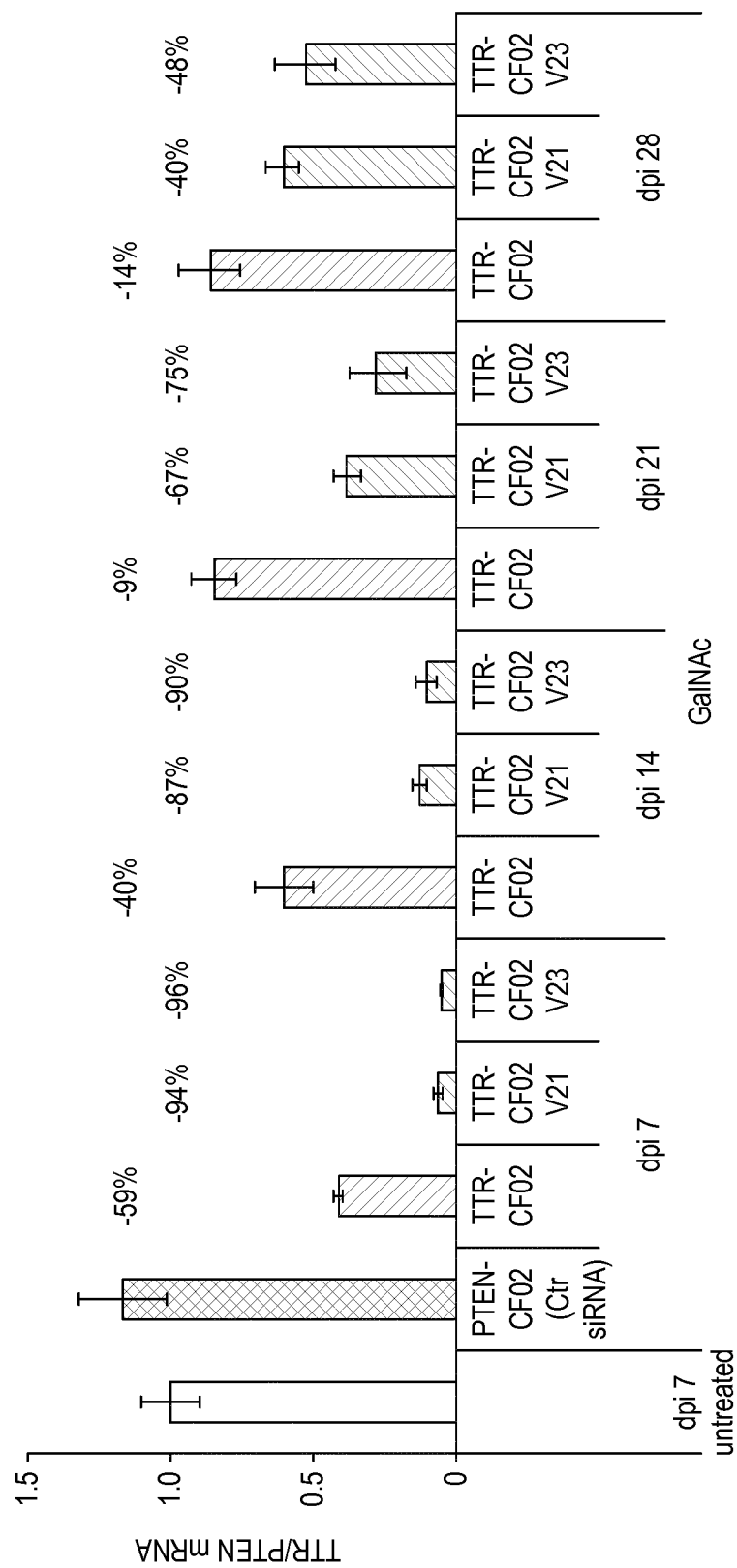
FIG. 3 is a bar chart illustrating the duration of TTR knockdown in mice. Mice (4 animals per group) were treated with a single subcuteanous dose of 2 mg/kg and sacrifised at the given time points (7, 14, 21 and 28 days post injection). TTR mRNA level was quantified by TAQman PCR. The level of knockdown is shown above the bars. mRNA level were normalised against PTEN.

The above method was used, with a single subcutaneous dose of 2 mg/kg. Mice were sacrificed at given timepoints (7, 14, 21 and 28 days post injection). The tested compounds were PTEN CF02 (control), TTR CF02, TTR CF02V21 and TTR CF02V23. Results are shown in FIG. 3.

Example 5

Dose Titration of TTR CF02V21 and TTR CF02V23

8 weeks old male C57BL/6JOlaHsd mice were injected with the respective dose (3, 1, 0.3, 0.1 mg/kg) with a single subcutaneous injection of 300 uL/kg (4 animals per group). PBS was used as a control. After two days mice were sacrificed, the liver were harvested and analysed for TTR mRNA using TAQman analysis. Analysis of samples was performed as in Example 4.

Both siRNA GalNAc conjugates TTR CF02V21 and TTR CF02V23 were very effective in reducing TTR levels in a dose dependent manner. Results are shown in FIG. 4.

Example 6

In Vitro Determination of TTR Knockdown of Various TTR siRNA GalNAc Conjugates

In vitro determination of TTR knockdown of various TTR siRNA GalNAc conjugates STS016 L4-L9 was determined in a hepatocyte assay.

Primary Hepatocytes (Life technology) were seeded into 6 well plates (600,000 cells per well) according to manufacturer's protocol and incubated with the respective concentration of the GalNac conjugate. Cells were harvested 24 h post incubation and RNA was isolated and analysed using Taqman analysis as in Example 4.

All different siRNA GalNAc conjugates STS016 L4-L9 were very effective in reducing TTR levels. Results are shown in FIGS. 5 and 6. TTR CF02V23 represents the positive control. GN_Luc represents the negative control.

Example 7

In Vivo Assay and Duration of TTR Knockdown in Mice 8 weeks old male C57BL/6JOlaHsd mice were injected with the dose of 1 mg/kg with a single subcutaneous Injection of 300 uL/kg (4 animals per group).

Blood was taken after each timepoint (day 8, 15, 22 post injection) and analysed for TTR level using commercially available murineTTR specific Elisa Kit.

All different siRNA GalNAc conjugates STS016 L4-L9 were very effective in reducing TTR levels. Results are shown in FIG. 7.

Example 8

In Vivo Assay of PTEN Knockdown in Mice 8 weeks old male C57BL/6JOlaHsd mice were injected with the respective dose (1, 3, 10 mg/kg) with a single subcutaneous injection of 300 uL/kg (4 animals per group). PBS was used as control.

2 days after administration, mice were sacrificed, the liver were harvested and analysed for PTEN mRNA using TAQman analysis.

Target Gene Expression In Vivo:

Total RNA was isolated from fresh liver tissue essentially as described in Fehring et al. 2014:

For target mRNA knockdown analyses, tissues were dissected immediately after sacrifice of the mice and instantly snap-frozen in liquid nitrogen. Approximately 20 mg of tissue was homogenized in a Mixer Mill MM 301 (Retsch GmbH, Haan, Germany) using tungsten carbide beads (Qiagen, Hilden, Germany). TotalRNA was isolated from the lysate with the Invisorb Spin Tissue RNA MiniKit (Invitek, Berlin, Germany). Depending on the tissue, 25-100 ng total RNA was used for quantitative TaqMan RT-PCR with the amplicon sets obtained from BioTez GmBH, Berlin, Germany: The TaqMan RT-PCR reactions were carried out with an ABI PRISM 7700 Sequence Detector (Software: Sequence Detection System v1.6.3 (ABI Life Technologies)) or StepOnePlus Real Time PCR System (ABI) using a standard protocol for RT-PCR (as described in Fehring et al. 2014) with primers and probes at a concentration of 300 and 100 nmol/l respectively. TaqMan probes for PTEN were the same as described in Example 4.

Results are shown in FIG. 8. A clear dose dependent knockdown of PTEN was demonstrated.

REFERENCES

1. Fire, A.; Xu, S.; Montgomery, M. K.; Kostas, S. A.; Driver, S. E.; Mello, C. C., Potent and specific genetic interference by double-stranded RNA in Caenorhabditis elegans. *Nature* 1998, 391 (6669), 806-11.
2. Elbashir, S. M.; Lendeckel, W.; Tuschl, T., RNA interference is mediated by 21- and 22-nucleotide RNAs. *Genes & development* 2001, 15 (2), 188-200.
3. Dubber, M.; Frechet, J. M., Solid-phase synthesis of multivalent glycoconjugates on a DNA synthesizer. *Bioconjugate chemistry* 2003, 14 (1), 239-46.
4. Weigel, P. H.; Yik, J. H., Glycans as endocytosis signals: the cases of the asialoglycoprotein and hyaluronan/chondroitin sulfate receptors. *Biochim Biophys Acta* 2002, 1572 (2-3), 341-63.
5. Ishibashi, S.; Hammer, R. E.; Herz, J., Asialoglycoprotein receptor deficiency in mice lacking the minor receptor subunit. *J Biol Chem* 1994, 269 (45), 27803-6.
6. Biessen, E. A.; Broxterman, H.; van Boom, J. H.; van Berkel, T. J., The cholesterol derivative of a triantennary galactoside with high affinity for hepatic asialoglycoprotein receptor: a potent cholesterol lowering agent. *J Med Chem* 1995, 38 (11), 1846-52.
7. Akinc, A.; Querbes, W.; De, S.; Qin, J.; Frank-Kamenetsky, M.; Jayaprakash, K. N.; Jayaraman, M.; Rajeev, K. G.; Cantley, W. L.; Dorkin, J. R.; Butler, J. S.; Qin, L.; Racie, T.; Sprague, A.; Fava, E.; Zeigerer, A.; Hope, M. J.; Zerial, M.; Sah, D. W.; Fitzgerald, K.; Tracy, M. A.; Manoharan, M.; Koteliansky, V.; Fougerolles, A. d.; Maier, M. A., Targeted Delivery of RNAi Therapeutics With Endogenous and Exogenous Ligand-Based Mechanisms. *Molecular therapy: the journal of the American Society of Gene Therapy* 2010, 18 (7), 1357-1364.
8. Fehring, V.; Schaeper, U.; Ahrens, K.; Santel, A.; Keil, O.; Eisermann, M.; Giese, K.; Kaufmann, J., Delivery of therapeutic siRNA to the lung endothelium via novel Lipoplex formulation DACC. *Mol Ther* 2014, 22 (4), 811-20.

9. Prakash, T. P.; Brad Wan, W.; Low, A.; Yu, J.; Chappell, A. E.; Gaus, H.; Kinberger, G. A.; Østergaard, M. E.; Migawa, M. T.; Swayze, E. E.; Seth, P. P., Solid-phase synthesis of 5'-triantennary N-acetylgalactosamine conjugated antisense oligonucleotides using phosphoramidite chemistry. *Bioorganic & medicinal chemistry letters* 2015, 25 (19), 4127-4130.

10. Li, L.-C.; Okino, S. T.; Zhao, H.; Pookot, D.; Place, R. F.; Urakami, S.; Enokida, H.; Dahiya, R., Small dsRNAs induce transcriptional activation in human cells. *Proceedings of the National Academy of Sciences* 2006, 103 (46), 17337-17342.

The invention claimed is:
1. A compound selected from the following formulas:
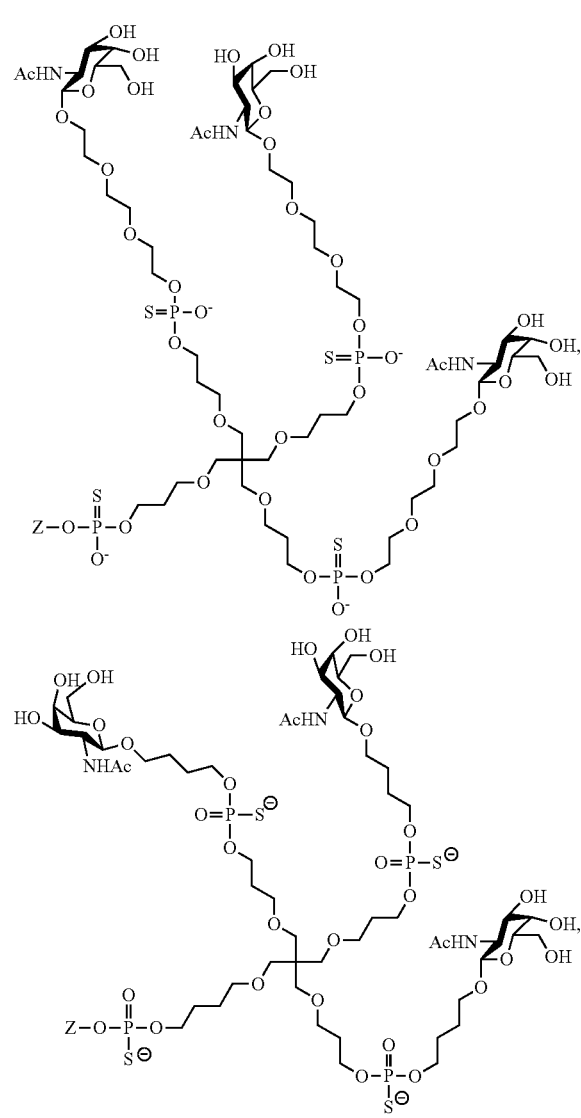
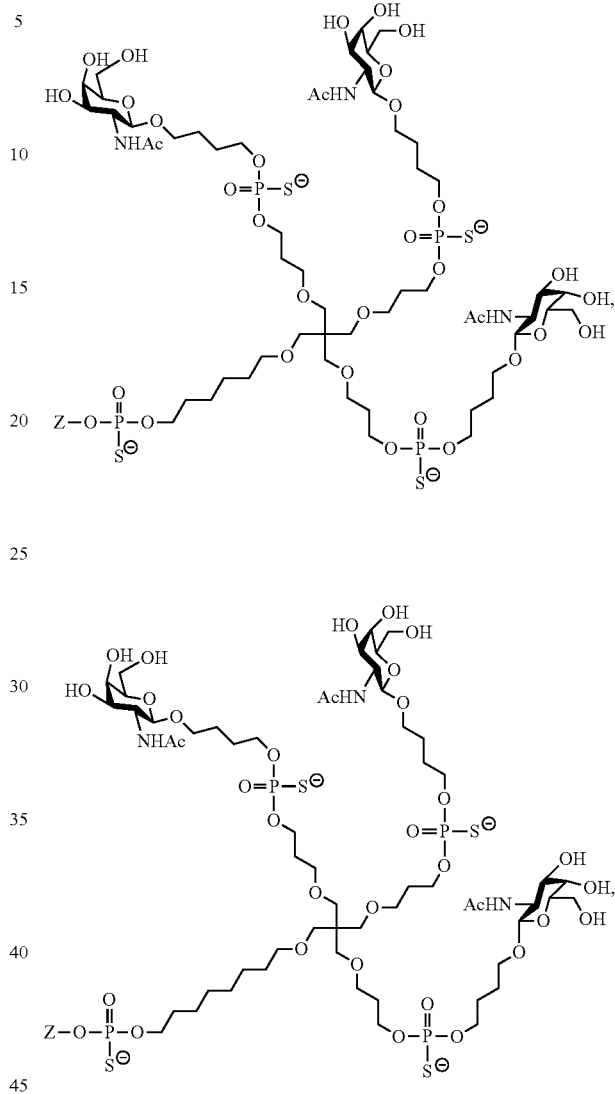
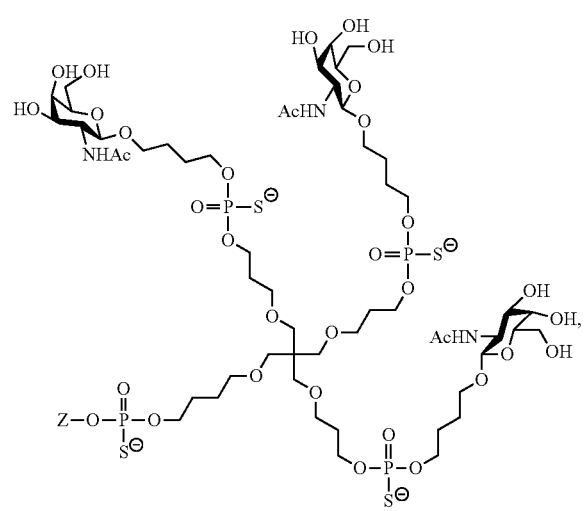
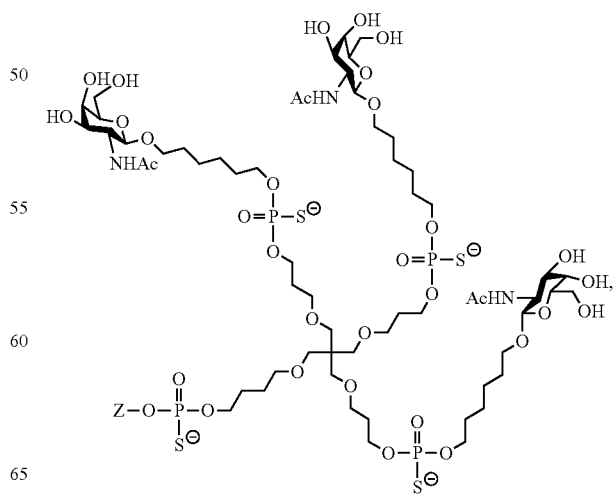

81
-continued
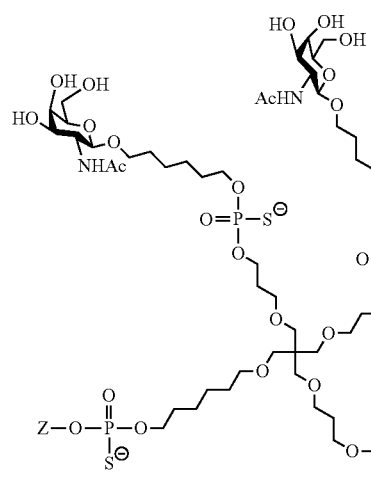
and
82
-continued
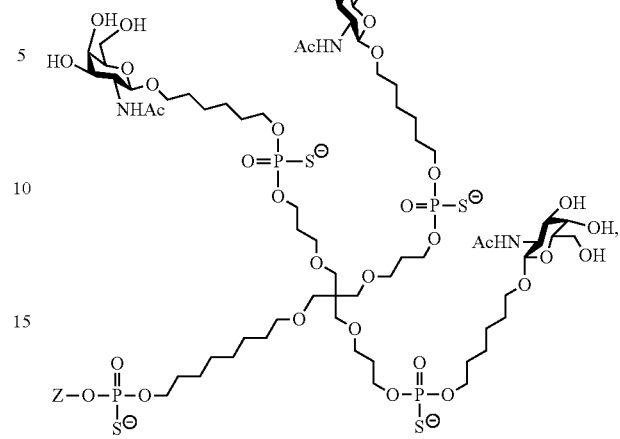
wherein Z is a nucleic acid.
2. The compound according to claim 1, wherein the nucleic acid is selected from RNAi, siRNA, antisense nucleic acid, ribozyme, aptamer and spiegelmer.
3. A composition comprising a compound as defined in claim 1 and a suitable carrier or excipient.
* * * * *

```
                        SEQUENCE LISTING

<160> NUMBER OF SEQ ID NOS: 12

<210> SEQ ID NO 1
<211> LENGTH: 21
<212> TYPE: RNA
<213> ORGANISM: Artificial Sequence
<220> FEATURE:
<223> OTHER INFORMATION: TTR CF02 - Antisense strand

<400> SEQUENCE: 1
uuauagagca agaacacugu u                                           21

<210> SEQ ID NO 2
<211> LENGTH: 21
<212> TYPE: RNA
<213> ORGANISM: Artificial Sequence
<220> FEATURE:
<223> OTHER INFORMATION: TTR CF02 - Sense strand

<400> SEQUENCE: 2
aacaguguuc uugcucuaua a                                           21

<210> SEQ ID NO 3
<211> LENGTH: 19
<212> TYPE: RNA
<213> ORGANISM: Artificial Sequence
<220> FEATURE:
<223> OTHER INFORMATION: GN_Luc Antisense strand

<400> SEQUENCE: 3
ucgaaguauu ccgcguacg                                              19

<210> SEQ ID NO 4
<211> LENGTH: 19
<212> TYPE: RNA
<213> ORGANISM: Artificial Sequence
<220> FEATURE:
<223> OTHER INFORMATION: GN_Luc Sense strand

<400> SEQUENCE: 4
cguacgcgga auacuucga                                              19

<210> SEQ ID NO 5
<211> LENGTH: 19
<212> TYPE: RNA
<213> ORGANISM: Artificial Sequence
<220> FEATURE:
<223> OTHER INFORMATION: GN_PTENV10F Antisense strand

<400> SEQUENCE: 5
uaaguucuag cuguggugg                                              19

<210> SEQ ID NO 6
<211> LENGTH: 19
<212> TYPE: RNA
<213> ORGANISM: Artificial Sequence
```

```
<220> FEATURE:
<223> OTHER INFORMATION: GN_PTENV10F Sense strand

<400> SEQUENCE: 6
ccaccacagc uagaacuua                                               19

<210> SEQ ID NO 7
<211> LENGTH: 22
<212> TYPE: DNA
<213> ORGANISM: Artificial Sequence
<220> FEATURE:
<223> OTHER INFORMATION: mmTTR:467U22

<400> SEQUENCE: 7
tggacaccaa atcgtactgg aa                                           22

<210> SEQ ID NO 8
<211> LENGTH: 22
<212> TYPE: DNA
<213> ORGANISM: Artificial Sequence
<220> FEATURE:
<223> OTHER INFORMATION: mmTTR:550L22

<400> SEQUENCE: 8
cagagtcgtt ggctgtgaaa ac                                           22

<210> SEQ ID NO 9
<211> LENGTH: 27
<212> TYPE: DNA
<213> ORGANISM: Artificial Sequence
<220> FEATURE:
<223> OTHER INFORMATION: mmTTR:492U27FL

<400> SEQUENCE: 9
acttggcatt tccccgttcc atgaatt                                      27

<210> SEQ ID NO 10
<211> LENGTH: 22
<212> TYPE: DNA
<213> ORGANISM: Artificial Sequence
<220> FEATURE:
<223> OTHER INFORMATION: Amplicon for detection of PTEN mRNA

<400> SEQUENCE: 10
caccgccaaa tttaactgca ga                                           22

<210> SEQ ID NO 11
<211> LENGTH: 24
<212> TYPE: DNA
<213> ORGANISM: Artificial Sequence
<220> FEATURE:
<223> OTHER INFORMATION: Amplicon for detection of PTEN mRNA

<400> SEQUENCE: 11
aagggtttga taagttctag ctgt                                         24

<210> SEQ ID NO 12
<211> LENGTH: 31
<212> TYPE: DNA
<213> ORGANISM: Artificial Sequence
<220> FEATURE:
<223> OTHER INFORMATION: Amplicon for detection of PTEN mRNA

<400> SEQUENCE: 12
tgcacagtat cctttgaag accataaccc a                                  31
```